US010251922B2

(12) United States Patent
Palese et al.

(10) Patent No.: US 10,251,922 B2
(45) Date of Patent: Apr. 9, 2019

(54) NEWCASTLE DISEASE VIRUSES AND USES THEREOF

(71) Applicants: Icahn School of Medicine at Mount Sinai, New York, NY (US); Memorial Sloan Kettering Cancer Center, New York, NY (US)

(72) Inventors: Peter Palese, New York, NY (US); Adolfo Garcia-Sastre, New York, NY (US); Dmitriy Zamarin, New York, NY (US); Jedd D. Wolchok, New York, NY (US)

(73) Assignees: Icahn School of Medicine at Mount Sinai, New York, NY (US); Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/789,539

(22) Filed: Oct. 20, 2017

(65) Prior Publication Data
US 2018/0280455 A1    Oct. 4, 2018

Related U.S. Application Data

(62) Division of application No. 14/205,776, filed on Mar. 12, 2014, now abandoned.

(60) Provisional application No. 61/782,994, filed on Mar. 14, 2013.

(51) Int. Cl.
*A61K 35/768*    (2015.01)
*A61K 39/00*    (2006.01)
*C07K 16/28*    (2006.01)
*A61K 39/395*    (2006.01)
*C12N 7/00*    (2006.01)

(52) U.S. Cl.
CPC ........ *A61K 35/768* (2013.01); *A61K 39/3955* (2013.01); *C07K 16/2818* (2013.01); *C07K 16/2827* (2013.01); *C07K 16/2878* (2013.01); *C12N 7/00* (2013.01); *A61K 2039/505* (2013.01); *C07K 2317/76* (2013.01); *C12N 2760/18121* (2013.01); *C12N 2760/18122* (2013.01); *C12N 2760/18132* (2013.01); *C12N 2760/18133* (2013.01); *C12N 2760/18143* (2013.01)

(58) Field of Classification Search
None
See application file for complete search history.

(56) References Cited

U.S. PATENT DOCUMENTS

| | | |
|---|---|---|
| 5,166,057 A | 11/1992 | Palese et al. |
| 5,223,409 A | 6/1993 | Ladner et al. |
| 5,273,745 A | 12/1993 | Schirrmacher |
| 5,403,484 A | 4/1995 | Ladner et al. |
| 5,571,698 A | 11/1996 | Ladner et al. |
| 5,786,199 A | 7/1998 | Palese |
| 5,854,037 A | 12/1998 | Palese et al. |
| 5,891,680 A | 4/1999 | Lieschke et al. |
| 6,146,642 A | 11/2000 | Garcia-Sastre et al. |
| 6,190,901 B1 | 2/2001 | Sundick et al. |
| 6,287,554 B1 | 9/2001 | Sundick et al. |
| 6,451,323 B1 | 9/2002 | Garcia-Sastre et al. |
| 6,544,785 B1 | 4/2003 | Palese et al. |
| 6,635,416 B2 | 10/2003 | Palese et al. |
| 6,649,372 B1 | 11/2003 | Palese et al. |
| 6,719,979 B2 | 4/2004 | Peeters et al. |
| 6,737,522 B2 | 5/2004 | Sundick et al. |
| 6,852,522 B1 | 2/2005 | Palese et al. |
| 6,896,881 B1 | 5/2005 | Russell et al. |
| 7,052,685 B1 | 5/2006 | Rook |
| 7,056,689 B1 | 6/2006 | Lorence et al. |
| 7,060,430 B2 | 6/2006 | Palese et al. |
| 7,141,550 B2 | 11/2006 | Molling et al. |
| 7,244,558 B1 | 7/2007 | Samal et al. |
| 7,332,169 B2 | 2/2008 | Peeters et al. |
| 7,384,774 B2 | 6/2008 | Palese et al. |
| 7,442,379 B2 | 10/2008 | Garcia-Sastre et al. |
| 7,442,527 B2 | 10/2008 | Palese et al. |

(Continued)

FOREIGN PATENT DOCUMENTS

AU    2002307971 B2    10/2002
CN    101787373    6/2013

(Continued)

OTHER PUBLICATIONS

Narvaiza et al. Intratumoral Coinjection of Two Adenoviruses, One Encoding the Chemokine IFN-g-Inducible Protein-10 and Another Encoding IL-12, Results in Marked Antitumoral Synergy. The Journal of Immunology, 2000, 164: 3112-3122.*

(Continued)

*Primary Examiner* — Nianxiang Zou
(74) *Attorney, Agent, or Firm* — Jones Day

(57) ABSTRACT

Described herein are chimeric Newcastle disease viruses engineered to express an agonist of a co-stimulatory signal of an immune cell and compositions comprising such viruses. Also described herein are chimeric Newcastle disease viruses engineered to express an antagonist of an inhibitory signal of an immune cell and compositions comprising such viruses. The chimeric Newcastle disease viruses and compositions are useful in the treatment of cancer. In addition, described herein are methods for treating cancer comprising administering Newcastle disease viruses in combination with an agonist of a co-stimulatory signal of an immune and/or an antagonist of an inhibitory signal of an immune cell.

20 Claims, 34 Drawing Sheets

(56) References Cited

U.S. PATENT DOCUMENTS

Figure 1:
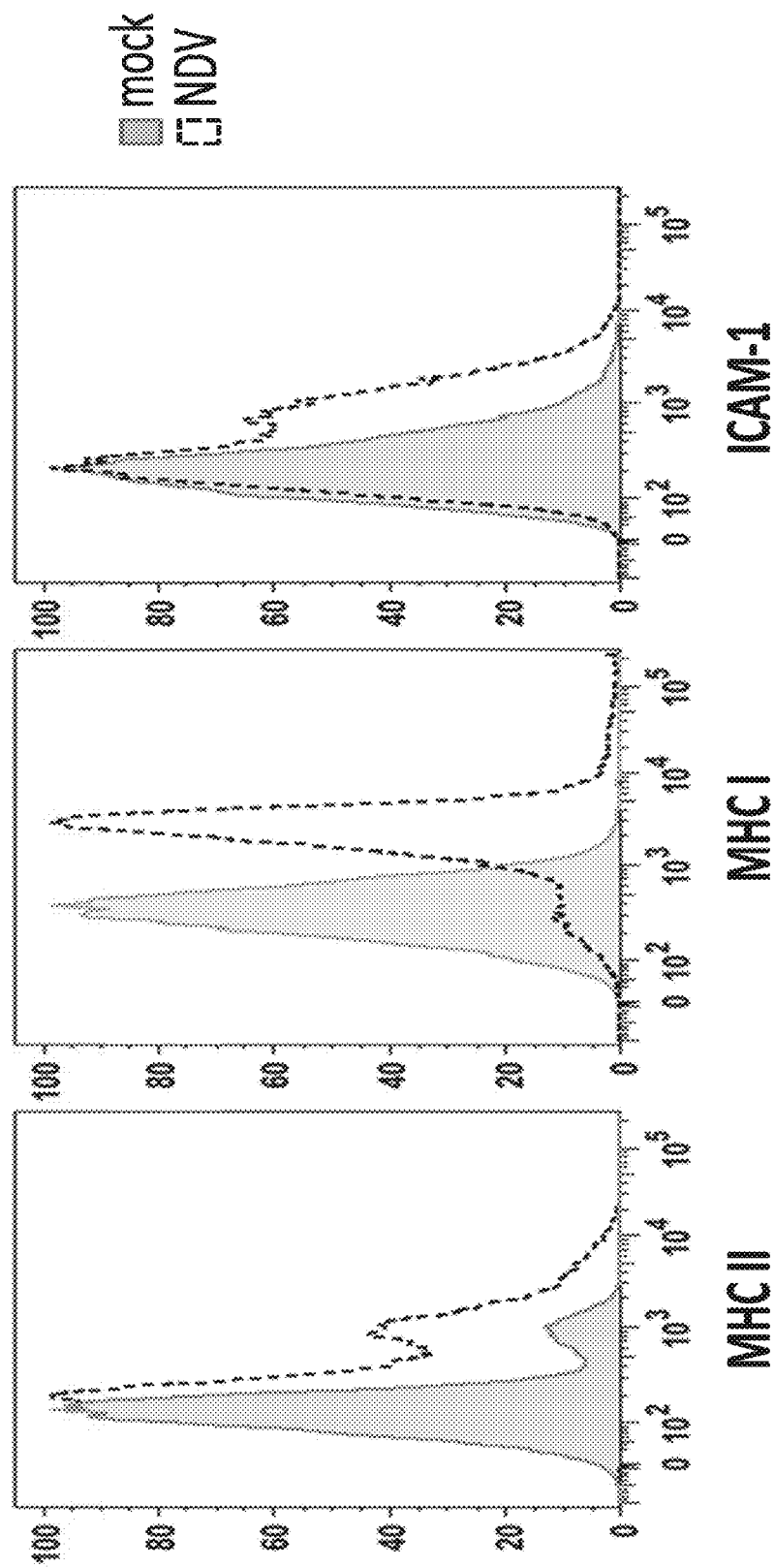
Figure 2A:
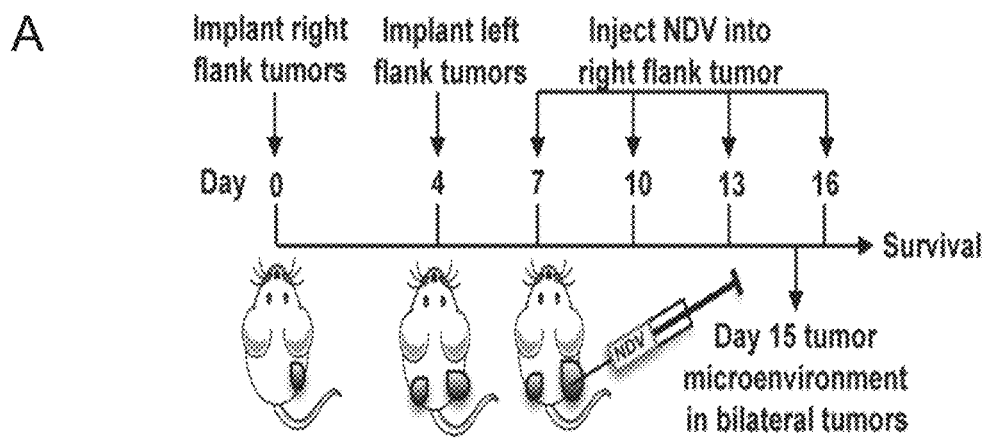
Figure 2B:
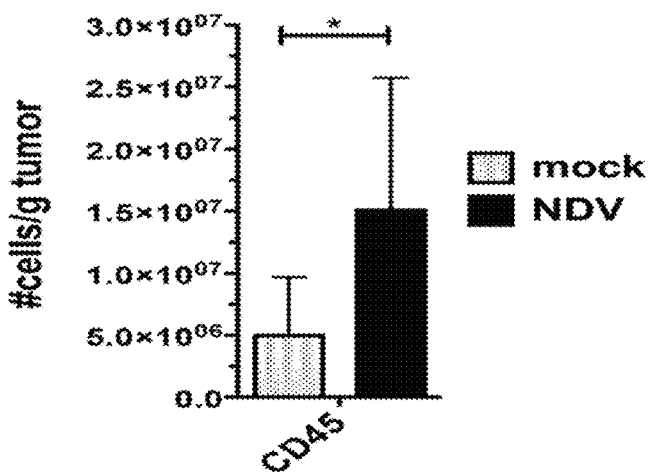
Figure 2C:
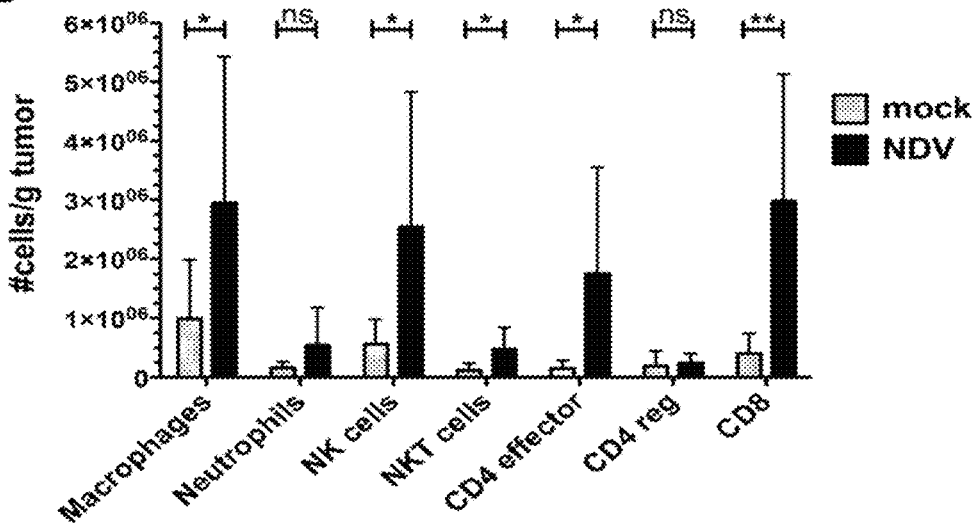
Figure 2D:
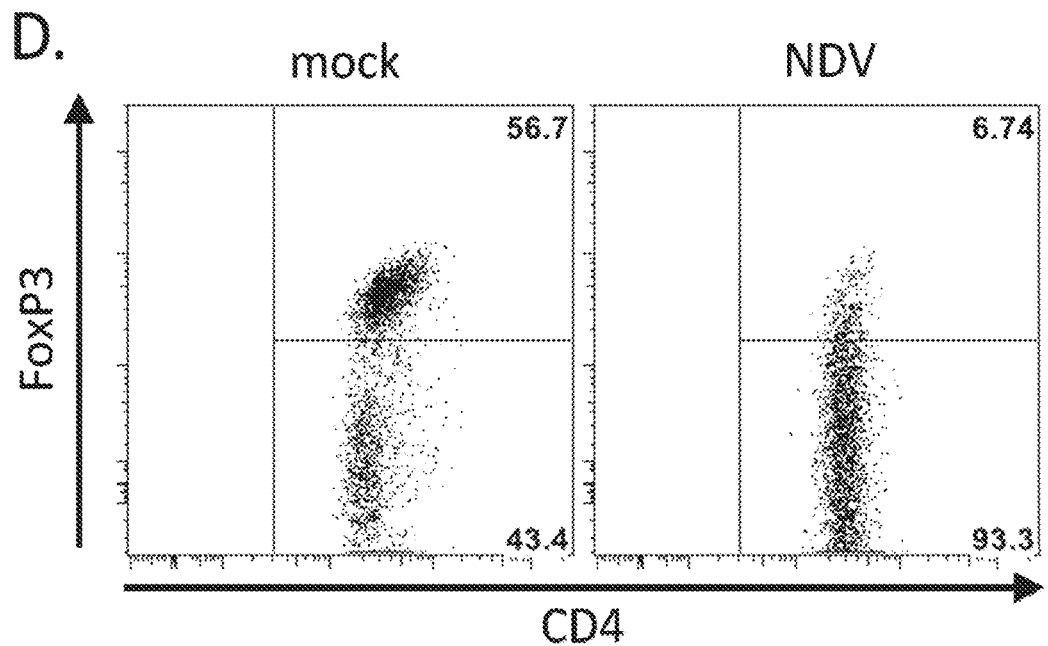
Figure 2E:
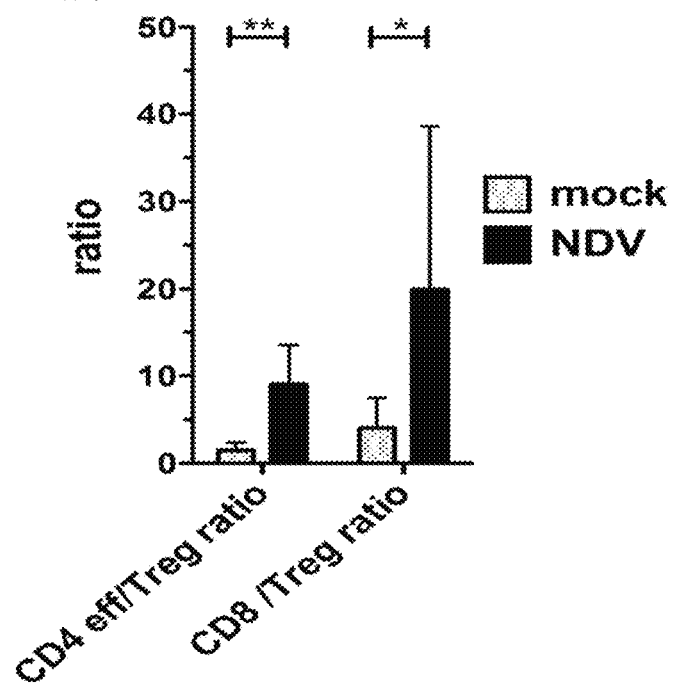

| | | |
|---|---|---|
| 7,470,426 B1 | 12/2008 | Roberts et al. |
| 7,494,808 B2 | 2/2009 | Palese et al. |
| 7,547,442 B2 | 6/2009 | Peeters et al. |
| 7,736,640 B2 | 6/2010 | Lorence et al. |
| 7,780,962 B2 | 8/2010 | Roberts et al. |
| 7,833,774 B2 | 11/2010 | Palese et al. |
| 7,858,081 B2 | 12/2010 | Bernard et al. |
| 8,043,612 B2 | 10/2011 | Roberts et al. |
| 8,105,578 B2 | 1/2012 | Roberts et al. |
| 8,124,084 B2 | 2/2012 | Lefrancois et al. |
| 8,163,879 B2 | 4/2012 | Wong et al. |
| 8,475,790 B2 | 7/2013 | Jure-Kunkel |
| 8,490,289 B2 | 7/2013 | Nystrom et al. |
| 8,492,118 B2 | 7/2013 | Wong et al. |
| 8,507,222 B2 | 8/2013 | Wong et al. |
| 8,591,881 B2 | 11/2013 | Palese et al. |
| 8,709,417 B2 | 4/2014 | Allison et al. |
| 8,765,462 B2 | 7/2014 | Medin et al. |
| 8,871,191 B2 | 10/2014 | Pavlakis et al. |
| 8,940,288 B2 | 1/2015 | Lefrancois et al. |
| 9,217,136 B2 | 12/2015 | Palese et al. |
| 9,375,475 B2 | 6/2016 | Allison et al. |
| 9,387,242 B2 | 7/2016 | Palese et al. |
| 9,476,033 B2 | 10/2016 | Samal et al. |
| 10,023,637 B2 | 7/2018 | Allison et al. |
| 2002/0052030 A1 | 5/2002 | Wonderling et al. |
| 2002/0150554 A1 | 10/2002 | Sundick et al. |
| 2003/0044384 A1 | 3/2003 | Roberts et al. |
| 2003/0224017 A1 | 12/2003 | Samal et al. |
| 2004/0234552 A1 | 11/2004 | Peeters et al. |
| 2005/0048549 A1 | 3/2005 | Cao et al. |
| 2005/0191617 A1 | 9/2005 | Inoue et al. |
| 2005/0235134 A1 | 10/2005 | O'Sullivan |
| 2005/0238622 A1 | 10/2005 | Axelrod et al. |
| 2006/0216310 A1 | 9/2006 | Lorence et al. |
| 2008/0057037 A1 | 3/2008 | Roberts et al. |
| 2008/0206201 A1 | 8/2008 | Beier et al. |
| 2009/0061521 A1 | 3/2009 | Palese et al. |
| 2009/0081161 A1 | 3/2009 | Roberts et al. |
| 2009/0082299 A1 | 3/2009 | Felber et al. |
| 2009/0175826 A1 | 7/2009 | Subbiah et al. |
| 2009/0214590 A1 | 8/2009 | Sundick et al. |
| 2009/0238791 A1 | 9/2009 | Jacques et al. |
| 2009/0280144 A1 | 11/2009 | Garcia-Sastre et al. |
| 2010/0092430 A1 | 4/2010 | Beier et al. |
| 2010/0297072 A1 | 11/2010 | DePinho et al. |
| 2011/0020282 A1 | 1/2011 | Beier et al. |
| 2011/0044937 A1 | 2/2011 | Bell et al. |
| 2011/0081311 A1 | 4/2011 | Pavlakis et al. |
| 2011/0158938 A1 | 6/2011 | Bernard et al. |
| 2011/0189189 A1 | 8/2011 | Jure-Kunkel |
| 2012/0034242 A1 | 2/2012 | Jooss et al. |
| 2012/0058141 A1 | 3/2012 | Palese et al. |
| 2012/0058538 A1 | 3/2012 | Palese et al. |
| 2012/0064112 A1 | 3/2012 | Samal et al. |
| 2012/0071859 A1 | 3/2012 | Morgan et al. |
| 2012/0114648 A1 | 5/2012 | Langermann et al. |
| 2012/0122185 A1 | 5/2012 | Palese et al. |
| 2013/0108665 A1 | 5/2013 | Liang |
| 2014/0044678 A1 | 2/2014 | Palese et al. |
| 2014/0134128 A1 | 5/2014 | Wong et al. |
| 2014/0186303 A1 | 7/2014 | Subbiah et al. |
| 2014/0205560 A1 | 7/2014 | Wong et al. |
| 2014/0219955 A1 | 8/2014 | Wong et al. |
| 2014/0242025 A1 | 8/2014 | Wong et al. |
| 2014/0271677 A1 | 9/2014 | Palese et al. |
| 2014/0377221 A1 | 12/2014 | Tufaro et al. |
| 2015/0017121 A1 | 1/2015 | Becher et al. |
| 2015/0093357 A1 | 4/2015 | Lefrancois et al. |
| 2015/0132257 A1 | 5/2015 | Wong et al. |
| 2015/0133531 A1 | 5/2015 | Wiegand |
| 2015/0139945 A1 | 5/2015 | Lefrancois et al. |
| 2015/0152188 A1 | 6/2015 | Morisseau et al. |
| 2015/0250837 A1 | 9/2015 | Nolin et al. |
| 2016/0015760 A1 | 1/2016 | Palese et al. |
| 2016/0068823 A1 | 3/2016 | Palese et al. |
| 2017/0037379 A1 | 2/2017 | Palese et al. |
| 2017/0247425 A1 | 8/2017 | Ungerechts et al. |
| 2018/0078592 A1 | 3/2018 | Palese et al. |
| 2018/0251555 A1 | 9/2018 | Allison et al. |
| 2018/0256655 A1 | 9/2018 | Palese et al. |

FOREIGN PATENT DOCUMENTS

| | | |
|---|---|---|
| CN | 105 734 023 A | 7/2016 |
| CN | 106166294 A | 11/2016 |
| DE | 3922-444 A | 1/1991 |
| EP | 0702085 | 3/1996 |
| EP | 780475 | 6/1997 |
| EP | 0974660 | 1/2000 |
| EP | 1248654 B1 | 10/2005 |
| EP | 1032269 B1 | 8/2007 |
| EP | 1486211 B1 | 10/2008 |
| EP | 2085092 | 8/2009 |
| EP | 2669381 | 12/2013 |
| EP | 2766035 B1 | 8/2014 |
| EP | 2393921 B1 | 7/2015 |
| EP | 2987856 A1 | 2/2016 |
| JP | 2012-527465 A | 11/2012 |
| WO | WO 1994/025627 | 11/1994 |
| WO | WO 96/34625 | 11/1996 |
| WO | WO 97/06270 | 2/1997 |
| WO | WO 97/12032 | 4/1997 |
| WO | WO 1997/014433 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 1999/018799 | 4/1999 |
| WO | WO 99/66045 | 12/1999 |
| WO | WO 2000/062735 | 10/2000 |
| WO | WO 2000/067786 | 11/2000 |
| WO | WO 01/04333 | 1/2001 |
| WO | WO 2001/020989 | 3/2001 |
| WO | WO 2002/081621 | 10/2002 |
| WO | WO 2002/102404 | 12/2002 |
| WO | WO 2003/092579 | 11/2003 |
| WO | WO 2006/050984 | 5/2006 |
| WO | WO 2007/008918 | 1/2007 |
| WO | WO 2007/064802 | 6/2007 |
| WO | WO 2007/084342 | 7/2007 |
| WO | WO 2007/113648 A2 | 10/2007 |
| WO | WO 2008/011726 | 1/2008 |
| WO | WO 2008/156712 A1 | 12/2008 |
| WO | WO 2009/002562 | 12/2008 |
| WO | WO 2009/095167 | 8/2009 |
| WO | WO 2010/091262 | 8/2010 |
| WO | WO 2010/135242 A1 | 11/2010 |
| WO | WO 2011/022656 A2 | 2/2011 |
| WO | WO 2011/041613 A2 | 4/2011 |
| WO | WO 2011/119628 | 9/2011 |
| WO | WO 2012/000188 | 1/2012 |
| WO | WO 2012/000443 | 1/2012 |
| WO | WO 2012/142529 | 10/2012 |
| WO | WO 2013/053775 A1 | 4/2013 |
| WO | WO 2013/112942 | 8/2013 |
| WO | WO 2013/112942 A1 | 8/2013 |
| WO | WO 2013/178344 | 12/2013 |
| WO | WO 2014/047350 | 3/2014 |
| WO | WO 2016/048903 A1 | 3/2014 |
| WO | WO 2014/066527 | 5/2014 |
| WO | WO 2014/158811 | 10/2014 |
| WO | WO 2014/170032 | 10/2014 |
| WO | WO 2015/018528 | 2/2015 |
| WO | WO 2015/018529 | 2/2015 |
| WO | WO 2015/032755 | 3/2015 |
| WO | WO 2015/127501 A1 | 9/2015 |
| WO | WO 2015/131994 | 9/2015 |
| WO | WO 2016/018920 | 2/2016 |
| WO | WO 2016/048903 A1 | 3/2016 |
| WO | WO 2016/094377 A1 | 6/2016 |
| WO | WO 2017/019894 A1 | 2/2017 |
| WO | WO 2017/019896 A1 | 2/2017 |

(56) References Cited

FOREIGN PATENT DOCUMENTS

| | | |
|---|---|---|
| WO | WO 2017/019897 A1 | 2/2017 |
| WO | WO 2017/062953 A1 | 4/2017 |
| WO | WO 2017/083291 A1 | 5/2017 |
| WO | WO 2017/118867 A1 | 7/2017 |
| WO | WO 2017/123981 A1 | 7/2017 |
| WO | WO 2017/190112 A1 | 11/2017 |

OTHER PUBLICATIONS

Topalian et al. Safety, activity, and immune correlates of anti-PD-1 antibody in cancer. N Engl J Med 2012; 366: 2443-54.*
Altomonte et al. Engineered Newcastle Disease Virus as an Improved Oncolytic Agent Against Hepatocellular Carcinoma. Molecular Therapy vol. 18 No. 2, 275-284 Feb. 2010.*
Quetglas et al. Virotherapy with a Semliki Forest Virus-Based Vector Encoding IL12 Synergizes with PD-1/PD-L1 Blockade. Cancer Immunol Res; 3(5); 449-54, 2015.*
U.S. Appl. No. 15/789,340, filed Oct. 20, 2017, Palese et al.
Alexander, 1988, "Newcastle disease, Newcastle disease virus—an avian paramyxovirus", Kluwer Academic Publishers, Dordrecht, The Netherlands, pp. 1-22.
Altomonte et al., "Engineered newcastle disease virus as an improved oncolytic agent against hepatocellular carcinoma," Mol. Ther. 18(2):275-284 (2010).
Bart et al., "Role of interferon in the anti-melanoma effects of poly (I).poly(C) and Newcastle disease virus," Nat. New Biol. 245(147):229-230 (1973).
Bauzon and Hermiston, "Armed therapeutic viruses—a disruptive therapy on the horizon of cancer immunotherapy," Front. Immunol. 5:74 (2014) (eCollection 2014).
Bryant et al., "Development of intermediate-grade (mantle cell) and low-grade (small lymphocytic and marginal zone) human non-Hodgkin's lymphomas xenotransplanted in severe combined immunodeficiency mouse models," Lab. Invest. 80(4):557-573 (2000).
Carthon et al., "Preoperative CTLA-4 blockade: tolerability and immune monitoring in the setting of a presurgical clinical trial," Clin. Canc. Res. 16(10):2861-2871 (2010).
Csatary et al., "MTH-68/H oncolytic viral treatment in human high-grade gliomas," J. Neurooncol. 67(1-2):83-93 (2004).
Curran et al., "Combination CTLA-4 blockade and 4-1BB activation enhances tumor rejection by increasing T-cell infiltration, proliferation, and cytokine production," PLoS One 6(4):e19499 (2011).
Curran et al., "PD-1 and CTLA-4 combination blockade expands infiltrating T cells and reduces regulatory T and myeloid cells within B16 melanoma tumors," Proc. Natl. Acad. Sci. USA 107(9):4275-4280 (2010).
De Leeuw et al., "Virulence of Newcastle disease virus is determined by the cleavage site of the fusion protein and by both the stem region and globular head of the haemagglutinin-neuraminidase protein", J Gen Virol; 86(5):1759-1769 (2005).
Dezfouli et al., "Enhancing CTL responses to melanoma cell vaccines in vivo: synergistic increases obtained using IFNgamma primed and IFNbeta treated B7-1+ B16-F10 melanoma cells," Immunol. Cell. Biol. 81(6):459-471 (2003).
Diamond et al., "Type I interferon is selectively required by dendritic cells for immune rejection of tumors," J. Exp. Med. 208(10):1989-2003 (2011).
Dias et al., "Targeted cancer immunotherapy with oncolytic adenovirus coding for a fully human monoclonal antibody specific for CTLA-4," Gene Ther. 19(10):988-998 (2012).
Dupraz et al., "Dominant negative MyD88 proteins inhibit interleukin-1β/interferon-γ-mediated induction of nuclear factor κB-dependent nitrite production and apoptosis in β cells," J. Biol. Chem. 275(48):37672-37678 (2000).
Elankumaran et al., "Type I interferon-sensitive recombinant Newcastle disease virus for oncolytic virotherapy," J. Virol. 84(8):3835-3844 (2010).

Fecci et al., "Systemic CTLA-4 blockade ameliorates glioma-induced changes to the CD4+ T cell compartment without affecting regulatory T-cell function," Clin. Cancer Res. 13(7):2158-2167 (2007).
Fiola et al., "Tumor selective replication of Newcastle disease virus: association with defects of tumor cells in antiviral defence," Int. J. Cancer 119(2):328-338 (2006).
Fisher et al., "IL-6 trans-signaling licenses mouse and human tumor microvascular gateways for trafficking of cytotoxic T cells," J. Clin. Invest. 121(10):3846-3859 (2011).
Fodde and Smits, "Disease model: familial adenomatous polyposis," Trends Mol. Med. 7(8):369-373 (2001).
Fournier et al., "Oncolytic Newcastle Disease Virus as Cutting Edge between Tumor and Host," Biology (Basel) 2(3):936-975 (2013).
Foy et al., "Regulation of interferon regulatory factor-3 by the hepatitis C virus serine protease," Science 300(5622):1145-1148 (2003).
Franciszkiewicz et al., "Role of chemokines and chemokine receptors in shaping the effector phase of the antitumor immune response," Cancer Res. 72(24):6325-6332 (2012).
Fransen et al., "Controlled Local Delivery of CTLA-4 Blocking Antibody Induces CD8+ T-Cell-Dependent Tumor Eradication and Decreases Risk of Toxic Side Effects," Clin. Cancer Res. 19(19):5381-5389 (2013).
Freeman et al., "Phase I/II trial of intravenous NDV-HUJ oncolytic virus in recurrent glioblastoma multiforme," Mol. Ther. 13(1):221-228 (2006).
Fuertes et al., "Host type I IFN signals are required for antitumor CD8+ T cell responses through CD8{alpha}+ dendritic cells," J. Exp. Med. 208(10):2005-2016 (2011).
Galivo et al., "Interference of CD40L-Mediated Tumor Immunotherapy by Oncolytic Vesicular Stomatitis Virus," Hum. Gene Ther. 21(4):439-450 (2010).
Gao et al., "Expression of transgenes from newcastle disease virus with a segmented genome," J. Virol. 82(6):2692-2698 (2008).
Garcia-Sastre et al., "Use of a mammalian internal ribosomal entry site element for expression of a foreign protein by a transfectant influenza virus," J. Virol. 68(10):6254-6261 (1994).
Garcia-Sastre et al., "Introduction of foreign sequences into the genome of influenza A virus," Dev. Biol. Stand. 82:237-246 (1994).
Genbank Accession No. AAD00274.1, CD70 [Mus musculus]; ROD Jan. 5, 1999.
Genbank Accession No. AF309418.1; Newcastle disease virus B1, complete genome; VRL Dec. 2, 2000.
Genbank Accession No. AY845400.2; Newcastle disease virus strain LaSota, complete genome; VRL Mar. 17, 2005.
Genbank Accession No. CAG46642.1, CD86, partial [*Homo sapiens*]; PRI Jun. 29, 2004.
Genbank Accession No. NC002617.1; Newcastle disease virus B1, complete genome, VRL Nov. 30, 2009.
Genbank Accession No. NM_001252.3, *Homo sapiens* CD70 molecule (CD70), mRNA; PRI Jan. 11, 2014.
Genbank Accession No. NM_003326.3, *Homo sapiens* tumor necrosis factor (ligand) superfamily, member 4 (TNFSF4), mRNA; PRI May 4, 2014.
Genbank Accession No. NM_003811.3, *Homo sapiens* tumor necrosis factor (ligand) superfamily, member 9 (TNFSF9), mRNA; PRI May 10, 2014.
Genbank Accession No. NM_005191.3, *Homo sapiens* CD80 molecule (CD80), mRNA; PRI May 18, 2014.
Genbank Accession No. NM_009404.3, Mus musculus tumor necrosis factor (ligand) superfamily, member 9 (Tnfsf9), mRNA; ROD May 18, 2014.
Genbank Accession No. NM_009452.2, Mus musculus tumor necrosis factor (ligand) superfamily, member 4 (Tnfsf4), mRNA; ROD May 26, 2014.
Genbank Accession No. NM_009855.2, Mus musculus CD80 antigen (Cd80), mRNA; ROD Apr. 27, 2014.
Genbank Accession No. NM_011617.2, Mus musculus CD70 antigen (Cd70), mRNA; Feb. 26, 2014.
Genbank Accession No. NM_015259.4; *Homo sapiens* inducible T-cell co-stimulator ligand (ICOSLG), mRNA; PRI Sep. 2, 2013.

(56) References Cited

OTHER PUBLICATIONS

Genbank Accession No. NM_015790.3, Mus musculus icos ligand (Icosl), mRNA; ROD Mar. 30, 2014.
Genbank Accession No. NM_019388.3, Mus musculus CD86 antigen (Cd86), mRNA; ROD May 18, 2014.
Genbank Accession No. NP_001243.1, CD70 antigen [Homo sapiens]; PRI May 11, 2014.
Genbank Accession No. NP_003317.1, tumor necrosis factor ligand superfamily member 4 isoform 1 [Homo sapiens]; PRI Jul. 4, 2014.
Genbank Accession No. NP_003802.1, tumor necrosis factor ligand superfamily member 9 [Homo sapiens]; PRI May 10, 2014.
Genbank Accession No. NP_005182.1, T-lymphocyte activation antigen CD80 precursor [Homo sapiens]; PRI May 18, 2014.
Genbank Accession No. NP_0056074.1; ICOS ligand isoform a precursor [Homo sapiens]; PRI Feb. 13, 2014.
Genbank Accession No. NP_033430.1, tumor necrosis factor ligand superfamily member 9 [Mus musculus]; ROD May 18, 2014.
Genbank Accession No. NP_033478.1, tumor necrosis factor ligand superfamily member 4 [Mus musculus]; ROD May 26, 2014.
Genbank Accession No. NP_033985.3, T-lymphocyte activation antigen CD80 precursor [Mus musculus]; ROD Apr. 27, 2014.
Genbank Accession No. NP_056605.1, ICOS ligand precursor [Mus musculus]; ROD Mar. 30, 2014.
Genbank Accession No. NP_056606.1, F-box only protein 8 [Mus musculus]; ROD Apr. 8, 2003.
Genbank Accession No. NP_062261.3, T-lymphocyte activation antigen CD86 precursor [Mus musculus]; ROD May 18, 2014.
Ghaneh et al., "Adenovirus-mediated transfer of p53 and p16(INK4a) results in pancreatic cancer regression in vitro and in vivo," Gene Ther. 8(3):199-208 (2001).
Guo et al., "Oncolytic Immunotherapy: Dying the Right Way is a Key to Eliciting Potent Antitumor Immunity," Front. Oncol. 4:74 (2014) (eCollection 2014).
Hemminki, "Oncolytic Immunotherapy: Where Are We Clinically?" Scientifica (Cairo) 2014:862925 (2014).
Herber et al., "Squamous epithelial hyperplasia and carcinoma in mice transgenic for the human papillomavirus type 16 E7 oncogene," J. Virol. 70(3):1873-1881 (1996).
Hirschhorn-Cymerman et al., "Induction of tumoricidal function in CD4+ T cells is associated with concomitant memory and terminally differentiated phenotype," J. Exp. Med. 209(11):2113-2126.
Hollinger et al., "Engineered antibody fragments and the rise of single domains." Nat. Biotechnol. 23(9): 1126-1136 (2005).
Hosokawa et al., "In vivo analysis of mammary and non-mammary tumorigenesis in MMTV-cyclin D1 transgenic mice deficient in p53," Transgenic Res. 10(5):471-478 (2001).
Hotte et al., "An optimized clinical regimen for the oncolytic virus PV701," Clin. Cancer Res. 13(3):977-985 (2007).
Hough et al., "A model for spontaneous B-lineage lymphomas in IgHmu-HOX11 transgenic mice," Proc. Natl. Acad. Sci. USA 95(23):13853-13858 (1998).
Huang et al. "Newcastle disease virus V protein is associated with viral pathogenesis and functions as an alpha interferon antagonist," J. Virol. 77(16):8676-8685 (2003).
Huard et al., "CD4/major histocompatibility complex class II interaction analyzed with CD4- and lymphocyte activation gene-3 (LAG-3)-Ig fusion proteins," Eur. J. Immunol. 25(9):2718-2721 (1995).
International Search Report dated Aug. 15, 2014 from PCT/US14/20299.
International Search Report of International application No. PCT/US2010/023335, dated Jun. 7, 2010.
Iwai et al., "Involvement of PD-L1 on tumor cells in the escape from host immune system and tumor immunotherapy by PD-L1 blockade," Proc. Natl. Acad. Sci. USA 99(19):12293-12297 (2002).
Kado et al., "Intestinal microflora are necessary for development of spontaneous adenocarcinoma of the large intestine in T-cell receptor beta chain and p53 double-knockout mice," Cancer Res. 61(6):2395-2398 (2001).

Kato et al., "Cell type-specific involvement of RIG-I in antiviral response," Immunity 23(1):19-28 (2005).
Khattar et al., "A Y526Q mutation in the Newcastle disease virus HN protein reduces its functional activities and attenuates virus replication and pathogenicity," J. Virol. 83(15):7779-7782 (2009).
Kim et al., "Expression and characterization of a recombinant Fab fragment derived from an anti-human alpha-fetoprotein monoclonal antibody," Mol. Cells. 11(2):158-163 (2001).
Krishnamurthy et al., "Differentially regulated interferon response determines the outcome of Newcastle disease virus infection in normal and tumor cell lines," J. Virol. 80(11):5145-5155 (2006).
Kuraguchi et al., "Tumor-associated Apc mutations in M1h1-/-Apc1638N mice reveal a mutational signature of M1h1 deficiency," Oncogene 19(50):5755-5763 (2000).
Lamb and Kolakofsky, 1996, Paramyxoviridae: The Viruses and Their Replication. In B.N. Fields, D.M. Knipe, & P.M. Howley (Eds.), Fundamental Virology:577-605, Philadelphia, PA.
Leach et al., "Enhancement of antitumor immunity by CTLA-4 blockade," Science 271(5256):1734-1736 (1996).
Lei et al., "An oncolytic adenovirus expressing granulocyte macrophage colony-stimulating factor shows improved specificity and efficacy for treating human solid tumors," Cancer Gene Ther. 16(1):33-43 (2009).
Li et al., "Therapeutic effects of a fusogenic Newcastle disease virus in treating head and neck cancer," Head Neck 33(10):1394-1399 (2011).
Liu et al., "ICP34.5 deleted herpes simplex virus with enhanced oncolytic, immune stimulating, and anti-tumour properties," Gene Ther. 10(4):292-303 (2003).
Liu et al., "Adenovirus-mediated intratumoral expression of immunostimulatory proteins in combination with systemic Treg inactivation induces tumor-destructive immune responses in mouse models," Cancer Gene Ther. 18(6):407-418 (2011).
Lorence et al., "Phase 1 clinical experience using intravenous administration of PV701, an oncolytic Newcastle disease virus," Curr. Cancer Drug Targets 7(2):157-167 (2007).
Maeda et al., "Live bivalent vaccine for parainfluenza and influenza virus infections," J. Virol. 79(11):6674-6679 (2005).
Mansour et al., "Oncolytic specificity of newcastle disease virus is mediated by selectivity for apoptosis-resistant cells," J. Virol. 85(12):6015-6023 (2011).
Meseck et al., "A Functional recombinant human 4-1BB ligand for immune costimulatory therapy of cancer," J. Immunother. 34:175-182 (2011).
Morris et al., "Lung-specific expression in mice of a dominant negative mutant form of the p53 tumor suppressor protein," J. La. State Med. Soc. 150(4):179-185 (1998).
Muranski et al., "Tumor-specific Th17-polarized cells eradicate large established melanoma," Blood 112(2):362-373 (2008).
Murawski et al., "Newcastle disease virus-like particles containing respiratory syncytial virus G protein induced protection in BALB/c mice, with no evidence of immunopathology," J Virol. 84(2):1110-1123 (2010).
Nakaya et al., "Recombinant Newcastle disease virus as a vaccine vector," J. Virol. 75(23):11868-11873 (2001).
Office Action dated Jul. 26, 2016 of U.S. Appl. No. 14/774,962.
Overwijk et al., "Tumor regression and autoimmunity after reversal of a functionally tolerant state of self-reactive CD8+ T cells," J. Exp. Med. 198(4):568-580 (2003).
Park et al., "Newcastle disease virus V protein is a determinant of host range restriction," J. Virol. 77(17):9522-9532 (2003).
Park et al., "Engineered viral vaccine constructs with dual specificity: avian influenza and Newcastle disease," Proc. Natl. Acad. Sci. USA 103(21):8203-8208 (2006).
Pecora et al., "Phase I trial of intravenous administration of PV701, an oncolytic virus, in patients with advanced solid cancers," J. Clin. Oncol. 20(9):2251-2266 (2002).
Peeters et al., "Rescue of Newcastle disease virus from cloned cDNA: evidence that cleavability of the fusion protein is a major determinant for virulence," J. Virol. 73(6):5001-5009 (1999).

(56) References Cited

OTHER PUBLICATIONS

Peeters et al., "Generation of a recombinant chimeric Newcastle disease virus vaccine that allows serological differentiation between vaccinated and infected animals," Vaccine 19(13-14):1616-1627 (2001).
Phuangsab et al., "Newcastle disease virus therapy of human tumor xenografts: antitumor effects of local or systemic administration," Cancer Lett. 172(1):27-36 (2001).
Plitt and Zamarin, "Cancer therapy with Newcastle disease virus: rationale for new immunotherapeutic combinations," Clin. Invest. (Lond.) 5(1):75-87 (2015).
Pühler et al., "Generation of a recombinant oncolytic Newcastle disease virus and expression of a full IgG antibody from two transgenes," Gene Ther. 15(5):371-383 (2008) (Epub Jan. 17, 2008).
Quezada et al., "CTLA4 blockade and GM-CSF combination immunotherapy alters the intratumor balance of effector and regulatory T cells," J. Clin. Invest. 116(7):1935-1945 (2006).
Robert et al., "Ipilimumab plus dacarbazine for previously untreated metastatic melanoma," N. Engl. J. Med. 364(26):2517-2526 (2011).
Schirrmacher et al., "Antitumor effects of Newcastle Disease Virus in vivo: Local versus systemic effects," Int. J. Oncol. 18:945-952 (2001).
Schirrmacher et al., "Newcastle disease virus: a promising vector for viral therapy, immune therapy, and gene therapy of cancer," Methods Mol. Biol. 542:565-605 (2009).
Seliger et al., "Characterization of the major histocompatibility complex class I deficiencies in B16 melanoma cells," Cancer Res. 61(3):1095-1099 (2001).
Seppi et al., "Direct determination of oxygen by HPLC. 2. Chamber and sample application system for determination of o(2) at trace levels," Anal Chem. 69(21):4476-4481 (1997).
Sharma et al., "Triggering the interferon antiviral response through an ikk-related pathway," Science 300(5622):1148-1151 (2003).
Shenk, 1996, Adenoviridae: The Viruses and Their Replication. In B.N. Fields, D.M. Knipe, & P.M. Howley (Eds.), Fundamental Virology (pp. 978-1016). Philadelphia, PA: Lippincott-Raven.
Silberhumer et al., "Genetically engineered oncolytic Newcastle disease virus effectively induces sustained remission of malignant pleural mesothelioma," Mol. Cancer Ther. 9(10):2761-2769 (2010).
Simpson et al., "Regulation of CD4 T cell activation and effector function by inducible costimulator (ICOS)," Curr. Opin. Immunol. 22(3):326-332 (2010).
Sinkovics and Horvath, "Newcastle disease virus (NDV): brief history of its oncolytic strains," J. Clin. Virol. 16(1):1-15 (2000).
Song et al., "Antitumor efficacy of viral therapy using genetically engineered Newcastle disease virus [NDV(F3aa)-GFP] for peritoneally disseminated gastric cancer," J. Mol. Med. (Berl). 88(6):589-596 (2010).
Spranger et al., "Up-regulation of PD-L1, IDO, and T(regs) in the melanoma tumor microenvironment is driven by CD8(+) T cells," Sci. Transl. Med. 5(200):200ra116 (2013).
Swann et al., "Type I IFN contributes to NK cell homeostasis, activation, and antitumor function," J. Immunol. 178(12):7540-7549 (2007).
Swayne et al., "Recombinant paramyxovirus type 1-avian influenza-H7 virus as a vaccine for protection of chickens against influenza and Newcastle disease," Avian Dis. 47(3 Suppl):1047-1050 (2003).
Topalian et al., "Safety, activity, and immune correlates of anti-PD-1 antibody in cancer," N. Engl. J. Med. 366(26):2443-2454 (2012) (Epub Jun. 2, 2012).
Tuve et al., "In situ adenovirus vaccination engages T effector cells against cancer," Vaccine 27(31):4225-4239 (2009).
Vail and Macewen, "Spontaneously occurring tumors of companion animals as models for human cancer," Cancer Invest. 18(8):781-792 (2000).
Vigil et al., "Use of reverse genetics to enhance the oncolytic properties of Newcastle disease virus," Cancer Res. 67(17):8285-8292 (2007).
Vigil et al., "Recombinant Newcastle disease virus as a vaccine vector for cancer therapy," Mol. Ther. 16(11):1883-1890 (2008).
Waitz et al., "Potent induction of tumor immunity by combining tumor cryoablation with anti-CTLA-4 therapy," Cancer Res. 72(2):430-439 (2012).
Wakamatsu et al., "Convergent and divergent effects of costimulatory molecules in conventional and regulatory CD4+ T cells," Proc. Natl. Acad. Sci .USA 110(3):1023-1028 (2013).
Walter et al., "Targeted Inhibition of Interferon-γ-dependent Intercellular Adhesion Molecule-1 (ICAM-1) Expression Using Dominant-Negative Stat1," J. Biol. Chem. 272(45):28582-28589 (1997).
Walter et al., "Two avirulent, lentogenic strains of Newcastle disease virus are cytotoxic for some human pancreatic tumor lines in vitro," JOP 13(5):502-513 (2012).
Wang et al., "A novel, clinically relevant animal model of metastatic pancreatic adenocarcinoma biology and therapy," Int. J. Pancreatol. 29(1):37-46 (2001).
Weber et al., "Viral suppression of the interferon system," Biochimie 89(6-7):836-842 (2007).
Wilden et al., "Expression of RIG-I, IRF3, IFN-beta and IRF7 determines resistance or susceptibility of cells to infection by Newcastle Disease Virus," Int. J. Oncol. 34(4):971-982 (2009).
Woller et al., "Oncolytic viruses as anticancer vaccines," Front. Oncol. 4:188 (2014) (eCollection 2014).
Written Opinion dated Jul. 19, 2014 from PCT/US14/20299.
Written Opinion of International application No. PCT/US2010/023335, dated Jun. 7, 2010.
Ying et al., "Adenovirus-mediated intratumoral expression of immunostimulatory proteins in combination with systemic Treg inactivation induces tumor-destructive immune responses in mouse models," Cancer Gene Ther. 18(6):407-418 (2011).
Yoneyama et al., "The RNA helicase RIG-I has an essential function in double-stranded RNA-induced innate antiviral responses," Nat. Immunol. 5:730-737 (2004).
Zamarin and Palese, "Oncolytic Newcastle disease virus for cancer therapy: old challenges and new directions," Future Microbiol. 7(3):347-367 (2012).
Zamarin and Wolchok, "Potentiation of immunomodulatory antibody therapy with oncolytic viruses for treatment of cancer," Mol. Ther. Oncolytics 1:14004 (2014).
Zamarin et al., "Genetically engineered Newcastle disease virus for malignant melanoma therapy," Gene Ther. 16(6):796-804 (2009).
Zamarin et al., "Enhancement of oncolytic properties of recombinant Newcastle disease virus through antagonism of cellular innate immune responses," Mol. Ther. 17(4):697-706 (2009).
Zamarin et al., "Localized oncolytic virotherapy overcomes systemic tumor resistance to immune checkpoint blockade immunotherapy," Sci. Transl. Med. 6(226):226ra32 (2014).
Zhang and Roth, "Anti-oncogene and tumor suppressor gene therapy—examples from a lung cancer animal model," In Vivo 8(5):755-769 (1994).
Zimmer et al., "A chimeric respiratory syncytial virus fusion protein functionally replaces the F and HN glycoproteins in recombinant Sendai virus," J. Virol. 79(16):10467-10477 (2005).
Aigner et al., "An effective tumor vaccine optimized for costimulation via bispecific and trispecific fusion proteins," Int. J. Oncol. 32(4):777-789 (2008).
Ayers et al., "IFN-γ-related mRNA profile predicts clinical response to PD-1 blockade," J. Clin. Invest. 127(8):2930-2940 (2017).
Ayllon et al., "Rescue of Recombinant Newcastle Disease Virus from cDNA," J. Vis. Exp. 80:e50830 (2013).
Buijs et al., "Recombinant Immunomodulating Lentogenic or Mesogenic Oncolytic Newcastle Disease Virus for Treatment of Pancreatic Adenocarcinoma," Viruses 7(6):2980-2998 (2015).
Cheng et al., "Genetic Modification of Oncolytic Newcastle Disease Virus for Cancer Therapy," J. Virol. 90(1):5343-5352 (2016).
Fu et al., "The ICOS/ICOSL Pathay is Required for Optimal Antitumor Responses Mediated by Anti-CTLA-4 Therapy," Cancer Res. 71(16):5445-5454 (2011).
GenBank Accession No. JF950510.1, Newcastle disease virus strain LaSota, complete genome, dated Aug. 10, 2011.
GenBank Accession No. M11220.1, Human granulocyte-macrophage colony stimulating factor (GM-CSF) mRNA, dated Nov. 8, 1994.

(56) References Cited

OTHER PUBLICATIONS

GenBank Accession No. NM_000586.3, *Homo sapiens* interleukin 2 (IL2), mRNA, dated Oct. 16, 2017.
Goff et al., "A majority of infectious Newcastle disease virus particles contain a single genome, while a minority contain multiple genomes," J. Virol. 86(19):10852-10856 (2012).
Haas et al., "Bispecific antibodies increase T-cell stimulatory capacity in vitro of human autologous virus-modified tumor vaccine," Clin. Cancer Res. 4(3):721-730 (1998).
Haas et al., "An effective strategy of human tumor vaccine modification by coupling bispecific costimulatory molecules," Cancer Gene Ther. 6(3):254-262 (1999).
Haas et al., "A tumor vaccine containing anti-CD3 and anti-CD28 bispecific antibodies triggers strong and durable antitumor activity in human lymphocytes," Int. J. Cancer 188(3):658-667 (2006).
Hamid et al., "Safety and Tumor Responses with Lambrolizumab (Anti-PD-1) in Melanoma," N. Engl. J. Med. 369(2):134-144 (2013).
Houdebine, "Production of Pharmaceutical Proteins by Transgenic Animals," Comp. Immunol. Microbiol. Infect. Dis. 32(2):107-121 (2009).
International Nonproprietary Names for Pharmaceutical Substances (INN), WHO Drug Information, vol. 27, No. 2, 2013, List 109.
International Search Report dated Mar. 28, 2007 of International application No. PCT/US06/45859.
Jones and Vignali, "Molecular interactions within the IL-6/IL-12 cytokine/receptor superfamily," Immunol. Res. 51(1):5-14 (2011).
Peggs et al., "Cancer immunotherapy: co-stimulatory agonists and co-inhibitory antagonists," Clin. Immunol. 157(1):9-19 (2009).
Ravindra et al., "Newcastle disease virus as an oncolytic agent," Indian J. Med. Res. 130(5):507-513 (2009).
Ren et al., "Recombinant Newcastle Disease Virus Encoding IL-12 and/or IL-2 as Potential Candidate for Hepatoma Carcinoma Therapy," Technol. Cancer Res. Treat. 15(5):NP83-NP94 (2016).
Schickli et al., "Plasmid-only rescue of influenza A virus vaccine candidates," Philos. Trans. R. Soc. Lond. B Biol. Sci. 356(1416):1965-1973 (2001).
Sergel et al., "A Single Amino Acid Change in the Newcastle Disease Virus Fusion Protein Alters the Requirement for HN Protein in Fusion," J. Virol. 74(11):5101-5107 (2000).
Su et al., "Immunoadjuvant activities of a recombinant chicken IL-12 in chickens vaccinated with Newcastle disease virus recombinant HN protein," Vet. Microbiol. 151(3-4):220-228 (2011).
Turk et al., "Concomitant tumor immunity to a poorly immunogenic melanoma is prevented by regulatory T cells," J. Exp. Med. 200(6):771-782 (2004).
U.S. Appl. No. 14/205,776; Amendment dated Jan. 8, 2016.
U.S. Appl. No. 14/205,776; Amendment under 37 C.F.R. 1.111 dated Jun. 9, 2015.
U.S. Appl. No. 14/205,776; Final Office Action dated Aug. 10, 2015.
U.S. Appl. No. 14/205,776; Non-Final Office Action dated Jan. 28, 2015.
U.S. Appl. No. 14/205,776; Requirement for Restriction/Election dated Nov. 13, 2014.
U.S. Appl. No. 14/205,776; Response to Restriction Requirement and Preliminary Amendment dated Jan. 13, 2015.
Verma et al., "Gene therapy—promises, problems and prospects," Nature 389(6648):239-242 (1997).
Vlasak et al., "Use of flow cytometry for characterization of human cytomegalovirus vaccine particles," Vaccine 34(20):2321-2328 (2016).
Written Opinion dated Mar. 28, 2007 of International application No. PCT/US06/45859.
Yamaki et al., "The potential of recombinant vesicular stomatitis virus-mediated virotherapy against metastatic colon cancer," Int. J. Mol. Med. 2013 31(2):299-306 (2013).
Zamarin et al., "PD-L1 in tumor microenvironment mediates resistance to oncolytic immunotherapy," J. Clin. Invest. 128(4):1413-1428 (2018).
Zitvogel et al., "Type I interferons in anticancer immunity", Nat. Rev. Immunol. 15(7):405-414 (2015).

Annels et al., "Oncolytic Immunotherapy for Bladder Cancer Using Coxsackie A21 Virus," Mol. Ther. Oncolytics 9:1-12 (2018).
Assudani et al., "Immunotherapeutic potential of DISC-HSV and OX40L in cancer," Cancer Immunol. Immunother. 55:104-111 (2006).
Barber et al. "Restoring function in exhausted CD8 T cells during chronic viral infection," Nature 439:682-687 (2006); (Supplemental Material attached, 7 pages).
Blackburn et al., "Tissue-specific differences in PD-1 and PD-L1 expression during chronic viral infection: implications for CD8 T-cell exhaustion," J. Virol. 84(4):2078-2089 (2010) (Epub Dec. 2, 2009).
Blake et al., "Automated kinetic exclusion assays to quantify protein binding interactions in homogeneous solution," Anal. Biochem. 272(2):123-134 (1999).
Brahmer et al., "Phase I study of single-agent anti-programmed death-1 (MDX-1106) in refractory solid tumors: safety, clinical activity, pharmacodynamics, and immunologic correlates," J. Clin. Oncol. 28(19):3167-3175 (2010).
Brown et al., "Role of PD-1 in regulating acute infections," Curr. Opin. Immunol. 22(3):397-401 (2010).
Car et al., "The Toxicology of Interleukin-12: A Review," Toxicol. Pathol. 27(1):58-63 (1999).
Caruso et al., "Adenovirus-mediated interleukin-12 gene therapy for metastatic colon carcinoma," Proc. Natl. Acad. Sci. USA 93:11302-11306 (1996).
Chen et al., "CD4 T Cells Require ICOS-Mediated P13K Signaling to Increase T-Bet Expression in the Setting of Anti-CTLA-4 Therapy," Cancer Immunol. Res. 2(2):167-176 (2013).
Chumakov et al., "Oncolytic Enteroviruses," Mol. Biol. (Mosk) 46(5):639-650 (2012).
Clinical Trial NCT01295827, "Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001) (KEYNOTE-001)," Merck Sharp & Dohme Corp., updated Sep. 13, 2018 (13 pages).
Cull et al., "Screening for receptor ligands using large libraries of peptides linked to the C terminus of the lac repressor," Proc. Natl. Acad. Sci. USA 89(5):1865-1869 (1992).
Cwirla et al., "Peptides on phage: a vast library of peptides for identifying ligands," Proc. Natl. Acad. Sci. USA 87(16):6378-6382 (1990).
De Sousa Linhares et al., "Not All Immune Checkpoints Are Created Equal," Front. Immunol. 9:1909 (2018).
Dortmans et al., "Virulence of Newcastle disease virus: what is known so far?" Vet. Res. 42:122 (2011).
Douin-Echinard et al., "Enhancement of anti-tumor immunity by injection of fibroblasts genetically engineered to produce IL-12 and to express CD70," Gene Therapy of Cancer, edited by Walden et al., Plenum Press, New York, 353-357 (1998).
Fan et al., "Engagement of the ICOS pathway markedly enhances efficacy of CTLA-4 blockade in cancer immunotherapy," J. Exp. Med. 211(4):715-725 (2014).
Felici et al., "Selection of antibody ligands from a large library of oligopeptides expressed on a multivalent exposition vector," J. Mol. Biol. 222(2):301-310 (1991).
Fields et al., Fundamental Virology, 2$^{nd}$ Edition, Raven Press, 1991, Chapter 31, "Adenoviridae and Their Replication," pp. 771-813.
Fodor et al., "Multiplexed biochemical assays with biological chips," Nature 364(6437):555-556 (1993).
Gambotto et al., "Induction of antitumor immunity by direct intratumoral injection of a recombinant adenovirus vector expressing interleukin-12," Cancer Gene Ther. 6(1):45-53 (1999).
Gardiner et al., "A Randomized, Double-Blind, Placebo-Controlled Assessment of BMS-936558, a Fully Human Monoclonal Antibody to Programmed Death-1 (PD-1), in Patients with Chronic Hepatitis C Virus Infection," PLoS One 8(5):e63818 (2013).
Genbank Accession No. AAS67141.1; fusion protein [Avian avulavirus 1]; Mar. 22, 2004.
Genbank Accession No. AAS67147.1; fusion protein [Avian avulavirus 1]; Mar. 22, 2004.
Genbank Accession No. AAS67153.1; fusion protein [Avian avulavirus 1]; Mar. 22, 2004.

(56) References Cited

OTHER PUBLICATIONS

Genbank Accession No. AAS67159.1; fusion protein [Avian avulavirus 1]; Mar. 22, 2004.
Genbank Accession No. AAS67165.1; fusion protein [Avian avulavirus 1]; Mar. 22, 2004.
Genbank Accession No. ACJ53752.1; fusion protein [Avian avulavirus 1]; Nov. 25, 2008.
Genbank Accession No. ACJ53758.1; fusion protein [Avian avulavirus 1]; Nov. 25, 2008.
Genbank Accession No. ACK57498.1; fusion protein [Avian avulavirus 1]; Apr. 19, 2011.
Genbank Accession No. ADF59234.1; fusion protein [Avian avulavirus 1]; Aug. 16, 2011.
Genbank Accession No. AIA66858.1; NBS-LRR resistance protein, partial [Solanum viarum]; Jun. 4, 2014.
Genbank Accession No. AIA66951.1; fusion protein [Avian avulavirus 1]; Jun. 4, 2014.
Herbst et al., "Predictive correlates of response to the anti-PD-L1 antibody MPDL3280A in cancer patients," Nature 515(7528):563-567 (2014).
Hofmeyer et al., "The PD-1/PD-L1 (B7-H1) Pathway in Chronic Infection-Induced Cytotoxic T Lymphocyte Exhaustion," J. Biomed. Biotechnol. 2011:451694 (2011).
Hou et al., "Study on the effect of Newcastle disease virus vaccine and interleukin-12 to the tranjsplantable nude mice model of human ovarian cancer," Chin. J. Cancer Prev. Treat. 16(18):1375-1378 (2009).
Houghten et al. "The use of synthetic peptide combinatorial libraries for the identification of bioactive peptides," Biotechniques 13(3):412-421 (1992).
Huang et al., "Preclinical validation: LV/IL-12 transduction of patient leukemia cells for immunotherapy of AML," Mol. Ther. Methods Clin. Dev. 3:16074 (2016) (eCollection 2016).
Iwai et al., "PD-1 Inhibits Antiviral Immunity at the Effector Phase in the Liver," J. Exp. Med. 198(1):39-50 (2003).
Kamphorst et al., "Rescue of exhausted CD8 T cells by PD-1-targeted therapies is CD28-dependent," Science 355(6332):1423-1427 (2017).
Keytruda Highlights of Prescribing Information, revised Aug. 2018.
Keytruda Highlights of Prescribing Information, revised Oct. 2016.
Lam et al., "A new type of synthetic peptide library for identifying ligand-binding activity," Nature 354(6348):82-84 (1991).
Lee et al., "Isolation of cDNA for a human granulocyte-macrophage colony-stimulating factor by functional expression in mammalian cells," Proc. Natl. Acad. Sci. USA. 82(13):4360-4364 (1985).
Leonard et al., "Effects of single-dose interleukin-12 exposure on interleukin-12-associated toxicity and interferon-gamma production," Blood 90(7):2541-2548 (1997).
Lieschke et al., "Bioactive murine and human interleukin-12 fusion proteins which retain antitumor activity in vivo," Nat. Biotechnol. 15(1):35-40 (1997).
Lotze et al., "Cytokine Gene Therapy of Cancer Using Interleukin-12: Murine and Clinical Trials," Ann. N.Y. Acad. Sci. 795:440-454 (1995).
Mazzolini et al., "Adenoviral Gene Transfer of Interleukin 12 into Tumors Synergizes with Adoptive T Cell Therapy Both at the Induction and Effector Level," Human Gene Ther. 11:113-125 (2000).
Mazzolini et al., "Regression of colon cancer and induction of antitumor immunity by intratumoral injection of adenovirus expressing interleukin-12," Cancer Gene Ther. 6(6):514-522 (1999).
Niu et al., "Recombinant Newcastle Disease virus Expressing IL15 Demonstrates Promising Antitumor Efficiency in Melanoma Model," Technology in Cancer Research and Treatment 14(5):607-615 (2015).
Oseledchyk et al., "Lysis-independent potentiation of immune checkpoint blockade by oncolytic virus," Oncotarget 9(47):28702-28716 (2018).
Oseledchyk et al., "Lysis-independent potentiation of immune checkpoint blockade by oncolytic virus," Oncotarget 9(47):28702-28716 (2018) Supplementary Materials (2 pages).
Pardoll, "The blockade of immune checkpoints in cancer immunotherapy," Nat. Rev. Cancer 12(4):252-264 (2012).
Puzanov et al., "Phase 1 results of a phase 1b/2, multicenter, open-label trial to evaluate safety and efficacy of talimogene laherparepvec (T-VEC) and ipilimumab (ipi) vs ipi alone in previously untreated, unresected stage IIIb-IV melanoma," J. Immunother. Cancer 1(Suppl 1):P84 (2013).
Quetglas et al., "Virotherapy with a Semliki Forest Virus-Based Vector Encoding IL12 Synergizes with PD-1/PD-L1 Blockade," Cancer Immunol. Res. 3(5):449-454 (2015).
Quinn and Trevor, "Rapid quantitation of recombinant retrovirus produced by packaging cell clones," Biotechniques. 23(6):1038-1044 (1997).
Ribas et al., "Oncolytic Virotherapy Promotes Intratumoral T Cell Infiltration and Improves Anti-PD-1 Immunotherapy," Cell 170(6):1109-1119 (2017).
Robbins and Kawakami, "Human tumor antigens recognized by T cells," Curr. Opin. Immunol. 8(5):628-636 (1996).
Scott and Smith, "Searching for peptide ligands with an epitope library," Science. 249(4967):386-390 (1990).
Shim et al., "Inhibitory Receptors Induced by VSV Viroimmunotherapy Are Not Necessarily Targets for Improving Treatment Efficacy," Mol. Ther. 25(4):962-975 (2017).
Tumeh et al., "PD-1 blockade induces responses by inhibiting adaptive immune resistance," Nature 515(7528):568-571 (2014); (attached Extended Data Figures 1-6 and Extended Data Tables 1-4 attached).
United States Patent and Trademark Office Final Office Action dated Sep. 23, 2016, for U.S. Appl. No. 14/205,776 (19 pages).
United States Patent and Trademark Office Final Office Action dated Aug. 10, 2015, for U.S. Appl. No. 14/205,776 (22 pages).
United States Patent and Trademark Office Non-Final Office Action dated Nov. 9, 2016, for U.S. Appl. No. 14/774,962 (15 pages).
United States Patent and Trademark Office Non-Final Office Action dated Jul. 16, 2018, for U.S. Appl. No. 15/588,251 (17 pages).
United States Patent and Trademark Office Non-Final Office Action dated Mar. 4, 2016, for U.S. Appl. No. 14/205,776 (19 pages).
United States Patent and Trademark Office Non-Final Office Action dated Jan. 28, 2015, for U.S. Appl. No. 14/205,776 (14 pages).
United States Patent and Trademark Office Requirement for Restriction/Election dated Sep. 5, 2018, for U.S. Appl. No. 15/789,340 (6 pages).
Velu et at, "Role of PD-1 co-inhibitory pathway in HIV infection and potential therapeutic options," Retrovirology 12:14 (2015).
Wakamatsu et al., "The effect on pathogenesis of Newcastle disease virus LaSota strain from a mutation of the fusion cleavage site to a virulent sequence," Avian Dis. 50(4):483-488 (2006).
Wold and Toth, "Adenovirus vectors for gene therapy, vaccination and cancer gene therapy," Curr. Gene Ther. 13(6):421-433 (2013).
Yao and Chen, "Reviving exhausted T lymphocytes during chronic virus infection by B7-H1 blockade," Trends Mol. Med. 12(6):244-246 (2006).
Zamarin et al., "Intratumoral modulation of the inducible co-stimulator ICOS by recombinant oncolytic virus promotes systemic anti-tumour immunity," Nat. Commun. 8:14340 (2017).
Zamarin et al., "Localized oncolytic virotherapy inflames distant tumors and synergizes with immune checkpoint blockade leading to systemic tumor rejection," J. Immunother. Cancer 1(Suppl 1):O9 (2013).
Zamarin et al., "PD-L1 in tumor microenvironment mediates resistance to oncolytic immunotherapy," J. Clin. Invest. 128(4):1413-1428 (2018); Supplemental Information (11 pages).
Zamarin et al., "Upregulation of PD-L1 in tumor microenvironment is a resistance mechanism for onolytic virus immunotherapy," J. Immunother. Cancer 5(Suppl 2):87 (2017).
Zamarin et al., 2008, "Enhancement of Oncolytic Properties of Genetically-Engineered Fusogenic Newcastle Disease Virus through Antagonism of Cellular Innate Immune Responses," Mol. Ther. 16(Suppl. 1), Abstract #43.
Zamarin et al., "Localized oncolytic virotherapy overcomes systemic tumor resistance to immune checkpoint blockade immunotherapy," Sci. Transl. Med. 6(226):226ra32 (2014); Supplemental Material, Figures and Tables (96 pages).

(56) References Cited

OTHER PUBLICATIONS

Li et al., "Decreased dependence on receptor recognition for the fusion promotion activity of L289A-mutated newcastle disease virus fusion protein correlates with a monoclonal antibody-detected conformational change," J. Virol. 79(2):1180-1190 (2005).

Zhao et al., "P and M gene junction is the optimal insertion site in Newcastle disease virus vaccine vector for foreign gene expression," J. Gen. Virol. 96(Pt 1):40-45 (2015) (Epub Oct. 1, 2014).

\* cited by examiner

A

NEWCASTLE DISEASE VIRUSES AND USES THEREOF

This application is a divisional of U.S. patent application Ser. No. 14/205,776, filed Mar. 12, 2014, which claims priority to U.S. Provisional Application No. 61/782,994, filed on Mar. 14, 2013, each of which is incorporated by reference herein in its entirety.

This invention was made with government support under T32 CA009207 and HHSN26620070010C awarded by the National Institutes of Health. The government has certain rights in the invention.

1. INTRODUCTION

Described herein are chimeric Newcastle disease viruses engineered to express an agonist of a co-stimulatory signal of an immune cell and compositions comprising such viruses. Also described herein are chimeric Newcastle disease viruses engineered to express an antagonist of an inhibitory signal of an immune cell and compositions comprising such viruses. The chimeric Newcastle disease viruses and compositions are useful in the treatment of cancer. In addition, described herein are methods for treating cancer comprising administering Newcastle disease viruses in combination with an agonist of a co-stimulatory signal of an immune cell and/or an antagonist of an inhibitory signal of an immune cell.

2. BACKGROUND

Newcastle Disease Virus (NDV) is a member of the *Avulavirus* genus in the Paramyxoviridae family, which has been shown to infect a number of avian species (Alexander, D J (1988). Newcastle disease, Newcastle disease virus—an avian paramyxovirus. Kluwer Academic Publishers: Dordrecht, The Netherlands. pp 1-22). NDV possesses a single-stranded RNA genome in negative sense and does not undergo recombination with the host genome or with other viruses (Alexander, D J (1988). Newcastle disease, Newcastle disease virus—an avian paramyxovirus. Kluwer Academic Publishers: Dordrecht, The Netherlands. pp 1-22). The genomic RNA contains genes in the order of 3'-NP-P-M-F-HN-L-5', described in further detail below. Two additional proteins, V and W, are produced by NDV from the P gene by alternative mRNAs that are generated by RNA editing. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrudes from the envelope allowing the virus to contain both hemagglutinin (e.g., receptor binding/fusogenic) and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication. The V protein has been shown to inhibit interferon-alpha and to contribute to the virulence of NDV (Huang et al. (2003). Newcastle disease virus V protein is associated with viral pathogenesis and functions as an Alpha Interferon Antagonist. *Journal of Virology* 77: 8676-8685).

Naturally-occurring NDV has been reported to be an effective oncolytic agent in a variety of animal tumor models (Sinkovics, J G, and Horvath, J C (2000). Newcastle disease virus (NDV): brief history of its oncolytic strains. *J Clin Virol* 16: 1-15). Naturally-occurring strains of NDV have been used in multiple clinical trials against advanced human cancers (Sinkovics, J G, and Horvath, J C (2000). Newcastle disease virus (NDV): brief history of its oncolytic strains. *J Clin Virol* 16: 1-15; Lorence et al. (2007). Phase 1 clinical experience using intravenous administration of PV701, an oncolytic Newcastle disease virus. *Curr Cancer Drug Targets* 7: 157-167; Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. *Mol Ther* 13: 221-228; Pecora et al. (2002). Phase I trial of intravenous administration of PV701, an oncolytic virus, in patients with advanced solid cancers. *J Clin Oncol* 20: 2251-2266; Csatary et al. (2004). MTH-68/H oncolytic viral treatment in human high-grade gliomas. *J Neurooncol* 67: 83-93). However, the success of naturally-occurring strains of NDV in these clinical trials for advanced human cancers was only marginal (Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. *Mol Ther* 13: 221-228; Pecora et al. (2002). Phase I trial of intravenous administration of PV701, an oncolytic virus, in patients with advanced solid cancers. *J Clin Oncol* 20: 2251-2266). As such, there remains a need for NDV-based therapies useful in the treatment of cancer, especially advanced cancer.

3. SUMMARY

In one aspect, presented herein are chimeric Newcastle disease viruses (NDVs) engineered to express an agonist of a co-stimulatory signal of an immune cell and/or an antagonist of an inhibitory signal of an immune cell. In a specific embodiment, presented herein are chimeric NDVs, comprising a packaged genome which encodes an agonist of a co-stimulatory signal of an immune cell, wherein the agonist is expressed. In a specific embodiment, presented herein are chimeric NDVs, comprising a packaged genome which encodes an antagonist of an inhibitory signal of an immune cell, wherein the antagonist is expressed.

In another embodiment, presented herein are chimeric NDVs, comprising a packaged genome which encodes an agonist of a co-stimulatory signal of an immune cell and a mutated F protein that causes the NDV to be highly fusogenic, wherein the agonist and the mutated F protein are expressed. In another embodiment, presented herein are chimeric NDVs, comprising a packaged genome which encodes an agonist of a co-stimulatory signal of an immune cell and a mutated F protein with a mutated cleavage site, wherein the agonist and the mutated F protein are expressed. In a specific embodiment, the chimeric NDVs expressing the mutated F protein have increased fusogenic activity relative to the corresponding virus expressing the counterpart F protein without the mutations to the cleavage site. In another specific embodiment, the modified F protein is incorporated into the virion.

In another embodiment, presented herein are chimeric NDVs, comprising a packaged genome which encodes an antagonist of an inhibitory signal of an immune cell and a mutated F protein that causes the NDV to be highly fusogenic, wherein the antagonist and the mutated F protein are expressed. In another embodiment, presented herein are chimeric NDVs, comprising a packaged genome which encodes antagonist of an inhibitory signal of an immune cell and a mutated F protein with a mutated cleavage site, wherein the antagonist and the mutated F protein are expressed. In a specific embodiment, the chimeric NDVs expressing the mutated F protein have increased fusogenic activity relative to the corresponding virus expressing the counterpart F protein without the mutations to the cleavage site. In another specific embodiment, the modified F protein is incorporated into the virion.

In another embodiment, presented herein are chimeric NDVs, comprising a packaged genome which encodes an agonist of a co-stimulatory signal of an immune cell and a cytokine (e.g., interleukin (IL)-2), wherein the agonist and the cytokine are expressed. In another embodiment, presented herein are chimeric NDVs, comprising a packaged genome which encodes an agonist of a co-stimulatory signal of an immune cell, a cytokine (e.g., IL-2) and a mutated F protein that causes the NDV to be highly fusogenic, wherein the agonist, the cytokine and the mutated F protein are expressed. In another embodiment, presented herein are chimeric NDVs, comprising a packaged genome which encodes an agonist of a co-stimulatory signal of an immune cell, a cytokine (e.g., IL-2) and a mutated F protein with a mutated cleavage site, wherein the agonist, the cytokine and the mutated F protein are expressed. In a specific embodiment, the chimeric NDVs expressing the mutated F protein with the mutated cleavage site are highly fusogenic. In another specific embodiment, the mutated F protein is incorporated into the virion.

In another embodiment, presented herein are chimeric NDVs, comprising a packaged genome which encodes an antagonist of an inhibitory signal of an immune cell of an immune cell and a cytokine (e.g., IL-2), wherein the antagonist and the cytokine are expressed. In another embodiment, presented herein are chimeric NDVs, comprising a packaged genome which encodes an antagonist of an inhibitory signal of an immune cell, a cytokine (e.g., IL-2) and a mutated F protein that causes the NDV to be highly fusogenic, wherein the antagonist, the cytokine and the mutated F protein are expressed. In another embodiment, presented herein are chimeric NDVs, comprising a packaged genome which encodes an antagonist of an inhibitory signal of an immune cell, a cytokine (e.g., IL-2) and a mutated F protein with a mutated cleavage site, wherein the antagonist, the cytokine and the mutated F protein are expressed. In a specific embodiment, the chimeric NDVs expressing the mutated F protein with the mutated cleavage site are highly fusogenic. In another specific embodiment, the mutated F protein is incorporated into the virion.

In a specific embodiment, the agonist of a co-stimulatory signal of an immune cell is an agonist of a co-stimulatory receptor expressed by an immune cell. Specific examples of co-stimulatory receptors include glucocorticoid-induced tumor necrosis factor receptor (GITR), Inducible T-cell costimulator (ICOS or CD278), OX40 (CD134), CD27, CD28, 4-1BB (CD137), and CD40. In a specific embodiment, the agonist of a co-stimulatory receptor expressed by an immune cell is an antibody (or an antigen-binding fragment thereof) or ligand that specifically binds to the co-stimulatory receptor. In one embodiment, the antibody is a monoclonal antibody. In another embodiment, the antibody is an sc-Fv. In a specific embodiment the antibody is a bispecific antibody that binds to two receptors on an immune cell. In one embodiment, the bispecific antibody binds to a receptor on an immune cell and to another receptor on a cancer cell. In specific embodiments, the antibody is a human or humanized antibody. In other embodiments, the ligand or an antibody is a chimeric protein comprising a NDV F protein or NDV HN protein. Methods for generating such chimeric proteins are known in the art. See, e.g., U.S. Patent Application Publication No. 2012-0122185, the disclosure of which is herein incorporated by reference in its entirety. Also see Park et al., PNAS 2006; 103:8203-8 and Murawski et al., J Virol 2010; 84:1110-23, the disclosures of which is herein incorporated by reference in their entireties.

In a specific embodiment, the antagonist of an inhibitory signal of an immune cell is an antagonist of an inhibitory receptor expressed by an immune cell. Specific examples of inhibitory receptors include cytotoxic T-lymphocyte-associated antigen 4 (CTLA-4 or CD52), programmed cell death protein 1 (PD1 or CD279), B and T-lymphocyte attenuator (BTLA), killer cell immunoglobulin-like receptor (KIR), lymphocyte activation gene 3 (LAG3), T-cell membrane protein 3 (TIM3), and adenosine A2a receptor (A2aR). In a specific embodiment, the antagonist of an inhibitory receptor expressed by an immune cell is an antibody (or an antigen-binding fragment thereof) that specifically binds to the co-stimulatory receptor. In one embodiment, the antibody is a monoclonal antibody. In another embodiment, the antibody is an sc-Fv. In specific embodiments, the antibody is a human or humanized antibody. In another specific embodiment, the antagonist of an inhibitory receptor is a soluble receptor or antibody (or an antigen-binding fragment thereof) that specifically binds to a ligand of the inhibitory receptor.

In another aspect, presented herein are methods for propagating the NDVs described herein (e.g., chimeric NDVs described herein). The NDVs described herein (e.g., chimeric NDVs described herein) can be propagated in any cell, subject, tissue or organ susceptible to a NDV infection. In one embodiment, the NDVs described herein (e.g., chimeric NDVs described herein) may be propagated in a cell line. In another embodiment, the NDVs described herein (e.g., chimeric NDVs described herein) may be propagated in cancer cells. In another embodiment, the NDVs described herein (e.g., chimeric NDVs described herein) may be propagated in an embryonated egg. In certain embodiments, presented herein are isolated cells, tissues or organs infected with an NDV described herein (e.g., a chimeric NDV described herein). See, e.g., Section 5.4, infra, for examples of cells, animals and eggs to infect with an NDV described herein (e.g., a chimeric NDV described herein). In specific embodiments, presented herein are isolated cancer cells infected with an NDV described herein (e.g., a chimeric NDV described herein). In certain embodiments, presented herein are cell lines infected with an NDV described herein (e.g., a chimeric NDV described herein). In other embodiments, presented herein are embryonated eggs infected with an NDV described herein (e.g., a chimeric NDV described herein).

In another aspect, presented herein are compositions comprising an NDV described herein (e.g., a chimeric NDV described herein). In a specific embodiment, presented herein are pharmaceutical compositions comprising an NDV described herein (e.g., a chimeric NDV described herein) and a pharmaceutically acceptable carrier. In another embodiment, presented herein are pharmaceutical compositions comprising cancer cells infected with an NDV described herein (e.g., a chimeric NDV described herein), and a pharmaceutically acceptable carrier. In specific embodiments, the cancer cells have been treated with gamma radiation prior to incorporation into the pharmaceutical composition. In specific embodiments, the cancer cells have been treated with gamma radiation before infection with the NDV (e.g., chimeric NDV). In other specific embodiments, the cancer cells have been treated with gamma radiation after infection with the NDV (e.g., chimeric NDV). In another embodiment, presented herein are pharmaceutical compositions comprising protein concentrate from lysed NDV-infected cancer cells (e.g., chimeric-NDV infected cancer cells), and a pharmaceutically acceptable carrier.

In another aspect, presented herein are methods for producing pharmaceutical compositions comprising an NDV described herein (e.g., a chimeric NDV described herein). In one embodiment, a method for producing a pharmaceutical composition comprises: (a) propagating an NDV described herein (e.g., a chimeric NDV described herein) in a cell line that is susceptible to an NDV infection; and (b) collecting the progeny virus, wherein the virus is grown to sufficient quantities and under sufficient conditions that the virus is free from contamination, such that the progeny virus is suitable for formulation into a pharmaceutical composition. In another embodiment, a method for producing a pharmaceutical composition comprises: (a) propagating an NDV described herein (e.g., a chimeric NDV described herein) in an embryonated egg; and (b) collecting the progeny virus, wherein the virus is grown to sufficient quantities and under sufficient conditions that the virus is free from contamination, such that the progeny virus is suitable for formulation into a pharmaceutical composition.

In another aspect, presented herein are methods for treating cancer utilizing a chimeric NDV described herein (e.g., a chimeric NDV described in Section 5.2, infra) or a composition comprising such a chimeric NDV. In a specific embodiment, a method for treating cancer comprises infecting a cancer cell in a subject with a chimeric NDV described herein (e.g., a chimeric NDV described in Section 5.2, infra) or a composition thereof. In another embodiment, a method for treating cancer comprises administering to a subject in need thereof a chimeric NDV described herein (e.g., a chimeric NDV described in Section 5.2, infra) or a composition thereof. In specific embodiments, an effective amount of a chimeric NDV described herein (e.g., a chimeric NDV described in Section 5.2, infra) or a composition comprising an effective amount of a chimeric NDV described herein is administered to a subject to treat cancer. In specific embodiments, the chimeric NDV comprises a genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell). In certain embodiments, the genome of the NDV also comprises a mutated F protein. In certain embodiments, two or more chimeric NDVs are administered to a subject to treat cancer.

In another embodiment, a method for treating cancer comprises administering to a subject in need thereof cancer cells infected with a chimeric NDV described herein (e.g., a chimeric NDV described in Section 5.2, infra) or composition thereof. In specific embodiments, the cancer cells have been treated with gamma radiation prior to administration to the subject or incorporation into the composition. In another embodiment, a method for treating cancer comprises administering to a subject in need thereof a protein concentrate or plasma membrane fragments from cancer cells infected with a chimeric NDV (e.g., a chimeric NDV described in Section 5.2, infra) or a composition thereof. In specific embodiments, the chimeric NDV comprises a genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell). In certain embodiments, the genome of the NDV also comprises a mutated F protein.

In another aspect, presented herein are methods for treating cancer utilizing an NDV described herein (e.g., a chimeric NDV such as described in Section 5.2, infra) or a composition comprising such the NDV in combination with one or more other therapies. In one embodiment, presented herein are methods for treating cancer comprising administering to a subject an NDV described herein (e.g., a chimeric NDV, such as described in Section 5.2.1, infra) and one or more other therapies. In another embodiment, presented herein are methods for treating cancer comprising administering to a subject an effective amount of an NDV described herein or a composition comprising an effective amount of an NDV described herein, and one or more other therapies. The NDV and one or more other therapies can be administered concurrently or sequentially to the subject. In certain embodiments, the NDV and one or more other therapies are administered in the same composition. In other embodiments, the NDV and one or more other therapies are administered in different compositions. The NDV and one or more other therapies can be administered by the same or different routes of administration to the subject.

Any NDV type or strain may be used in a combination therapy disclosed herein, including, but not limited to, naturally-occurring strains, variants or mutants, mutagenized viruses, reassortants and/or genetically engineered viruses. In a specific embodiment, the NDV used in a combination with one or more other therapies is a naturally-occurring strain. In another embodiment, the NDV used in combination with one or more other therapies is a chimeric NDV. In a specific embodiment, the chimeric NDV comprises a packaged genome, the genome comprising a cytokine (e.g., IL-2, IL-7, IL-15, IL-17, or IL-21). In specific embodiments, the cytokine is expressed by cells infected with the chimeric NDV. In a specific embodiment, the chimeric NDV comprises a packaged genome, the genome comprising a tumor antigen. In specific embodiments, the tumor antigen is expressed by cells infected with the chimeric NDV. In a specific embodiment, the chimeric NDV comprises a packaged genome, the genome comprising a pro-apoptotic molecule or an anti-apoptotic molecule. In specific embodiments, the pro-apoptotic molecule or anti-apoptotic molecule is expressed by cells infected with the chimeric NDV.

In another specific embodiment, the chimeric NDV comprises a packaged genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell). In specific embodiments, the agonist and/or antagonist are expressed by cells infected with the chimeric NDV. In certain embodiments, the genome of the NDV also comprises a mutated F protein. In certain embodiments, the one or more therapies used in combination with an NDV described herein is one or more other therapies described in Section 5.6.4 infra. In particular embodiments, the one or more therapies used in combination with an NDV described herein is an agonist of a co-stimulatory signal of an immune cell and/or an antagonist of an inhibitory signal of an immune cell (see, e.g., Section 5.6.4.4.1, infra). See, e.g., Section 5.2.1, infra, for examples of agonists of a co-stimulatory signal of an immune cell and antagonists of an inhibitory signal of an immune cell. In a specific embodiment, the antagonist of an inhibitory signal of an immune cell is the anti-CTLA-4 antibody described in Section 6, infra. In another specific embodiment, the agonist of a co-stimulatory signal of an immune cell is the ICOS ligand described in Section 6, infra 3.1 Terminology As used herein, the term "about" or "approximately" when used in conjunction with a number refers to any number within 1, 5 or 10% of the referenced number.

As used herein, the term "agonist(s)" refers to a molecule (s) that binds to another molecule and induces a biological reaction. In a specific embodiment, an agonist is a molecule that binds to a receptor on a cell and triggers one or more signal transduction pathways. For example, an agonist includes an antibody or ligand that binds to a receptor on a cell and induces one or more signal transduction pathways. In certain embodiments, the antibody or ligand binds to a receptor on a cell and induces one or more signal transduction pathways. In other embodiments, the agonist facilitates the interaction of the native ligand with the native receptor.

As used herein, the term "antagonist(s)" refers to a molecule(s) that inhibits the action of another molecule without provoking a biological response itself. In a specific embodiment, an antagonist is a molecule that binds to a receptor on a cell and blocks or dampens the biological activity of an agonist. For example, an antagonist includes an antibody or ligand that binds to a receptor on a cell and blocks or dampens binding of the native ligand to the cell without inducing one or more signal transduction pathways. Another example of an antagonist includes an antibody or soluble receptor that competes with the native receptor on cells for binding to the native ligand, and thus, blocks or dampens one or more signal transduction pathways induced when the native receptor binds to the native ligand.

As used herein, the terms "antibody" and "antibodies" refer to molecules that contain an antigen binding site, e.g., immunoglobulins. Antibodies include, but are not limited to, monoclonal antibodies, bispecific antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., IgG1, IgG2, IgG3, IgG4, IgA1 and IgA2) or subclass. In a specific embodiment, an antibody is a human or humanized antibody. In another specific embodiment, an antibody is a monoclonal antibody or scFv. In certain embodiments, an antibody is a human or humanized monoclonal antibody or scFv. In other specific embodiments, the antibody is a bispecific antibody. In certain embodiments, the bispecific antibody specifically binds to a co-stimulatory receptor of an immune cell or an inhibitory receptor of an immune, and a receptor on a cancer cell. In some embodiments, the bispecific antibody specifically binds to two receptors immune cells, e.g., two co-stimulatory receptors on immune cells, two inhibitory receptors on immune cells, or one co-stimulatory receptor on immune cells and one inhibitory receptor on immune cells.

As used herein, the term "derivative" in the context of proteins or polypeptides refers to: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native polypeptide; (d) a polypeptide encoded by nucleic acid sequence that can hybridize under high, moderate or typical stringency hybridization conditions to a nucleic acid sequence encoding a native polypeptide; (e) a polypeptide encoded by a nucleic acid sequence that can hybridize under high, moderate or typical stringency hybridization conditions to a nucleic acid sequence encoding a fragment of a native polypeptide of at least 10 contiguous amino acids, at least 12 contiguous amino acids, at least 15 contiguous amino acids, at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, at least 150 contiguous amino acids, or 10 to 20, 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native polypeptide. Derivatives also include a polypeptide that comprises the amino acid sequence of a naturally occurring mature form of a mammalian polypeptide and a heterologous signal peptide amino acid sequence. In addition, derivatives include polypeptides that have been chemically modified by, e.g., glycosylation, acetylation, pegylation, phosphorylation, amidation, derivitization by known protecting/blocking groups, proteolytic cleavage, linkage to a cellular ligand or other protein moiety, etc. Further, derivatives include polypeptides comprising one or more non-classical amino acids. In one embodiment, a derivative is isolated. In specific embodiments, a derivative retains one or more functions of the native polypeptide from which it was derived.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) have been described, see, e.g., U.S. Patent Application Publication No. US 2005/0048549 (e.g., paragraphs 72-73).

As used herein, the term "fragment" is the context of a fragment of a proteinaceous agent (e.g., a protein) refers to a fragment that is 8 or more contiguous amino acids, 10 or more contiguous amino acids, 15 or more contiguous amino acids, 20 or more contiguous amino acids, 25 or more contiguous amino acids, 50 or more contiguous amino acids, 75 or more contiguous amino acids, 100 or more contiguous amino acids, 150 or more contiguous amino acids, 200 or more contiguous amino acids, or in the range of between 10 to 300 contiguous amino acids, 10 to 200 contiguous amino acids, 10 to 250 contiguous amino acids, 10 to 150 contiguous amino acids, 10 to 100 contiguous amino acids, 10 to 50 contiguous amino acids, 50 to 100 contiguous amino acids, 50 to 150 contiguous amino acids, 50 to 200 contiguous amino acids, 50 to 250 contiguous amino acids, 50 to 300 contiguous amino acids, 25 to 50 contiguous amino acids, 25 to 75 contiguous amino acids, 25 to 100 contiguous amino acids, or 75 to 100 contiguous amino acids of a proteinaceous agent. In a specific embodiment, a fragment of a proteinaceous agent retains one or more functions of the proteinaceous agent—in other words, it is a functional fragment. For example, a fragment of a proteinaceous agent retains the ability to interact with another protein and/or to induce, enhance or activate one or more signal transduction pathways.

As used herein, the term "functional fragment," in the context of a proteinaceous agent, refers to a portion of a proteinaceous agent that retains one or more activities or functions of the proteinaceous agent. For example, a functional fragment of an inhibitory receptor may retain the ability to bind one or more of its ligands. A functional fragment of a ligand of a co-stimulatory receptor may retain the ability to bind to the receptor and/or induce, enhance or activate one or more signal transduction pathways mediated by the ligand binding to its co-stimulatory receptor.

As used herein, the term "heterologous" refers an entity not found in nature to be associated with (e.g., encoded by and/or expressed by the genome of) a naturally occurring NDV.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

In certain embodiments, the terms "highly fusogenic" and "increased fusogenic activity", and the like, as used herein, refers to an increase in the ability of the NDV to form syncytia involving a large number of cells. In a specific embodiment, cells infected with an NDV described herein that is engineered to express a mutated F protein have an increased ability to form syncytia relative to cells infected with the parental virus from which the virus is derived, which parental virus has an unmutated F protein. In another specific embodiment, about 10% to about 25%, about 25% to about 50%, about 25% to about 75%, about 50% to about 75%, about 50% to about 95%, or about 75% to about 99% or about 10%, 15%, 20%, 25%, 30%, 35%, 40%, 45%, 50%, 55%, 60%, 65%, 70%, 75%, 80%, 85%, 90%, 95%, or 99% more cells infected with an NDV described herein that is engineered to express a mutated F protein form syncytia relative to the number of cells forming syncytia that are infected with the parental virus from the chimeric virus is derived which has an unmutated F protein. In certain embodiments, the syncytia are quantitated microscopically by counting the number of nuclei per syncytium after a certain period of time (e.g., about 8 hours to about 12 hours, about 12 hours to about 24 hours, about 24 hours to about 36 hours, or about 36 hours to about 48 hours).

As used herein, the term "interferon antagonist" refers to an agent that reduces or inhibits the cellular interferon immune response. In one embodiment, an interferon antagonist is a proteinaceous agent that reduces or inhibits the cellular interferon immune response. In a specific embodiment, an interferon antagonist is a viral protein or polypeptide that reduces or inhibits the cellular interferon response.

In a specific embodiment, an interferon antagonist is an agent that reduces or inhibits interferon expression and/or activity. In one embodiment, the interferon antagonist reduces or inhibits the expression and/or activity of type I IFN. In another embodiment, the interferon antagonist reduces or inhibits the expression and/or activity of type II IFN. In another embodiment, the interferon antagonist reduces or inhibits the expression and/or activity of type III IFN. In a specific embodiment, the interferon antagonist reduces or inhibits the expression and/or activity of either IFN-α, IFN-β or both. In another specific embodiment, the interferon antagonist reduces or inhibits the expression and/or activity of IFN-γ. In another embodiment, the interferon antagonist reduces or inhibits the expression and/or activity of one, two or all of IFN-α, IFN-β, and IFN-γ.

In certain embodiments, the expression and/or activity of IFN-α, IFN-β and/or IFN-γ in an embryonated egg or cell is reduced approximately 1 to approximately 100 fold, approximately 5 to approximately 80 fold, approximately 20 to approximately 80 fold, approximately 1 to approximately 10 fold, approximately 1 to approximately 5 fold, approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art. In other embodiments, the expression and/or activity of IFN-α, IFN-β and/or IFN-γ in an embryonated egg or cell is reduced by at least 20% to 25%, at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80% to 85%, at least 85% to 90%, at least 90% to 95%, at least 95% to 99% or by 20%, 25%, 30%, 35%, 40%, 45%, 50%, 55%, 60%, 65%, 70%, 75%, 80%, 85%, 90%, 95%, or 99% by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art.

As used herein, the phrases "IFN deficient systems" or "IFN-deficient substrates" refer to systems, e.g., cells, cell lines and animals, such as mice, chickens, turkeys, rabbits, rats, horses etc., which do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one, two or more types of IFN, or do not respond to any type of IFN, have a delayed response to one, two or more types of IFN, and/or are deficient in the activity of antiviral genes induced by one, two or more types of IFN, or induced by any type of IFN.

As used herein, the terms "immunospecifically binds," "immunospecifically recognizes," "specifically binds," and "specifically recognizes" are analogous terms in the context of antibodies and refer to molecules that specifically bind to an antigen (e.g., epitope or immune complex) as understood by one skilled in the art. A molecule that specifically binds to an antigen may bind to other peptides or polypeptides with lower affinity as determined by, e.g., immunoassays (e.g., ELISA), surface plasmon resonance (e.g., BIAcore®), a KinEx assay (using, e.g., a KinExA 3000 instrument (Sapidyne Instruments, Boise, Id.)), or other assays known in the art. In a specific embodiment, molecules that specifically bind to an antigen bind to the antigen with a dissociation constant (i.e., Ka) that is at least 2 logs, 2.5 logs, 3 logs, 3.5 logs, 4 logs or greater than the Ka when the molecules bind to another antigen. In a another specific embodiment, molecules that specifically bind to an antigen do not cross react with other proteins.

As used herein, the term "monoclonal antibody" is a term of the art and generally refers to an antibody obtained from a population of homogenous or substantially homogeneous antibodies, and each monoclonal antibody will typically recognize a single epitope (e.g., single conformation epitope) on the antigen.

As used herein, the phrase "multiplicity of infection" or "MOI" is the average number of virus per infected cell. The MOI is determined by dividing the number of virus added (ml added×Pfu) by the number of cells added (ml added× cells/ml).

As used herein, the term "native ligand" refers to any naturally occurring ligand that binds to a naturally occurring receptor. In a specific embodiment, the ligand is a mammalian ligand. In another specific embodiment, the ligand is a human ligand.

As used herein, the term "native polypeptide(s)" in the context of proteins or polypeptides refers to any naturally occurring amino acid sequence, including immature or precursor and mature forms of a protein. In a specific embodiment, the native polypeptide is a human protein or polypeptide.

As used herein, the term "native receptor" refers to any naturally occurring receptor that binds to a naturally occurring ligand. In a specific embodiment, the receptor is a mammalian receptor. In another specific embodiment, the receptor is a human receptor.

As used herein, the terms "subject" or "patient" are used interchangeably. As used herein, the terms "subject" and "subjects" refers to an animal. In some embodiments, the subject is a mammal including a non-primate (e.g., a camel, donkey, zebra, cow, horse, horse, cat, dog, rat, and mouse) and a primate (e.g., a monkey, chimpanzee, and a human). In some embodiments, the subject is a non-human mammal. In certain embodiments, the subject is a pet (e.g., dog or cat) or farm animal (e.g., a horse, pig or cow). In other embodiments the subject is a human. In certain embodiments, the mammal (e.g., human) is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the subject is an animal that is not avian.

As used herein, the terms "treat" and "treating" in the context of the administration of a therapy refers to a treatment/therapy from which a subject receives a beneficial effect, such as the reduction, decrease, attenuation, diminishment, stabilization, remission, suppression, inhibition or arrest of the development or progression of cancer, or a symptom thereof. In certain embodiments, the treatment/therapy that a subject receives results in at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) the reduction in hospitalization length; (vii) the increase in the survival of a subject; (viii) the inhibition of the progression of cancer and/or a symptom associated therewith; (ix) the enhancement or improvement the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse-free survival; (xix) an increase in the number of patients in remission; (xx) a decrease in hospitalization rate; (xxi) the size of the tumor is maintained and does not increase in size or increases the size of the tumor by less 5% or 10% after administration of a therapy as measured by conventional methods available to one of skill in the art, such as MRI, X-ray, and CAT Scan; (xxii) the prevention of the development or onset of cancer and/or a symptom associated therewith; (xxiii) an increase in the length of remission in patients; (xxiv) the reduction in the number of symptoms associated with cancer; (xxv) an increase in symptom-free survival of cancer patients; and/or (xxvi) limitation of or reduction in metastasis. In some embodiments, the treatment/therapy that a subject receives does not cure cancer, but prevents the progression or worsening of the disease. In certain embodiments, the treatment/therapy that a subject receives does not prevent the onset/development of cancer, but may prevent the onset of cancer symptoms.

As used herein, the term "in combination" in the context of the administration of (a) therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the terms "therapies" and "therapy" can refer to any protocol(s), method(s), and/or agent(s) that can be used in the treatment of cancer. In certain embodiments, the terms "therapies" and "therapy" refer to biological therapy, supportive therapy, hormonal therapy, chemotherapy, immunotherapy and/or other therapies useful in the treatment of cancer. In a specific embodiment, a therapy includes adjuvant therapy. For example, using a therapy in conjunction with a drug therapy, biological therapy, surgery, and/or supportive therapy. In certain embodiments, the term "therapy" refers to a chimeric NDV described herein. In other embodiments, the term "therapy" refers to an agent that is not a chimeric NDV.

4. BRIEF DESCRIPTION OF THE FIGURES

FIG. 1. NDV infection upregulates the expression of MHC I, MHC II, and ICAM-1 on the surface of in vitro infected B16-F10 cells (24 hours post-infection).

FIGS. 2A-2E. Intratumoral NDV treatment leads to infiltration with macrophages, NK cells, CD8 and CD4 effector cells and decreases the frequency of Tregs. A) Overall study scheme. B) Total CD45+ infiltrates. C) Total immune cell infiltrates. D) Representative flow cytometry dot plots of relative CD4 FoxP3+ and FoxP3− subsets. E) Teff/Treg and CD8/Treg ratios.

Figure 3A:
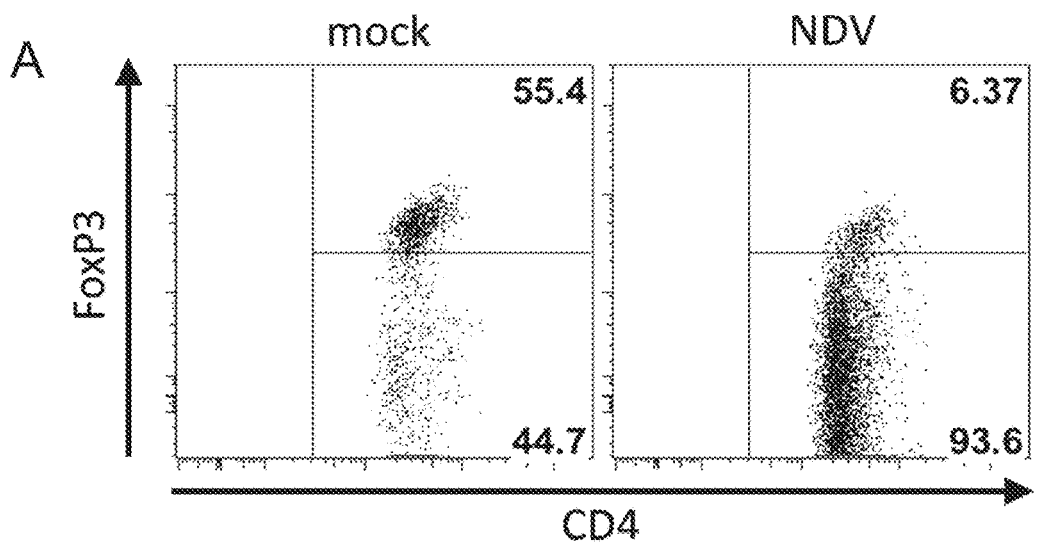
Figure 3B:
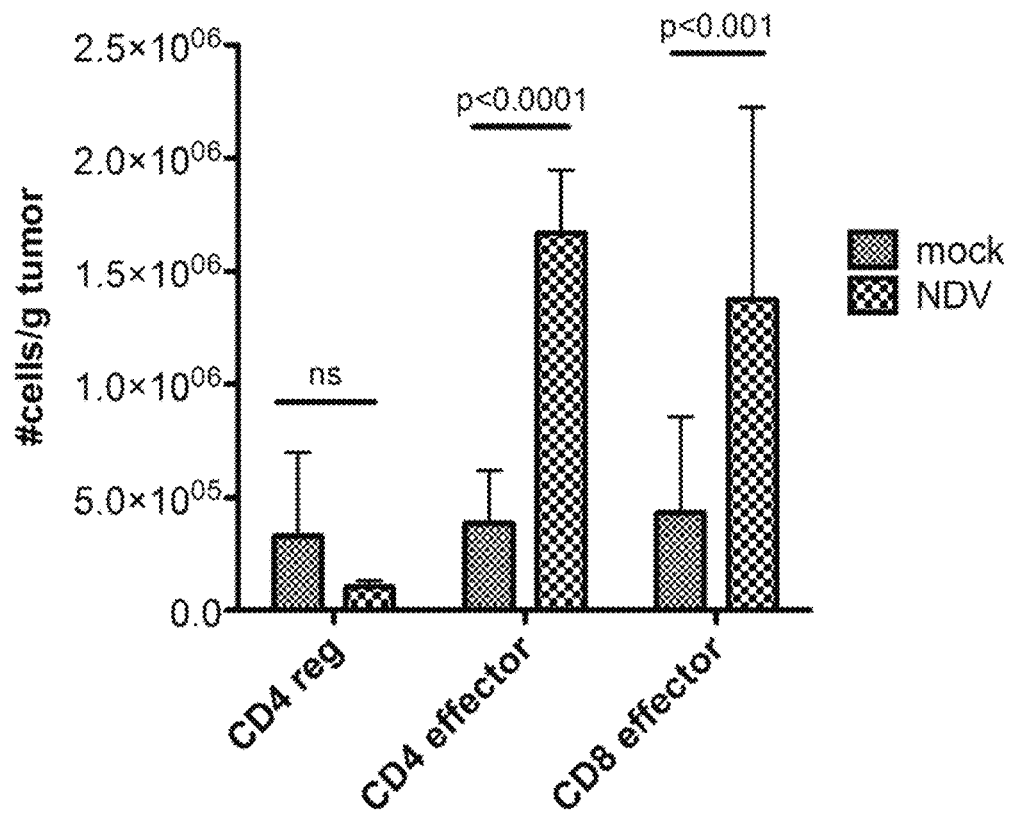
Figure 3C:
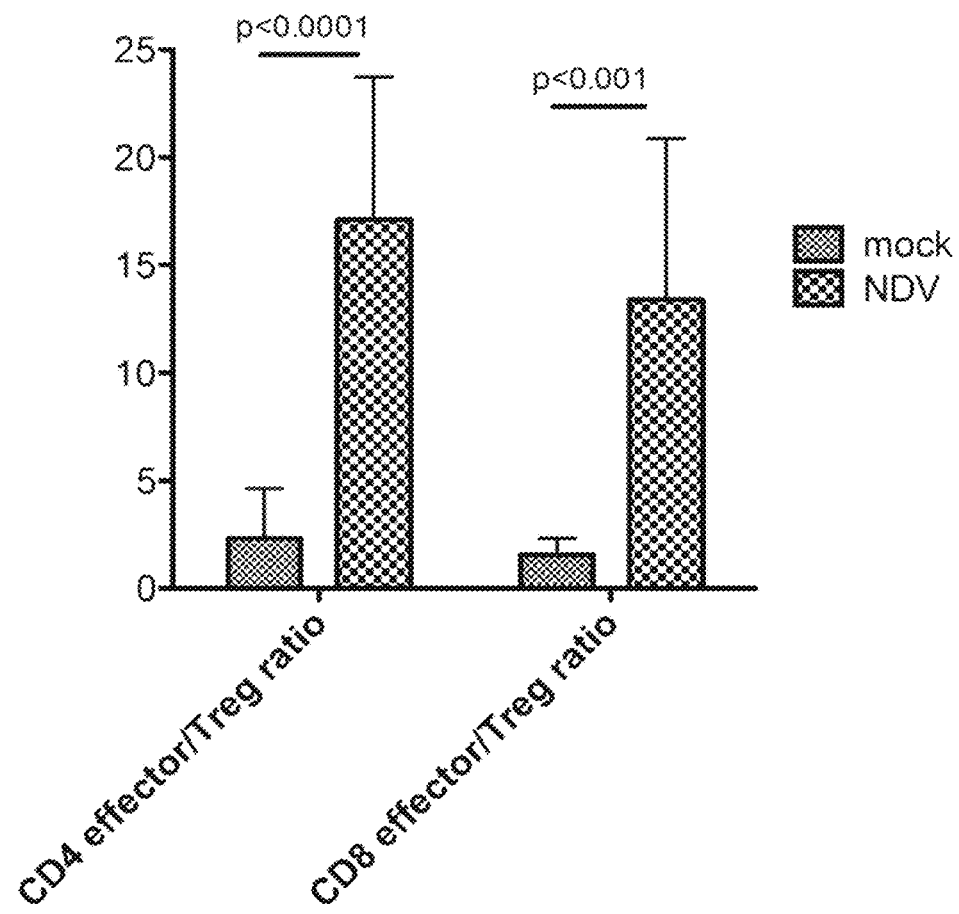

FIGS. 3A-3C. Therapy with NDV exhibits favorable effects on tumor microenvironment of distant tumors. A) Representative flow cytometry dot plots of relative CD4 FoxP3+ and FoxP3− subsets. B) Absolute numbers of CD4 effector, Treg, and CD8 cells per gram of tumor. C) Teff/Treg and CD8/Treg ratios.

Figure 4A:
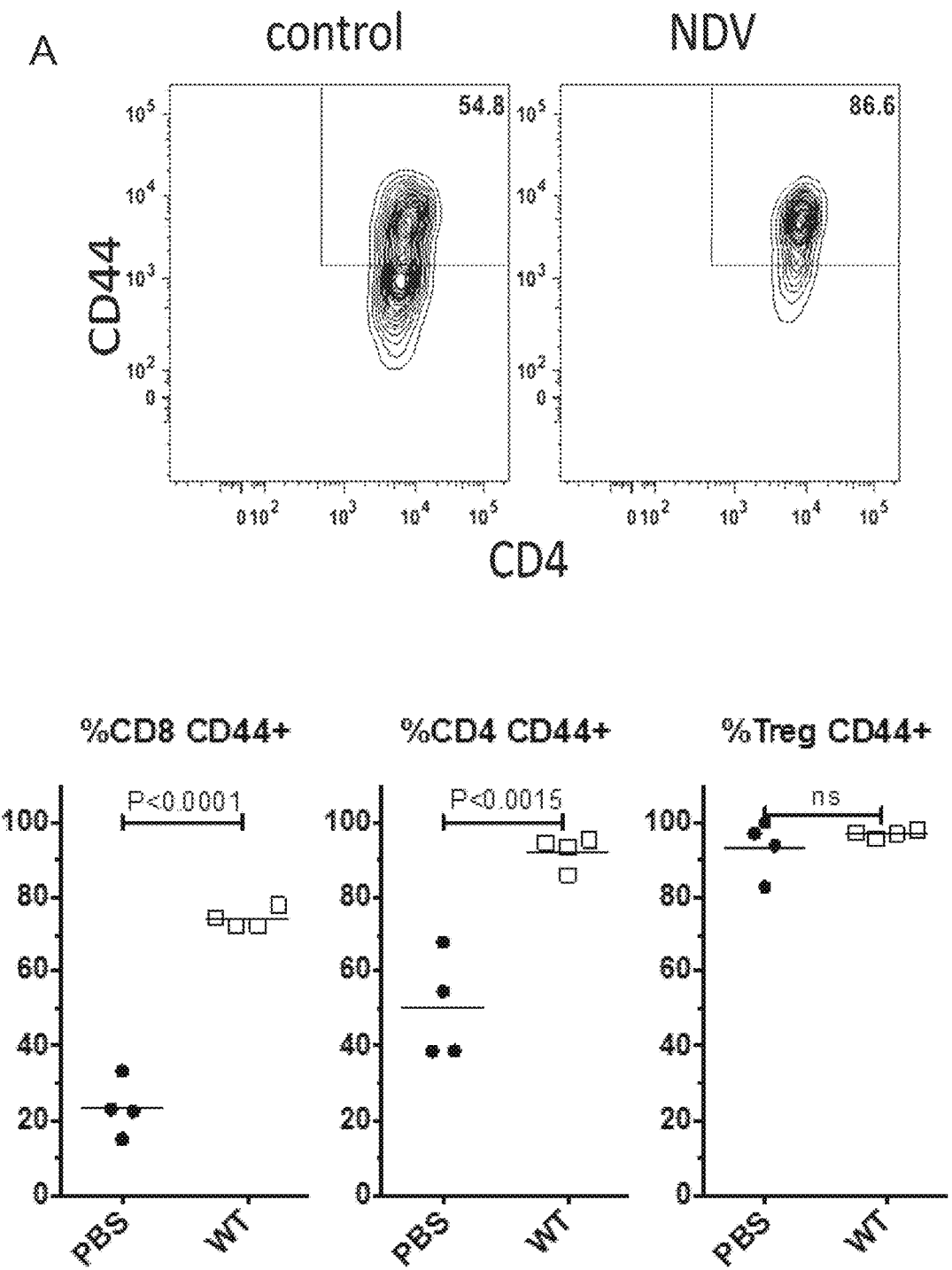
Figure 4B:
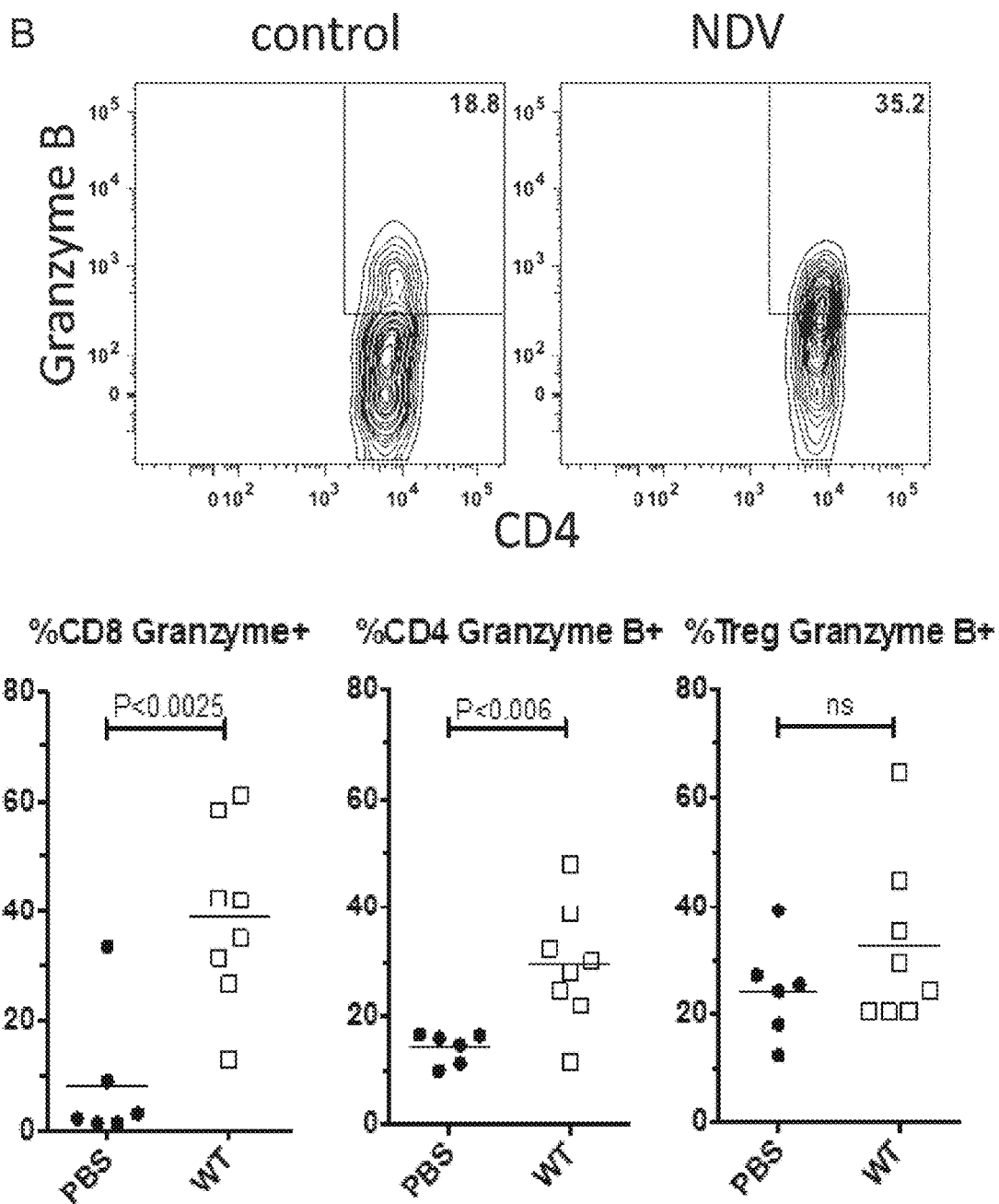
Figure 4C:
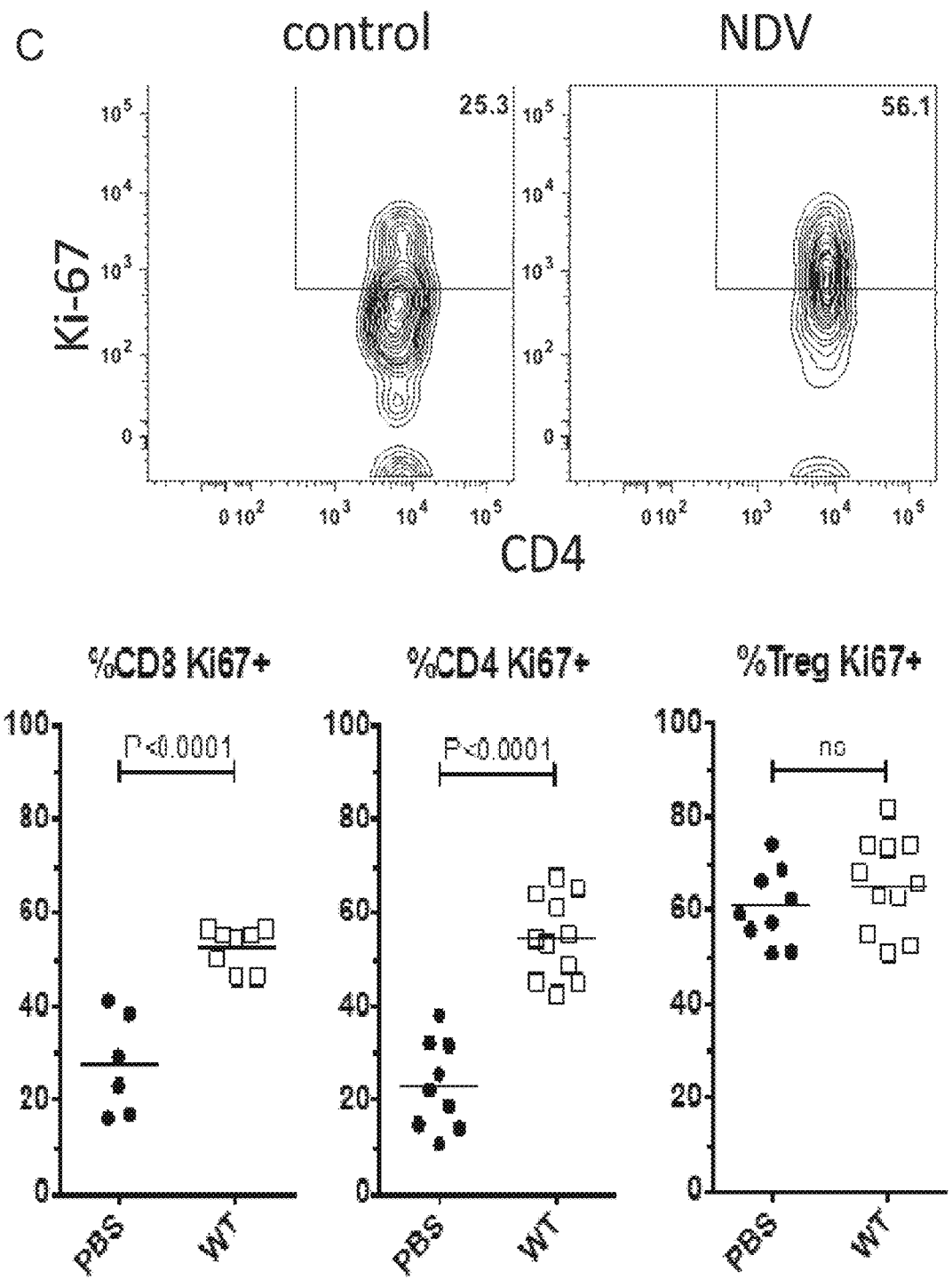

FIGS. 4A-4C. Lymphocytes infiltrating distant tumors upregulate activation, lytic, and proliferation markers. Representative expression plots on CD4 effector cells (top) and the corresponding percentages in the CD4 effector, CD8, Tregs (bottom) are shown for A) CD44, B) Granzyme B, and C) Ki-67.

FIGS. 5A-5D. NDV Monotherapy delays the growth of distant tumors and provides some protection against tumor rechallenge. Bilateral flank tumors were established as described in FIG. 2A and the animals were treated and followed for survival. A) Growth of right flank (treated) tumors. B) Growth of left flank (non-treated) tumors. C) Overall survival. Numbers in boxes indicate percent of animals free of tumors. D) Survival in animals cured of B16-F10 melanoma by NDV re-challenged on day 75 with B16-F10 melanoma cells. Representative results of two different experiments with 10 mice per group.

Figure 6A:
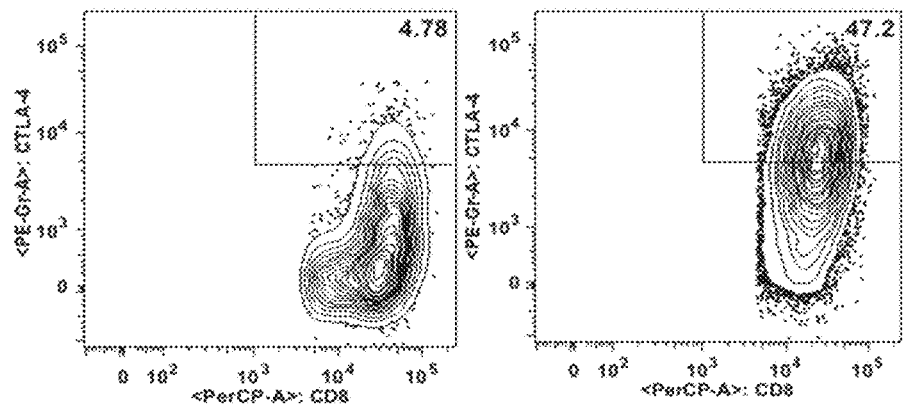
Figure 6A:
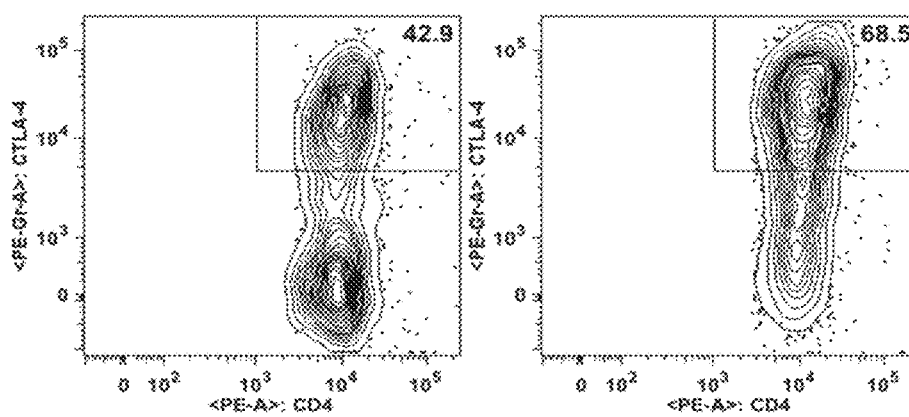
Figure 6A:
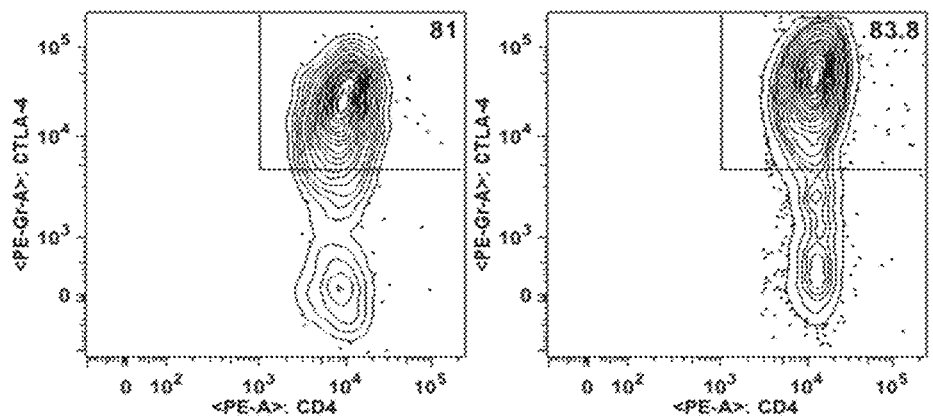
Figure 6B:
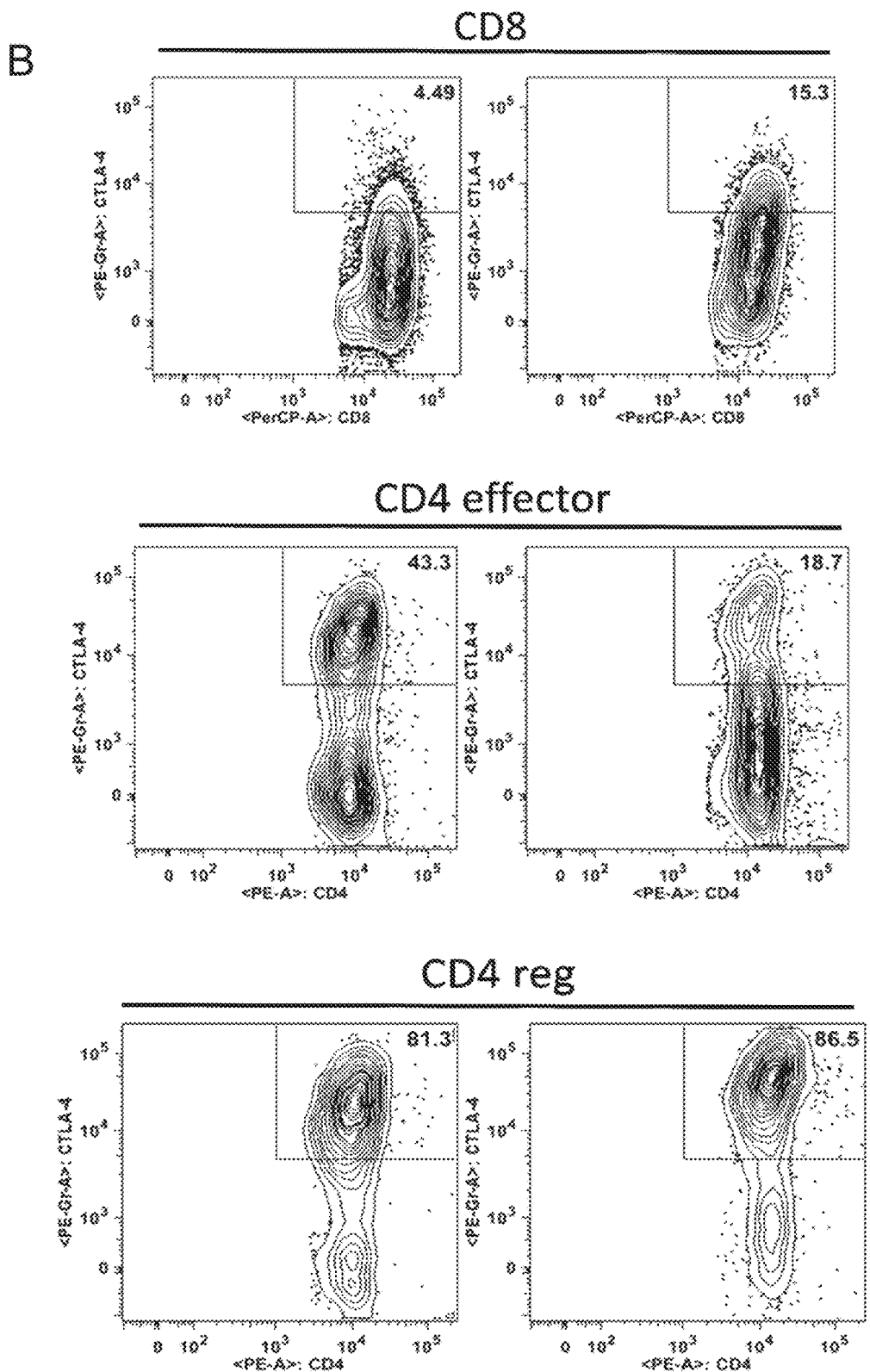

FIGS. 6A-6B. Tumor-infiltrating lymphocytes from both treated and non-treated tumors upregulate CTLA-4 in response to NDV therapy. A) Representative dot plots of CTLA-4 expression in CD8, CD4 effector, and Tregs in right (treated) tumors. B) Representative dot plots of CTLA-4 expression in CD8, CD4 effector, and Tregs in left (non-treated) tumors.

Figure 7A:
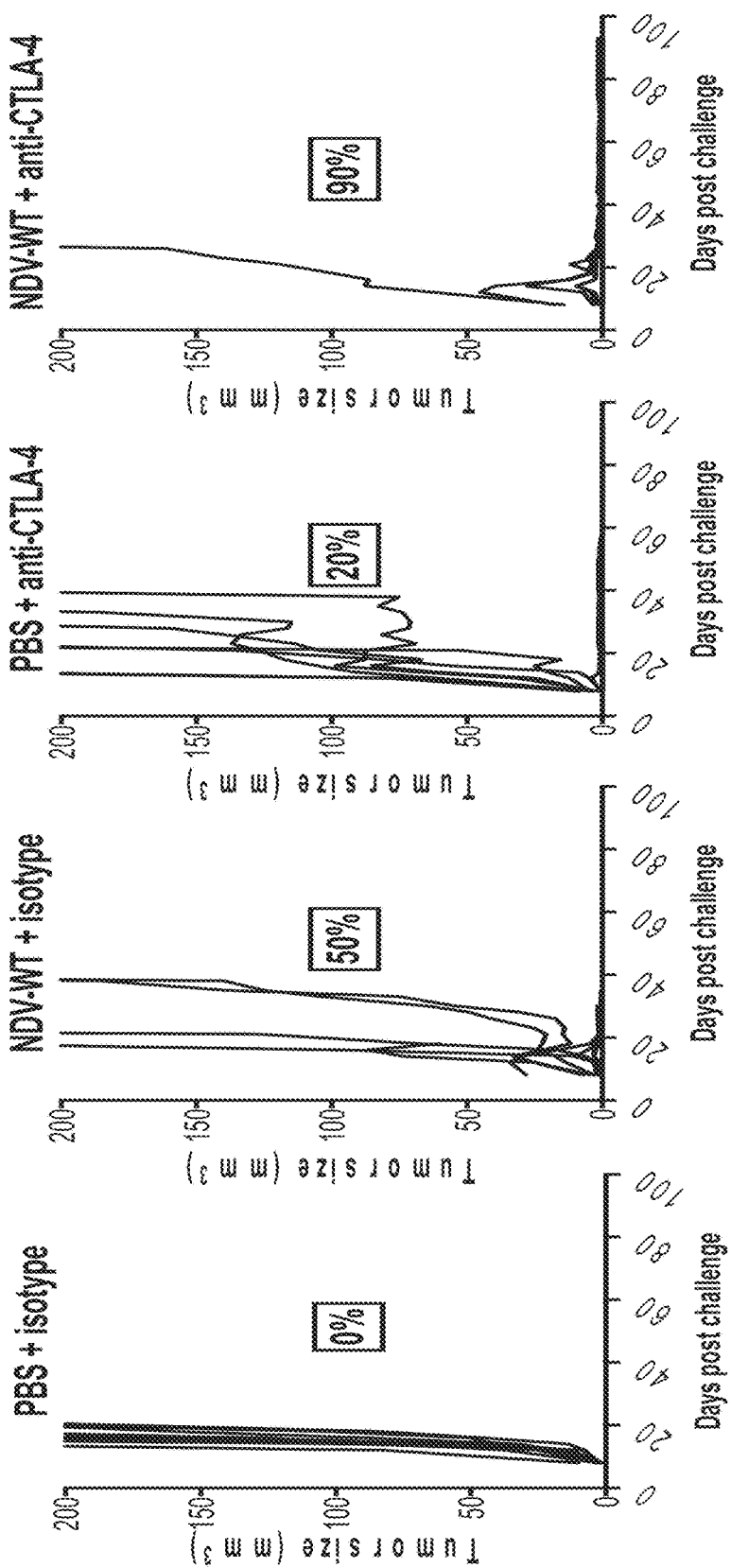
Figure 7B:
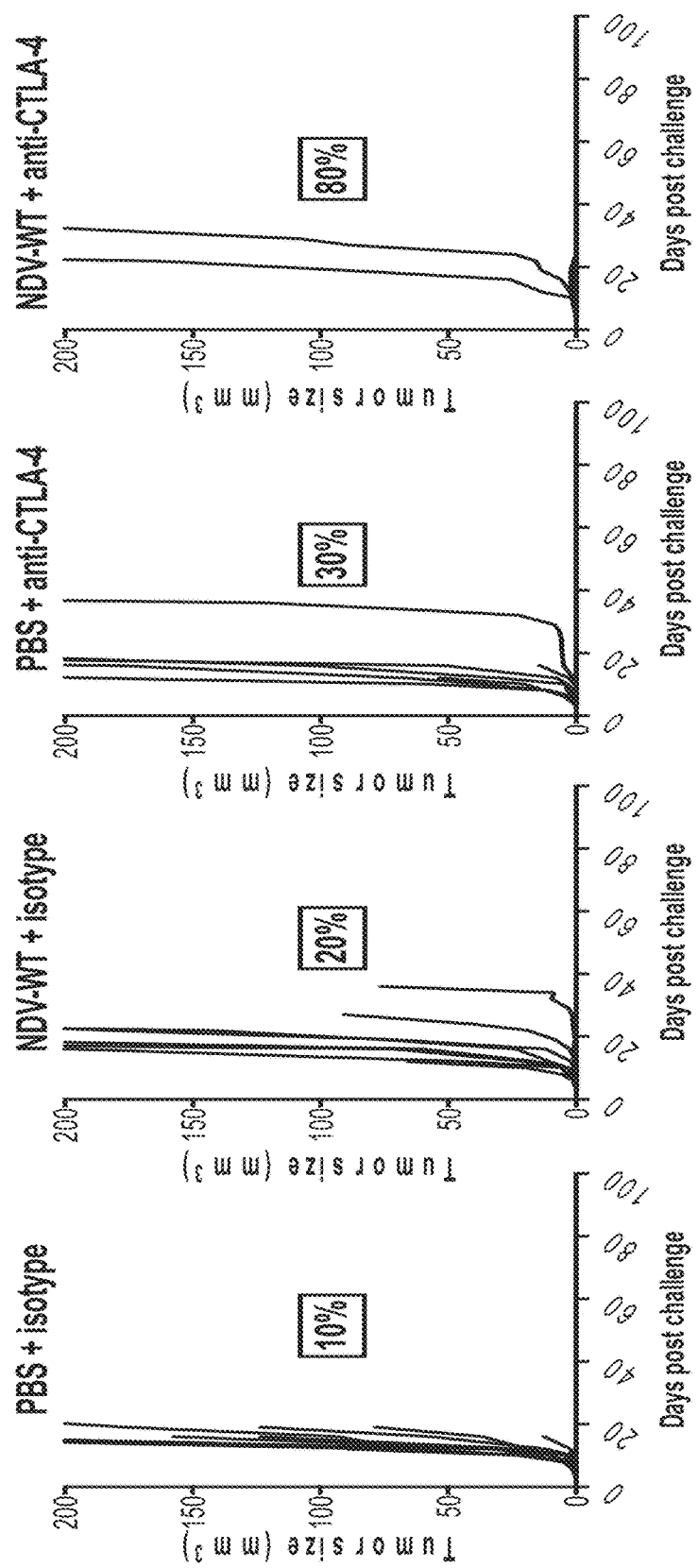
Figure 7C:
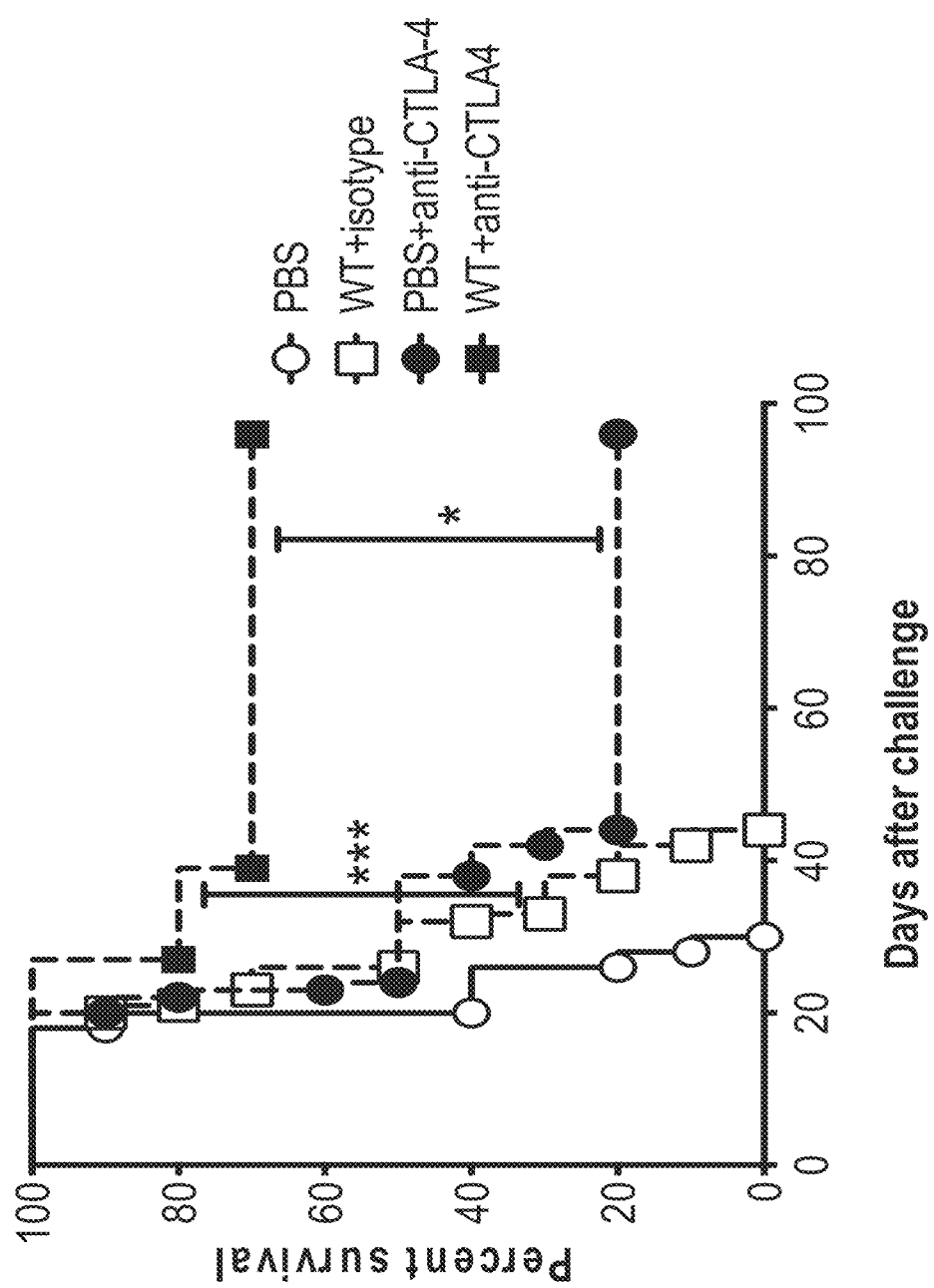

FIG. 7A-7C. Combination therapy with NDV and CTLA-4 blockade enhances anti-tumor effect in the injected and distant tumors. Bilateral B16 flank tumors were established and the animals were treated as described in FIG. 2A with or without anti-CTLA-4 antibody 9H10. A) Growth of treated tumors. B) Growth of distant tumors. Numbers in boxes represent percentage of mice free of tumors. C) Long-term survival. Representative results of 2 different experiments with 10 mice per group.

Figure 8:
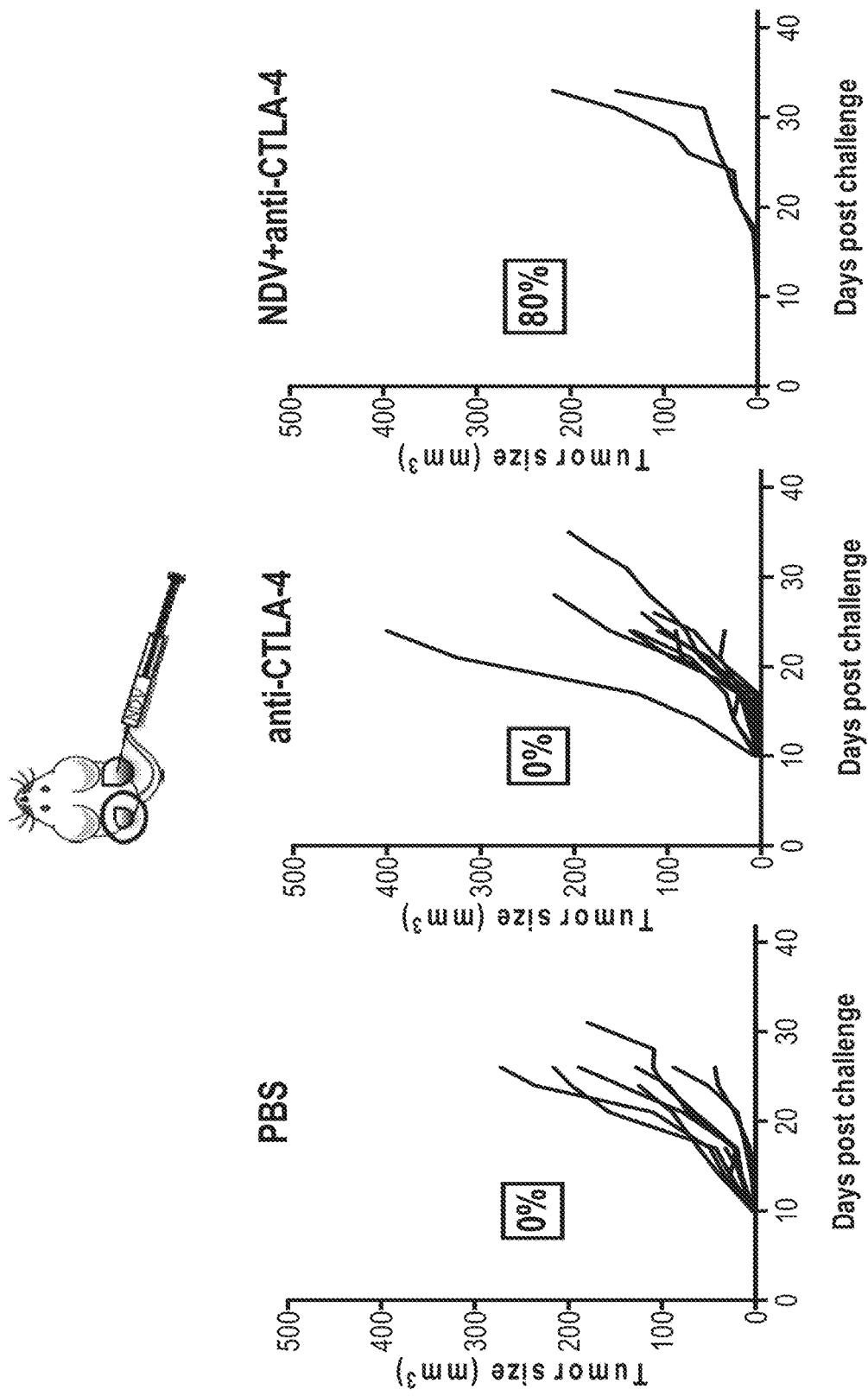

FIG. 8. Combination therapy with NDV and anti-CTLA-4 is effective systemically against non-virus-permissive prostate TRAMP tumors. Right (day 12) and left (day 3) flank TRAMP tumors were established and the animals were treated with NDV as described in FIG. 2A with or without systemic anti-CTLA-4 antibody. Growth of left flank (non-injected) tumors is shown. Numbers in boxes indicate percent of animals free of tumors.

Figures 9A, 9B:
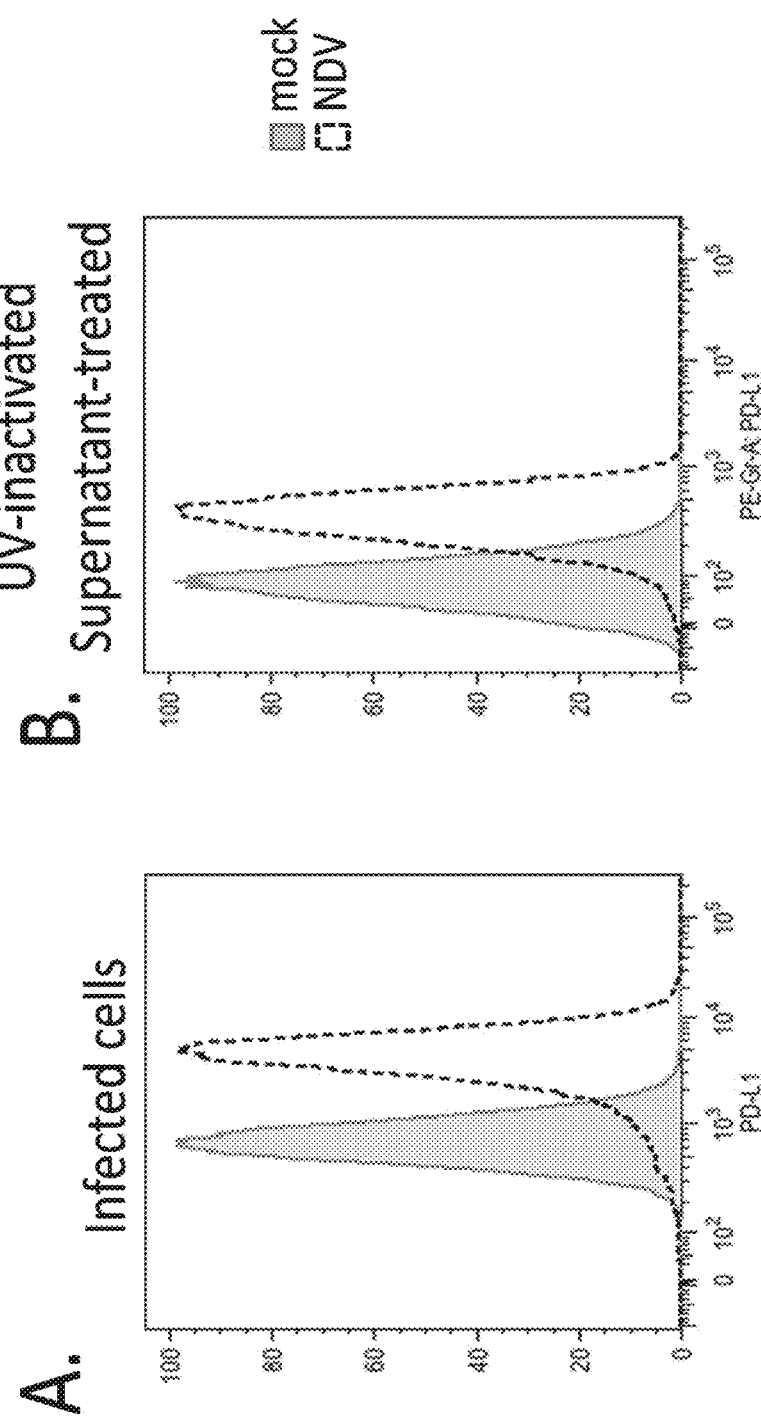
Figure 9C:
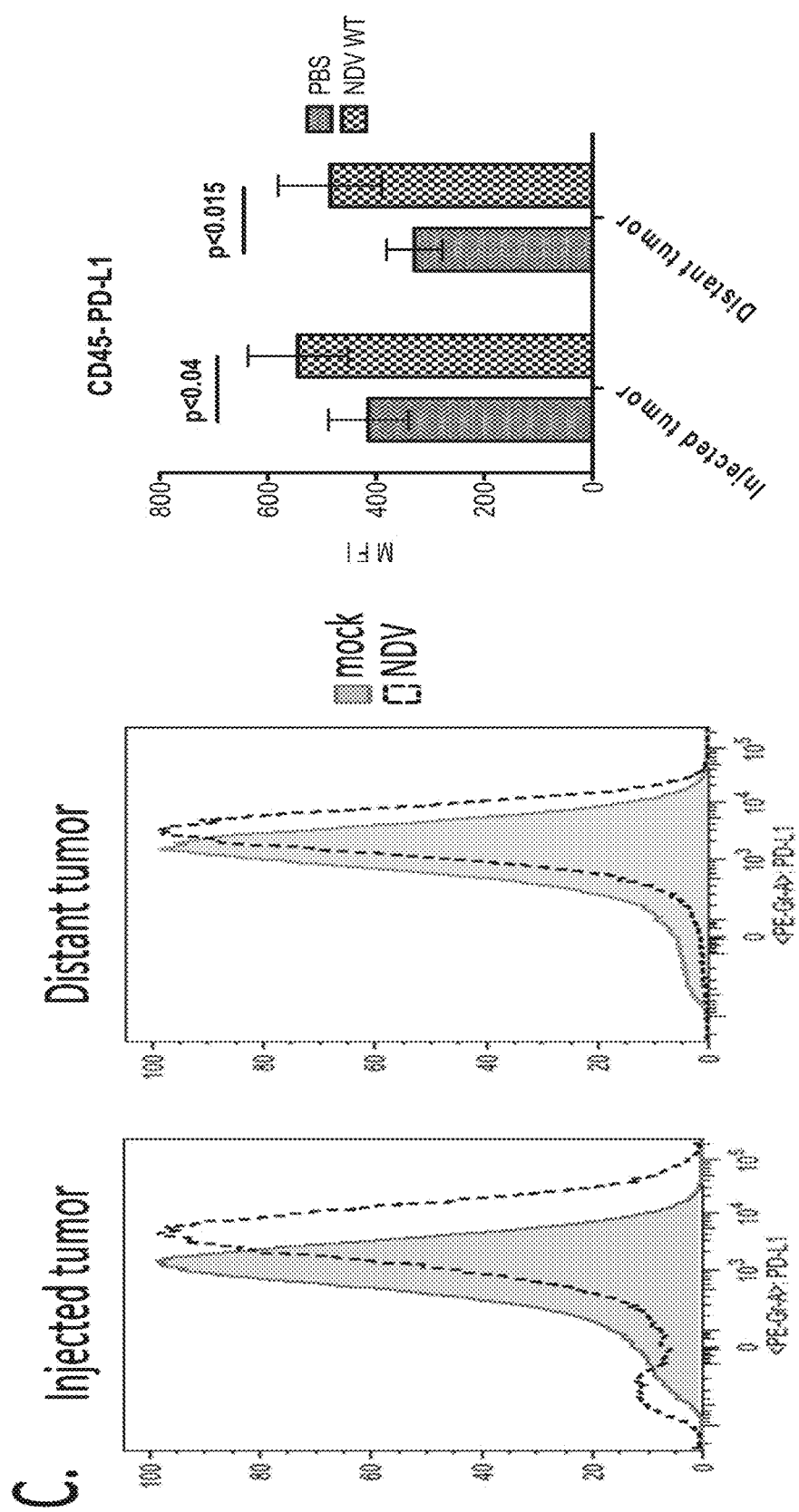
Figures 10A, 10B, 10C:
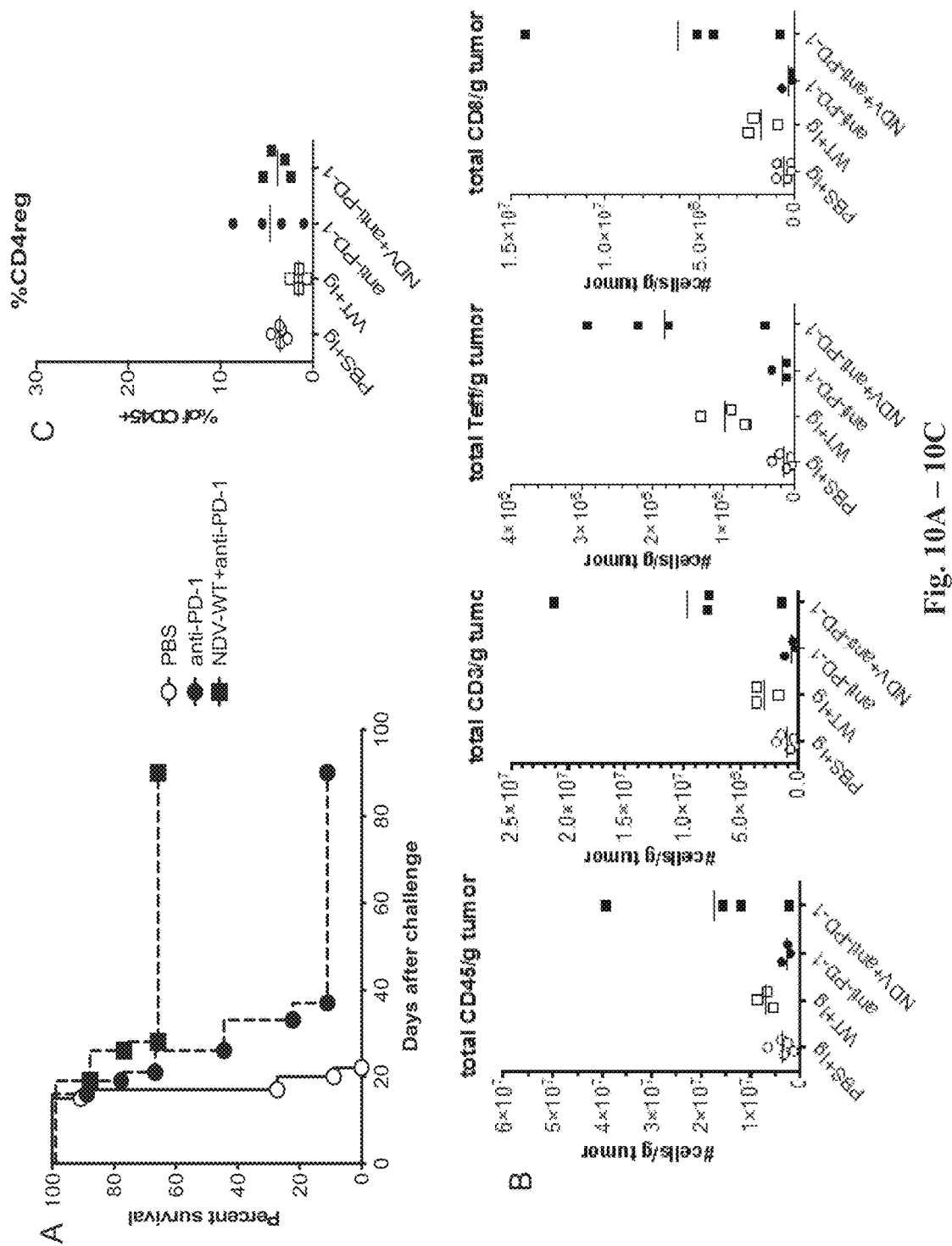
Figures 10D, 10E, 10F:
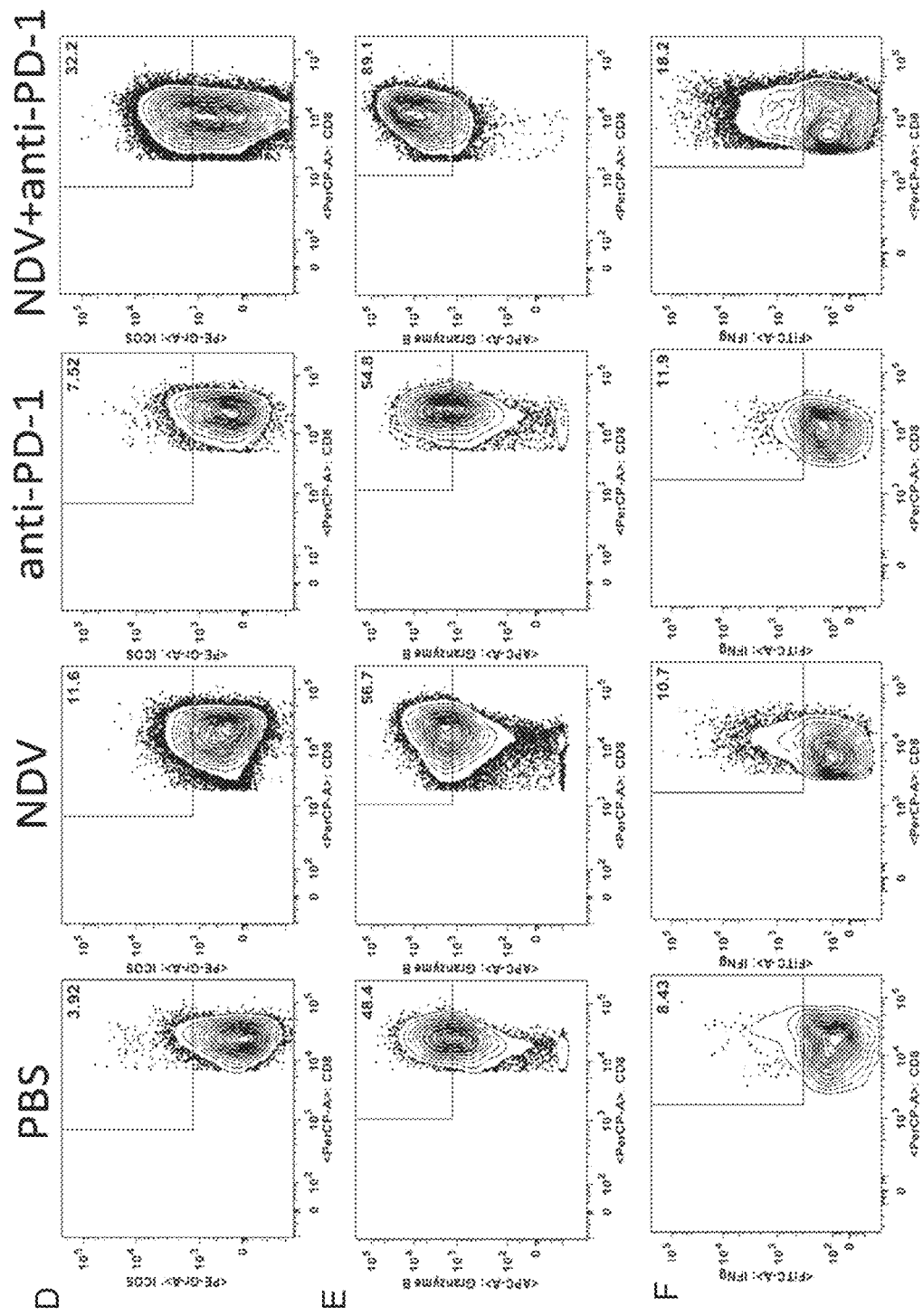

FIG. 9A-9C. NDV infection upregulates expression of PD-L1 in B16-F10 tumors. A) Surface PD-L1 expression on B16-F10 cells infected with NDV for 24 hours. B) Surface PD-L1 expression on B16-F10 cells treated with UV-inactivated supernatant from infected B16-F10 cells. C) Upregulation of PD-L1 on the surface of tumor cells isolated from injected and distant tumors from the animals treated as in FIG. 2A (2 left panels-representative flow cytometry plots, right panel-calculated averages of 5 mice per group).

FIGS. 10A-10F. Combination therapy with NDV and anti-PD-1 is effective systemically against B16 melanoma and results in increased T cell infiltration with upregulation of activation markers. A) Overall survival. Animals were treated as described in FIG. 2A with or without anti-PD-1 antibody. B) Absolute numbers of CD45, CD3, CD8, and CD4 effector cells in tumors. C) Relative percentage of regulatory T cells in tumor-infiltrating lymphocytes. D-E) Tumor-infiltrating lymphocytes from distant tumors were isolated and stained for expression of ICOS (D) and Granzyme B (E). F) Tumor infiltrating lymphocytes were re-stimulated with dendritic cells loaded with tumor lysates and assessed for expression of IFN gamma by intracellular cytokine staining.

Figure 11:
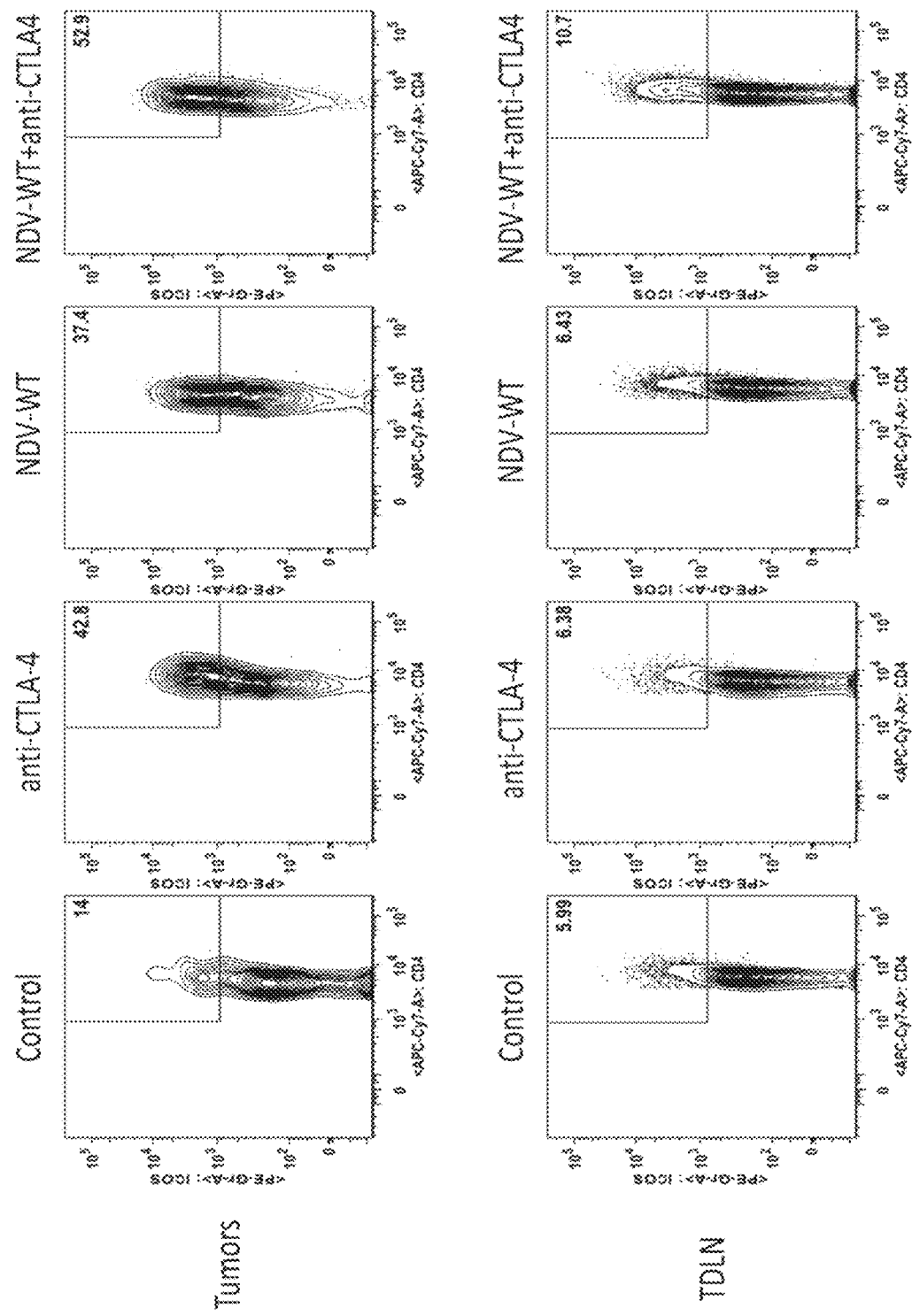
Figures 12A, 12B, 12C, 12D:
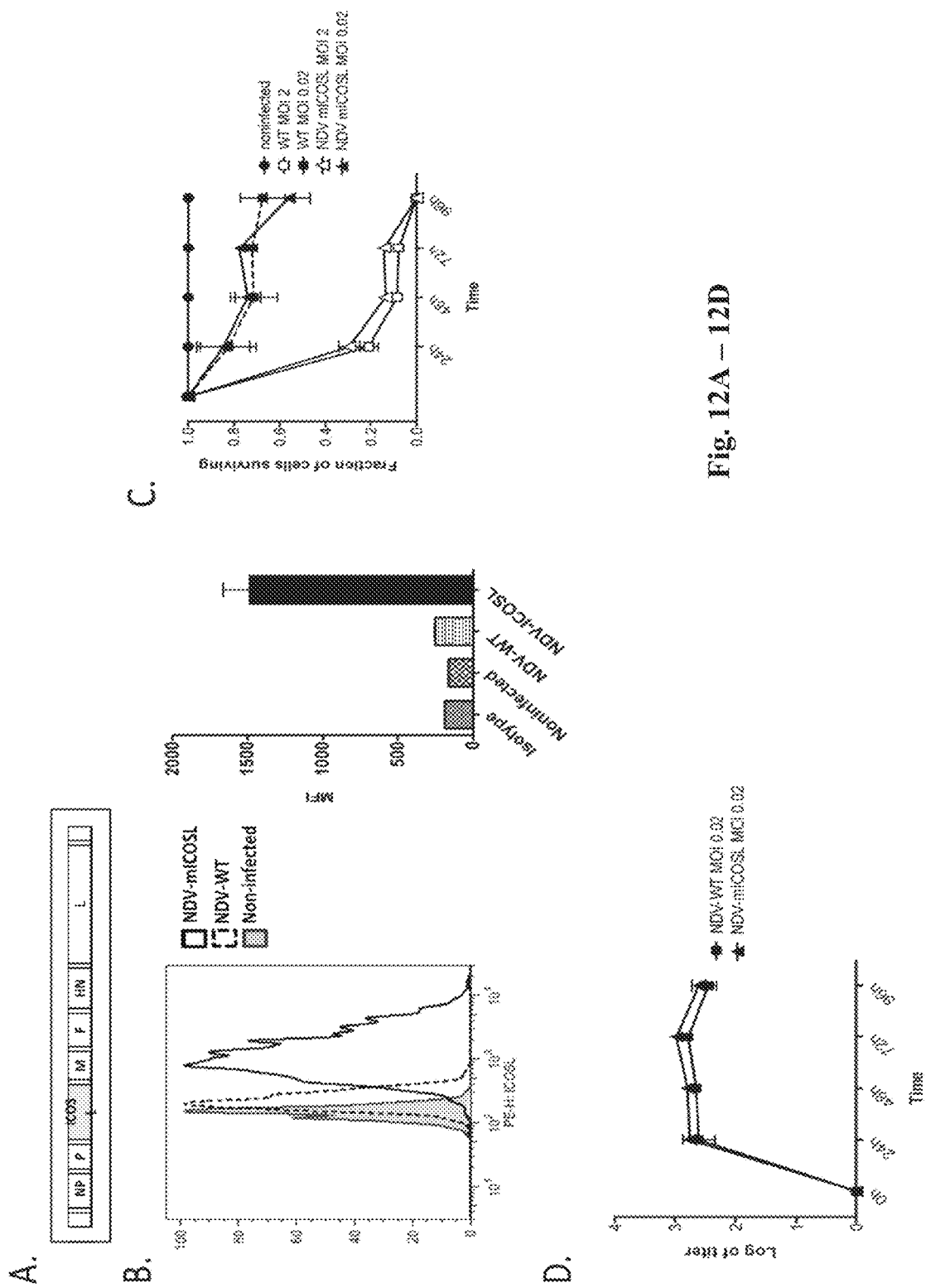

FIG. 11. Combination therapy with NDV and CTLA-4 induces upregulation of ICOS and CD4 effector cells in distant tumors and tumor-draining lymph nodes (TDLN).

FIGS. 12A-12D. Generation and in vitro evaluation of NDV-ICOSL virus. A) Viral genomic construct scheme. B) Expression of ICOSL on the surface of B16-F10 cells infected for 24 hours (representative histogram, left and average of 3 samples per group, right). C) Cytolytic activity of NDV in the infected B16-F10 cells determined by LDH assay. D) Replication of recombinant NDV in the B16-F10 cells.

Figure 13A:
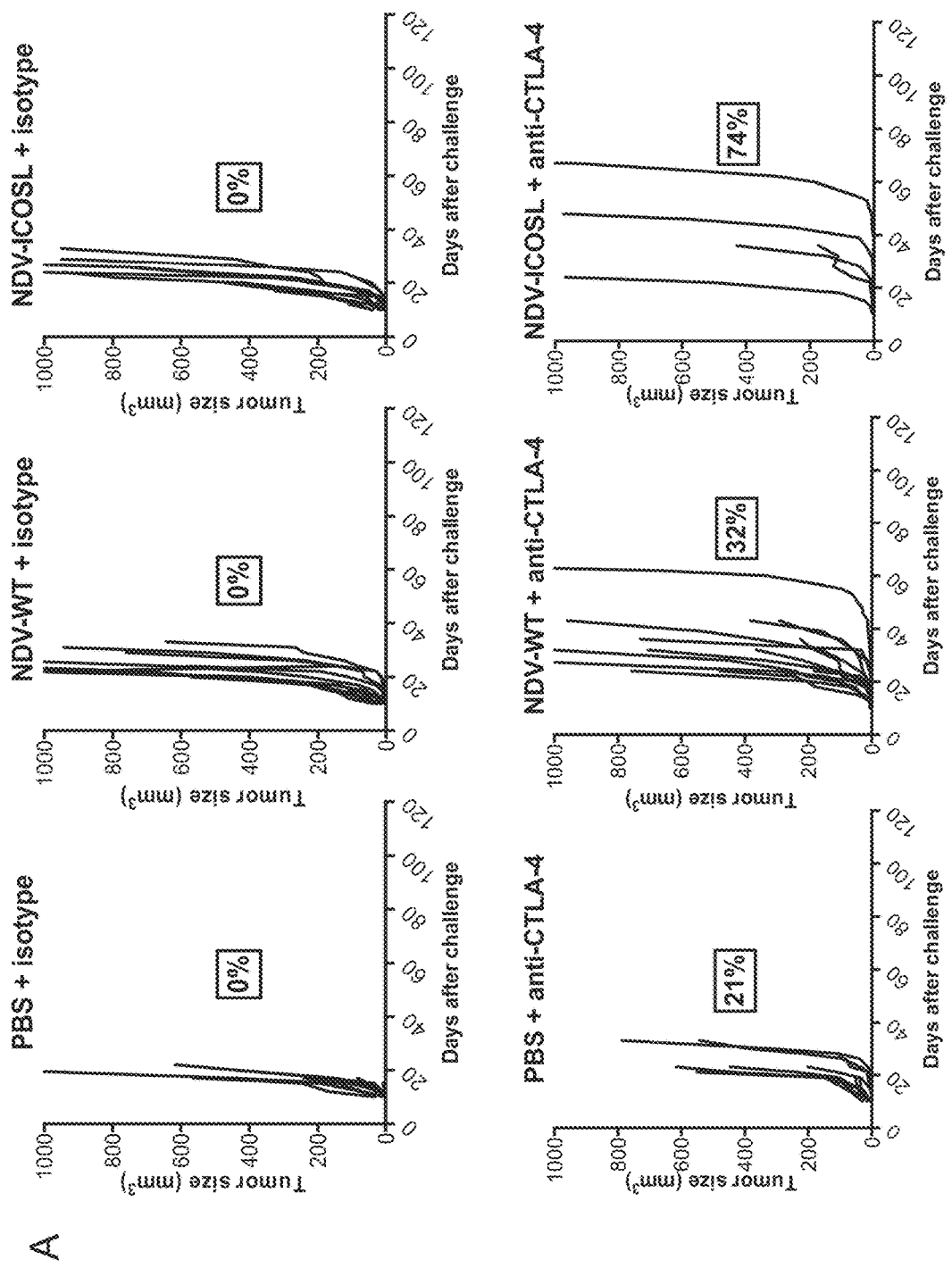
Figure 13B:
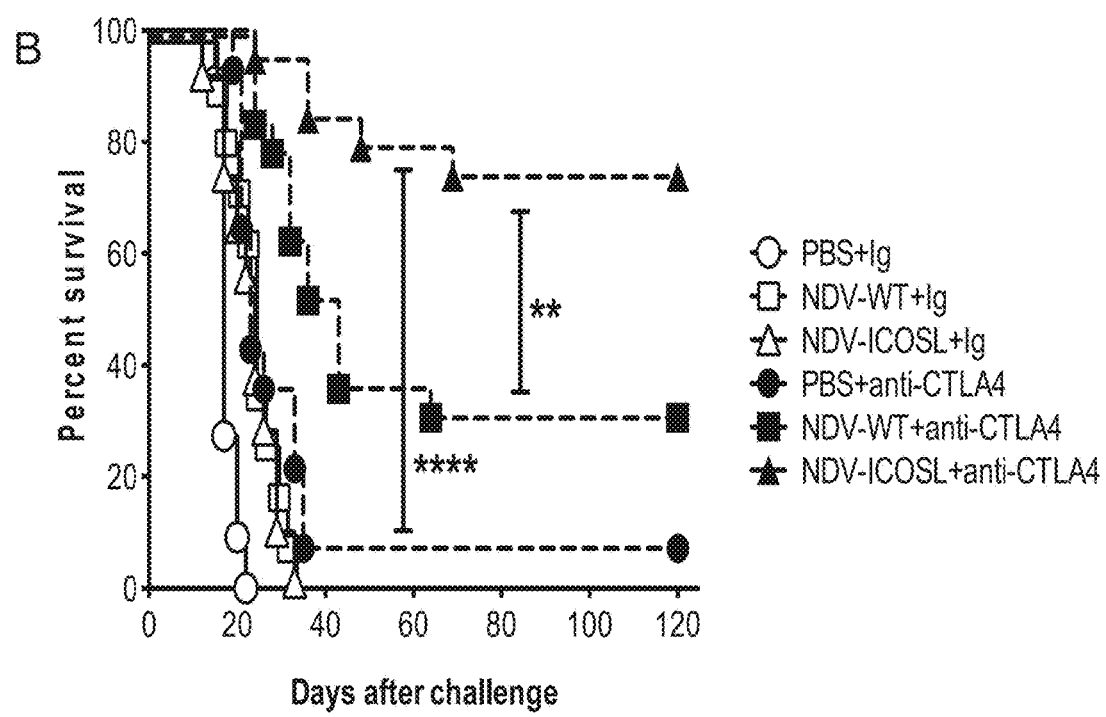
Figure 13C:
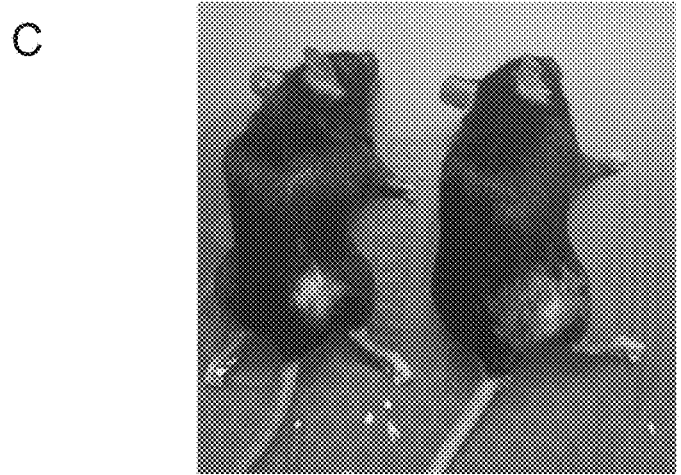

FIGS. 13A-13C. Combination therapy with NDV-mICOSL and anti-CTLA-4 protects mice from contralateral tumor challenge and results in long-term animal survival. Animals were challenged with a larger tumor dose and treated with NDV as described in FIG. 2A with or without systemic anti-CTLA-4 antibody. Growth of left flank (non-injected) tumors is shown. B) Long-term survival. Numbers in boxes indicate percent of animals protected from tumors. Pooled data of 3 different experiments of 5-10 mice per group. C) Mice treated with combination therapy develop vitiligo at the former tumor sites, but not systemically.

Figure 14A:
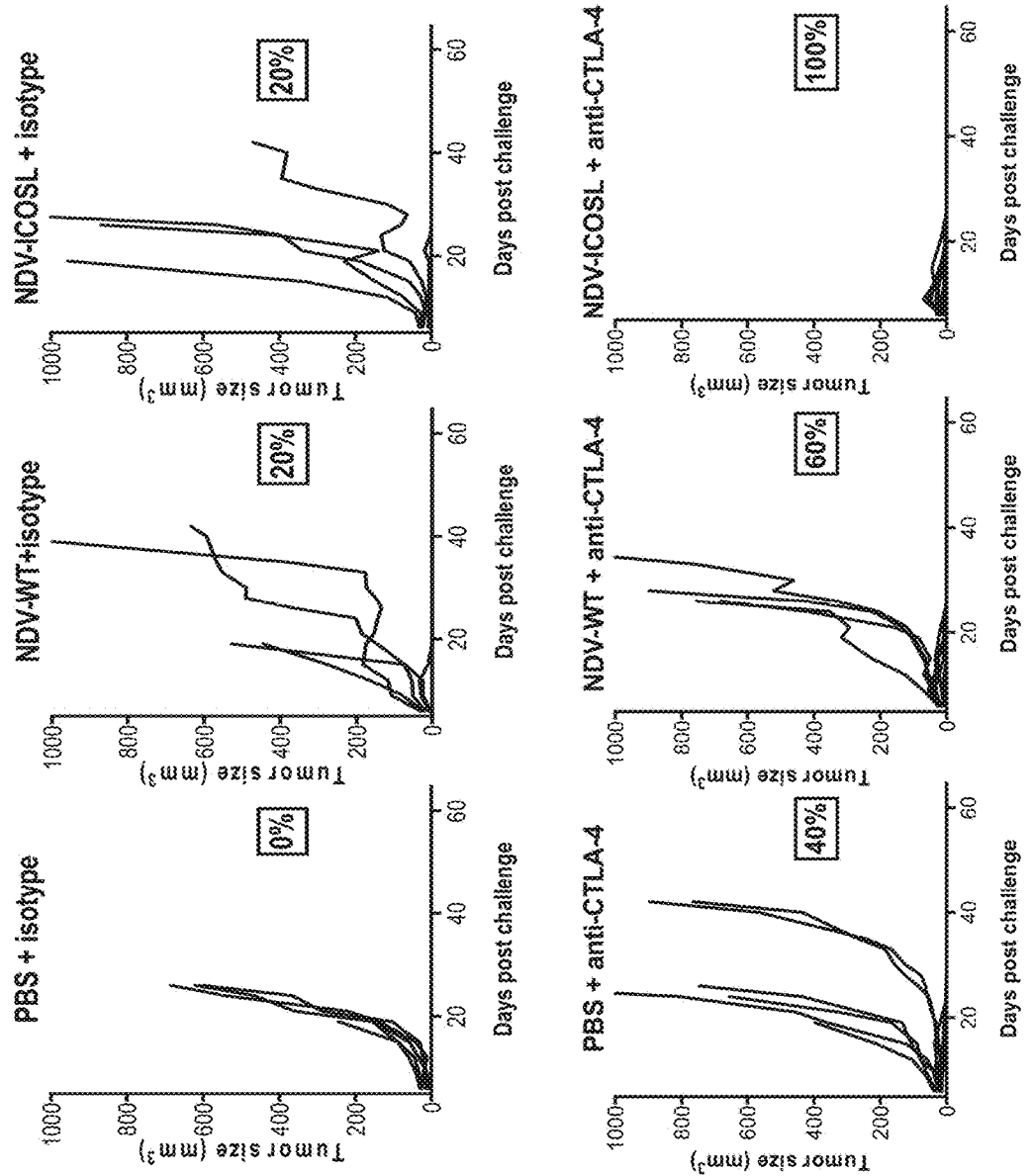
Figure 14B:
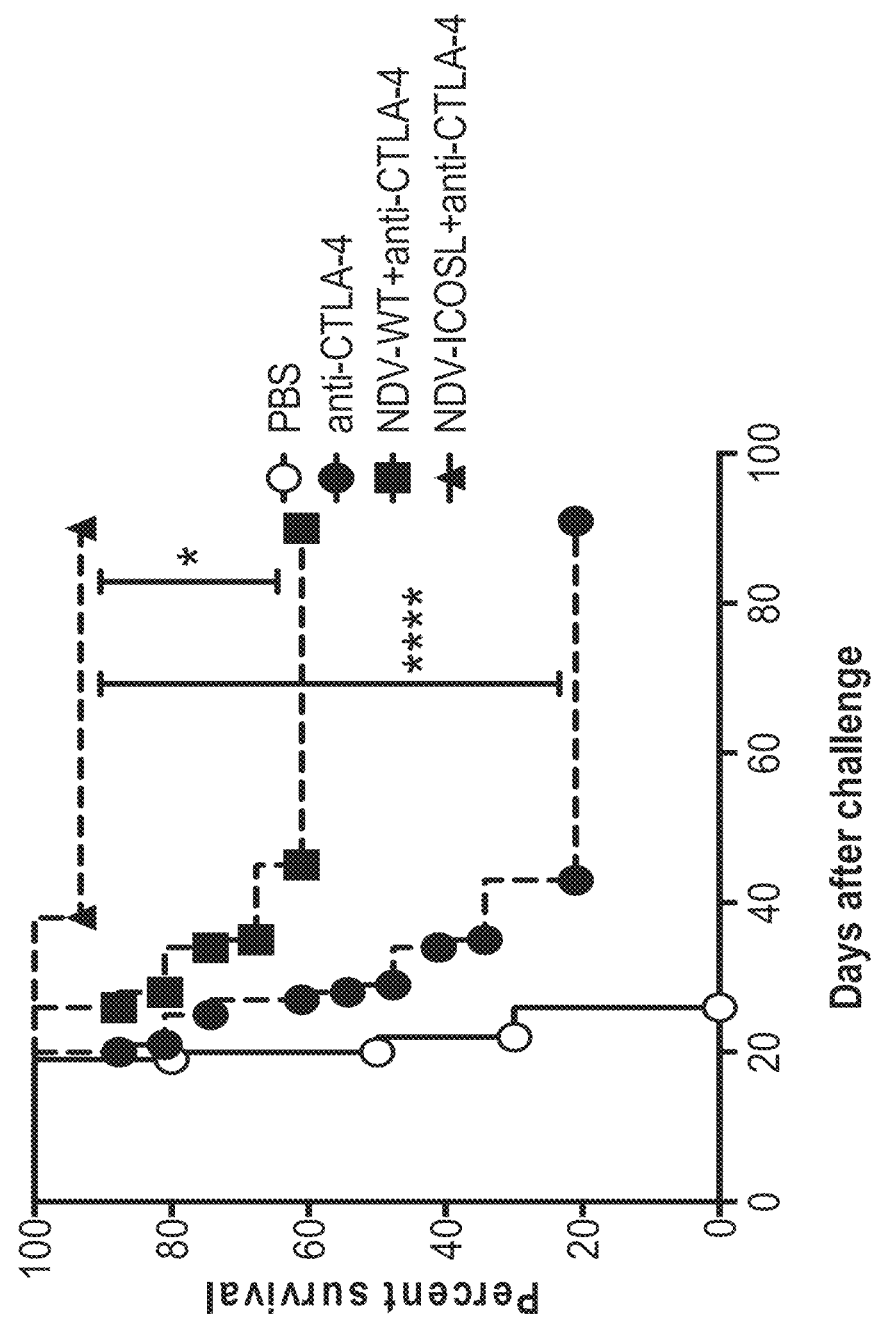

FIG. 14A-14B. Combination therapy with NDV-mICOSL and anti-CTLA-4 protects mice from contralateral tumor challenge and results in long-term animal survival in the CT26 colon carcinoma model. Animals were challenged with a larger tumor dose and treated with NDV as described in FIG. 2A with or without systemic anti-CTLA-4 antibody. Growth of left flank (non-injected) tumors is shown. Numbers in boxes indicate percent of animals protected from tumors. B) Long-term survival. Representative experiment with 5-10 mice per group (A) and pooled data of 2 different experiments of 5-10 mice per group (B).

Figure 15A:
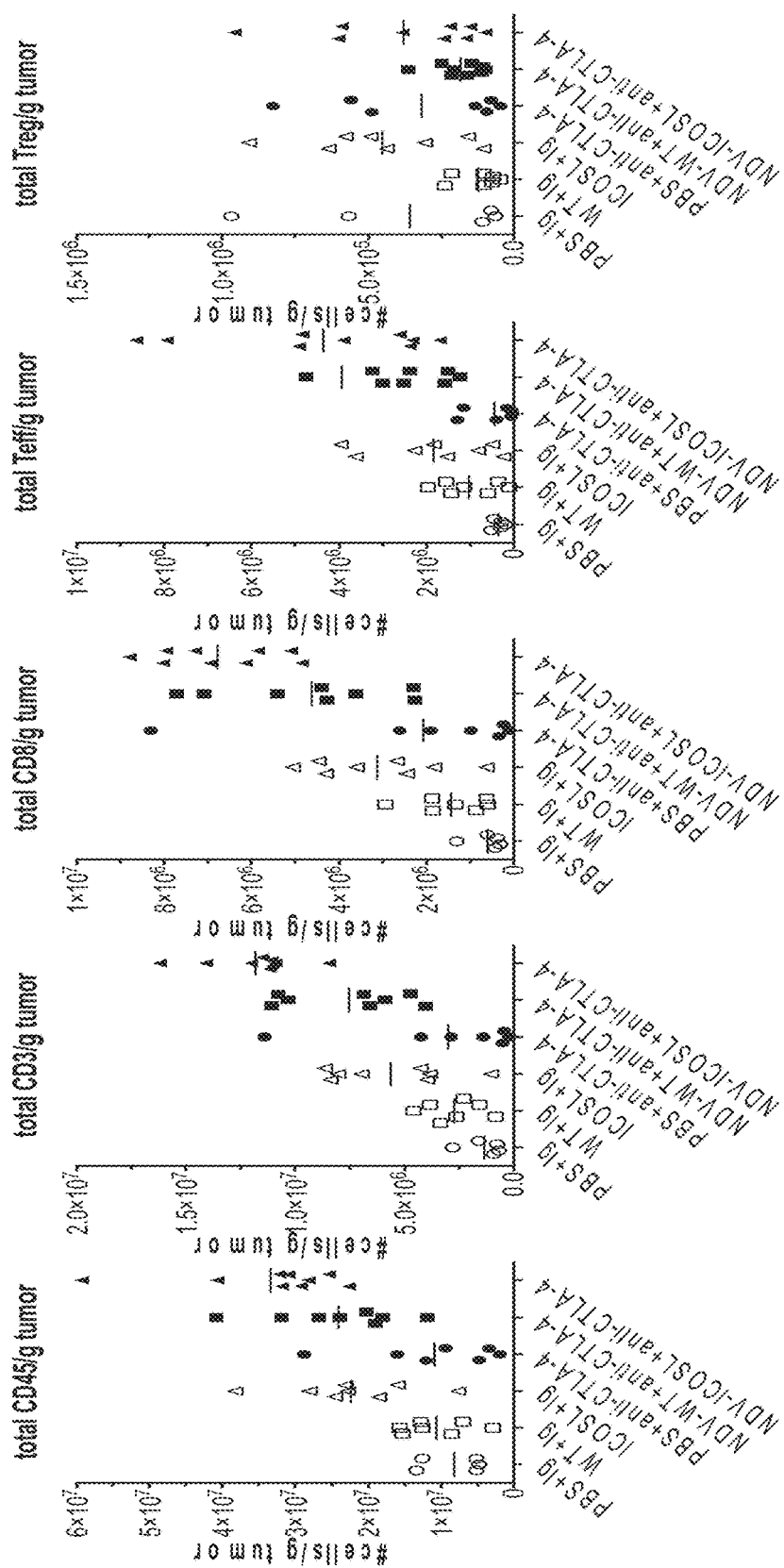
Figure 15B:
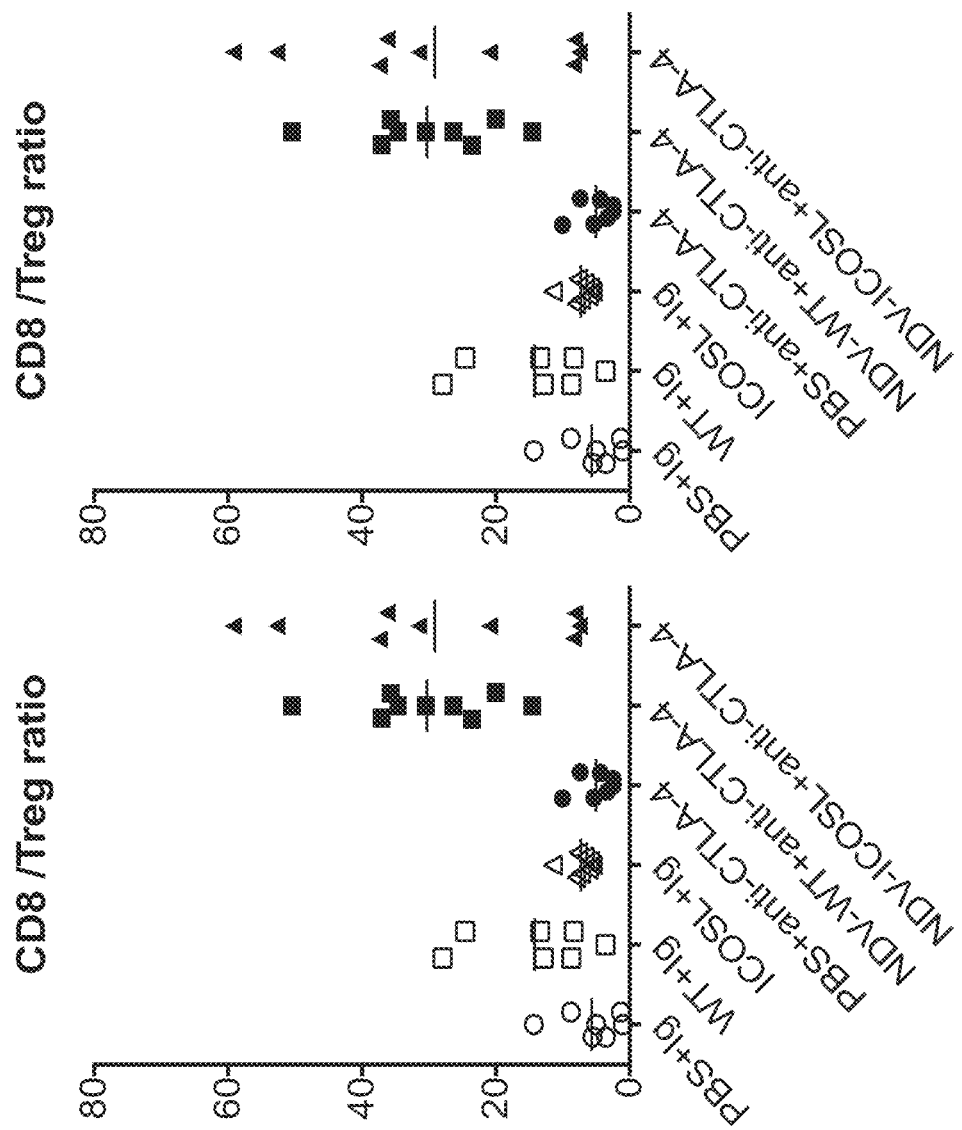
Figure 15C:
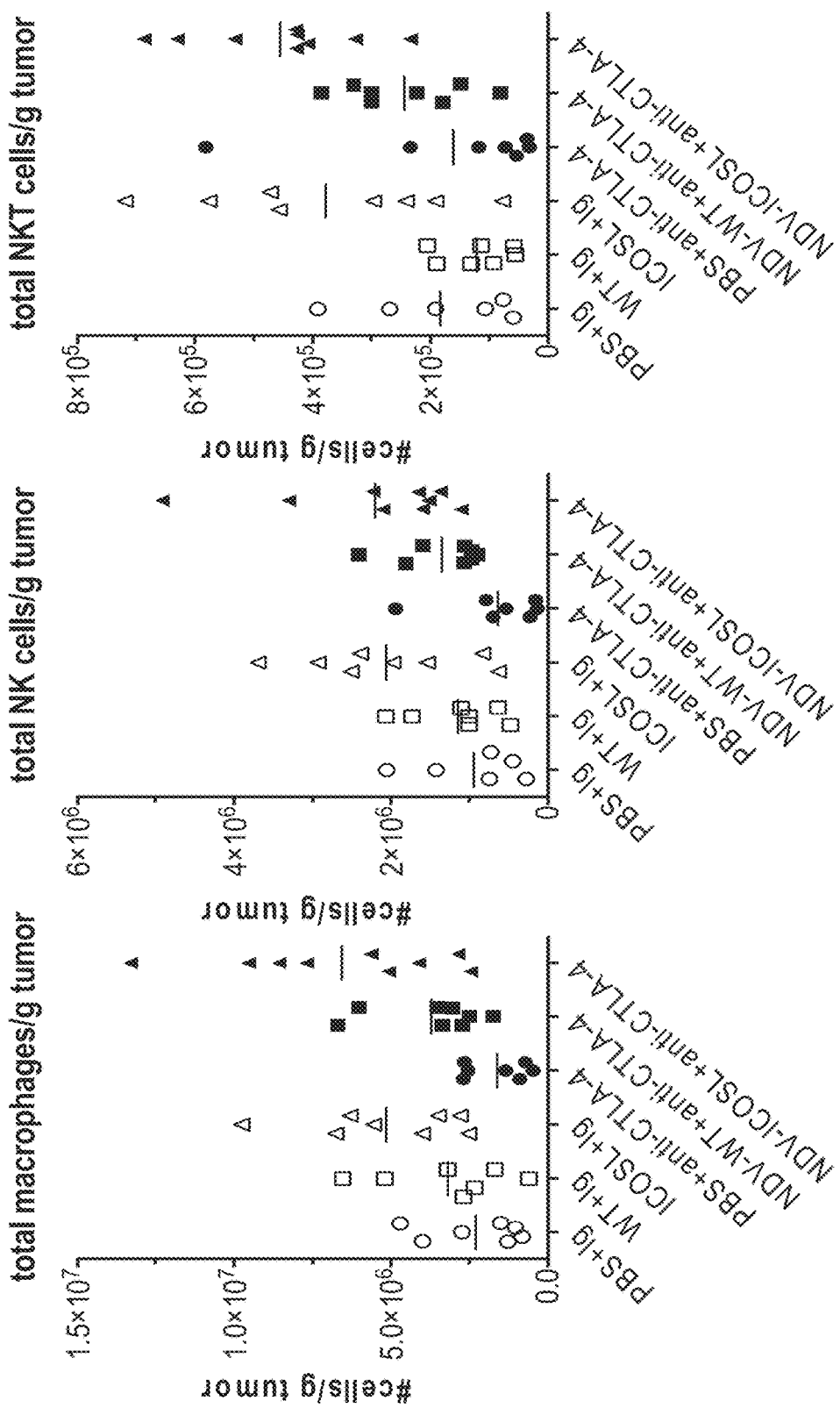

FIGS. 15A-15C. NDV treatment leads to distant B16 tumor infiltration with macrophages, NK cells, CD8 and CD4 effector cells and decreases the frequency of Tregs. A) Total CD45+, CD3+, CD8+, CD4+ FoxP3− (Teff), and CD4+ FoxP3+ (Treg) infiltrates. B) Teff/Treg and CD8/Treg ratios. C) Total macrophage, NK, and NKT cell infiltrates.

Figure 16A:
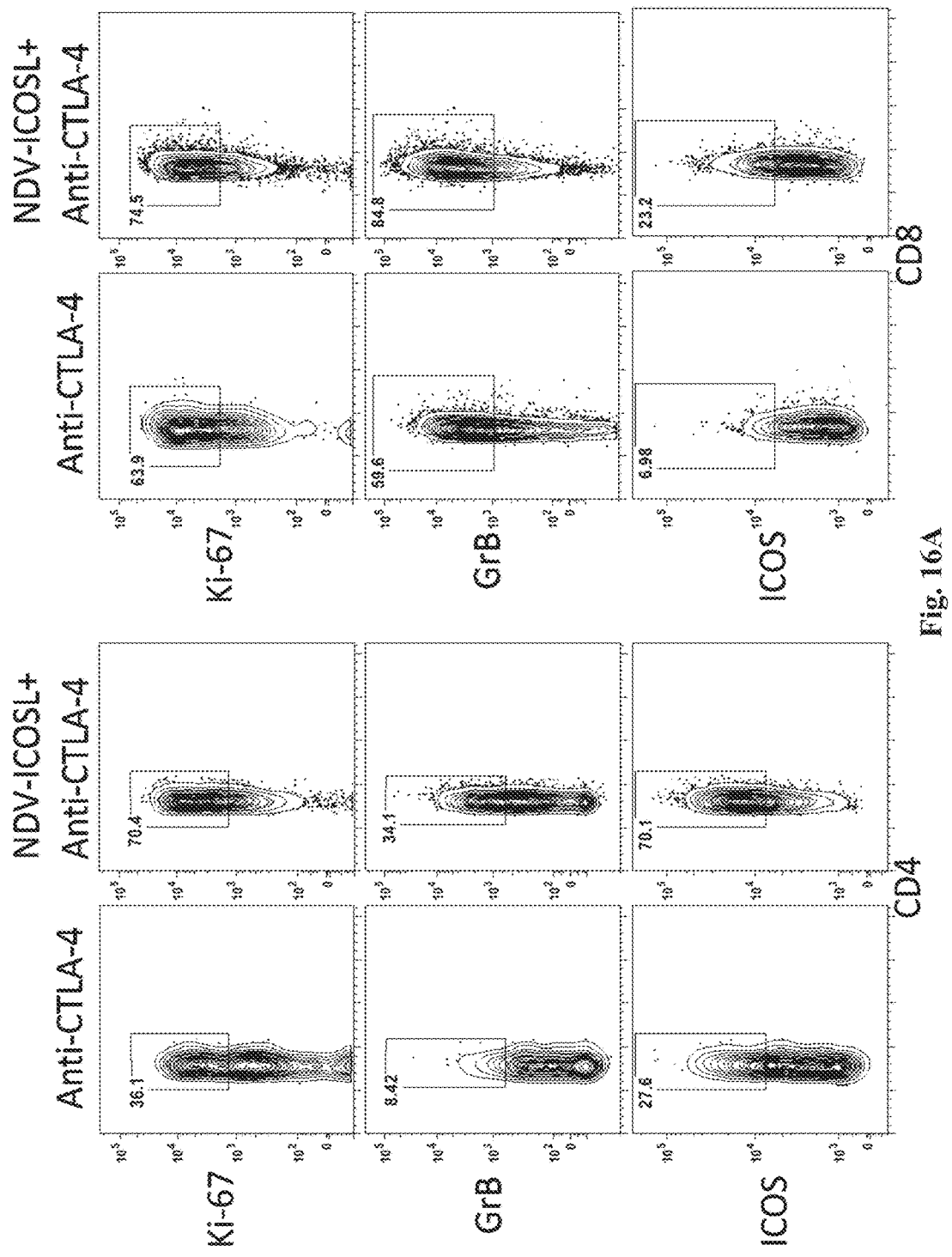
Figure 16B:
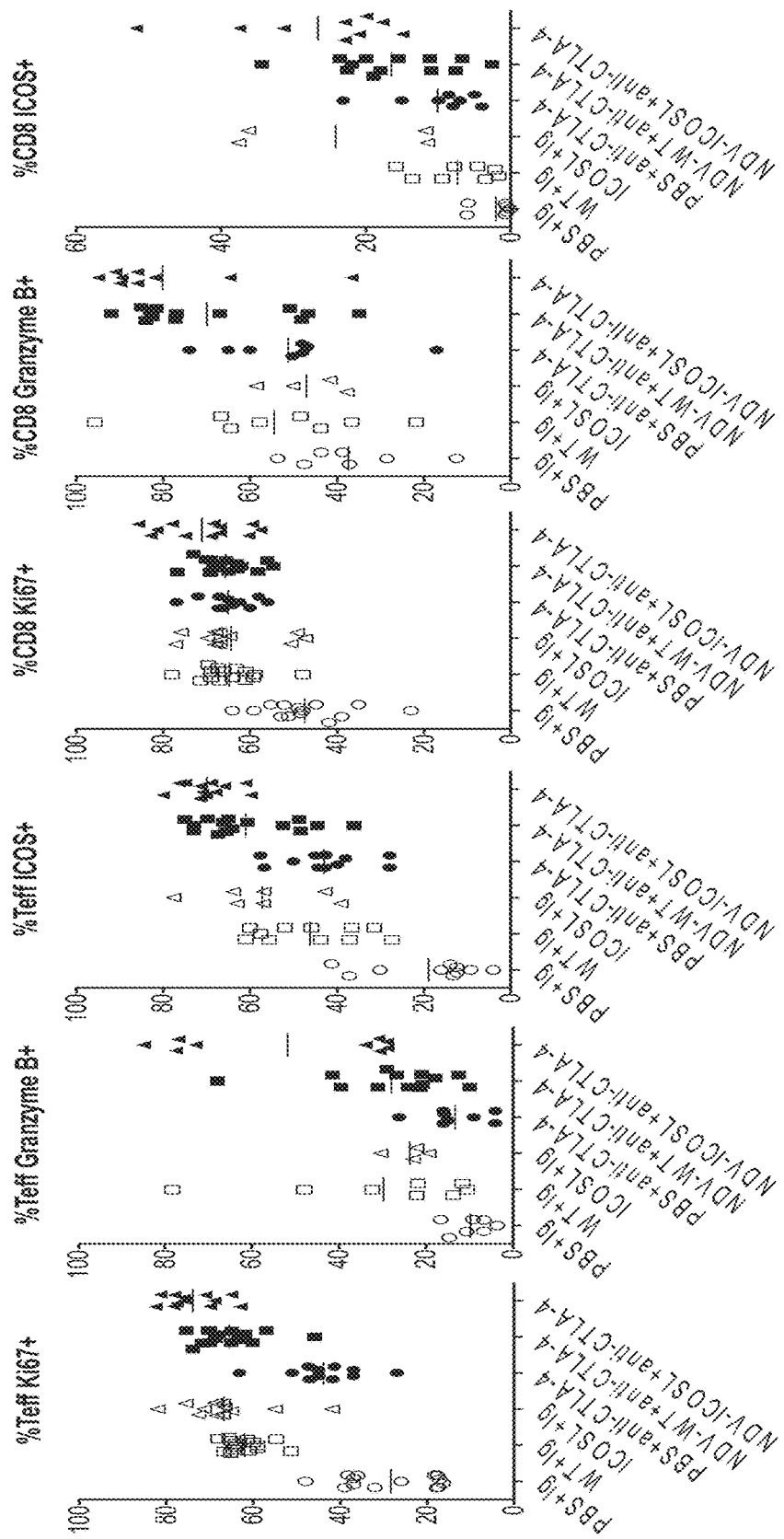

FIG. 16A-16B. Lymphocytes infiltrating distant B16 tumors upregulate activation, lytic, and proliferation markers. A) Representative Ki-67, Granzyme B (GrB) and ICOS expression plots. B) the corresponding percentages in the CD4 effector and CD8 cells.

Figure 17:
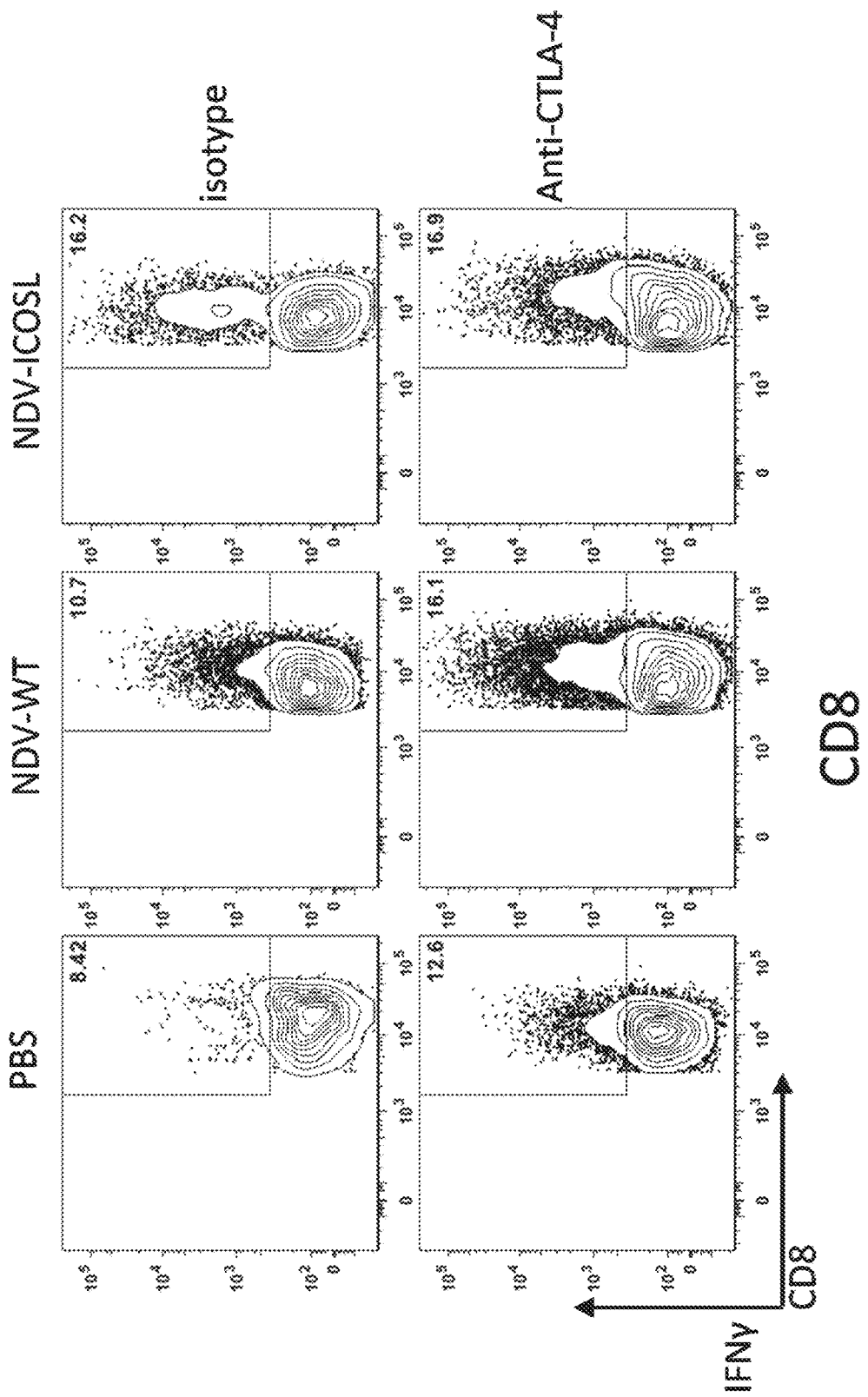

FIG. 17. Tumor infiltrating lymphocytes from treated animals secrete IFN-gamma in response to stimulation with DC's loaded with B16-F10 lysates. Representative dot plots are shown.

Figures 18A, 18B:
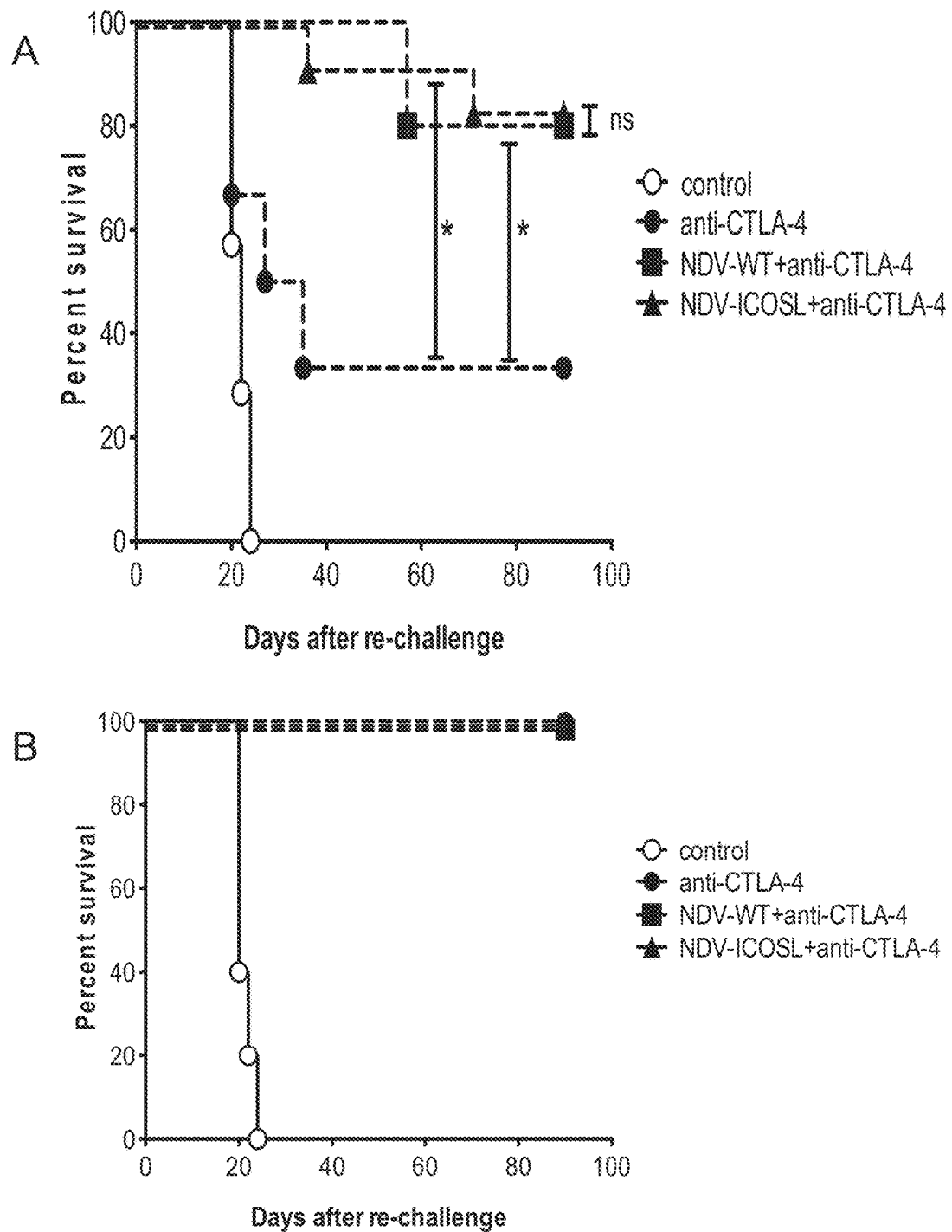

FIGS. 18A-18B. Animals cured by combination therapy are protected from further tumor challenge. A) B16-F10 melanoma, day 120 re-challenge with $1\times10^5$ cells. B) CT26 colon carcinoma, day 90 re-challenge with $1\times10^6$ cells. Representative results of two different experiments with 10 mice per group.

Figure 19A:
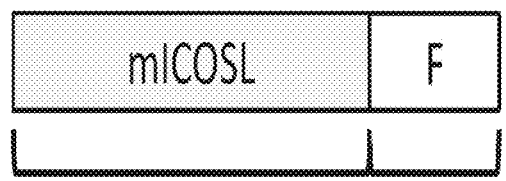
Figure 19B:
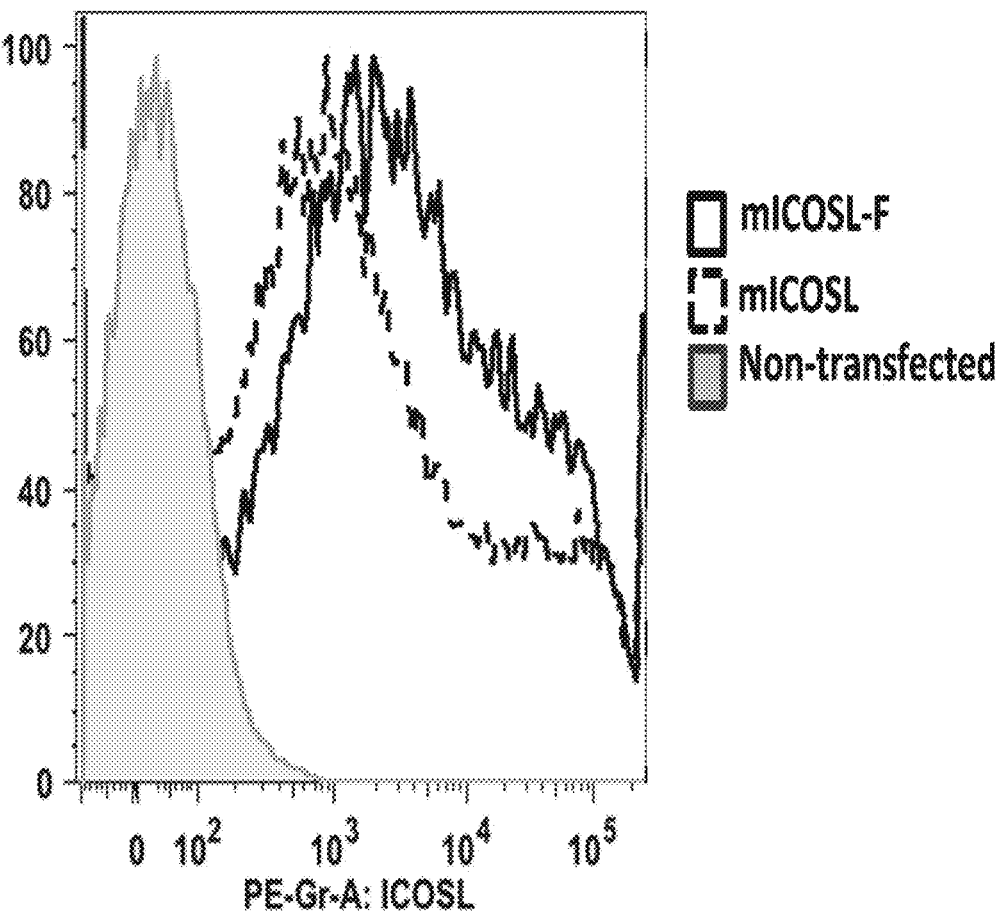

FIG. 19A-19B. Recombinant ICOSL-F chimeric protein is efficiently expressed on surface. A) Schematic diagram of the chimeric protein. B) Expression of the chimeric ICOSL-Ftm fusion protein on the surface of transfected cells.

5. DETAILED DESCRIPTION

In one aspect, presented herein are chimeric Newcastle disease viruses (NDVs) engineered to express an agonist of a co-stimulatory signal of an immune cell and/or an antagonist of an inhibitory signal of an immune cell. In a specific embodiment, presented herein are chimeric NDVs, comprising a packaged genome which encodes an agonist of a co-stimulatory signal of an immune cell, wherein the agonist is expressed. In a specific embodiment, presented herein are chimeric NDVs, comprising a packaged genome which encodes an antagonist of an inhibitory signal of an immune cell, wherein the antagonist is expressed.

In another aspect, presented herein are methods for propagating the NDVs described herein (e.g., chimeric NDVs described herein). The NDVs described herein (e.g., chimeric NDVs described herein) can be propagated in any cell, subject, tissue, organ or animal susceptible to a NDV infection.

In another aspect, presented herein are compositions comprising an NDV described herein (e.g., a chimeric NDV described herein). In a specific embodiment, presented herein are pharmaceutical compositions comprising an NDV described herein (e.g., a chimeric NDV described herein) and a pharmaceutically acceptable carrier. In another embodiment, presented herein are pharmaceutical compositions comprising cancer cells infected with an NDV described herein (e.g., a chimeric NDV described herein), and a pharmaceutically acceptable carrier. In another embodiment, presented herein are pharmaceutical compositions comprising protein concentrate from lysed NDV-infected cancer cells (e.g., chimeric-NDV infected cancer cells), and a pharmaceutically acceptable carrier.

In another aspect, presented herein are methods for producing pharmaceutical compositions comprising an NDV described herein (e.g., a chimeric NDV described herein). In one embodiment, a method for producing a pharmaceutical composition comprises: (a) propagating an NDV described herein (e.g., a chimeric NDV described herein) in a cell line that is susceptible to an NDV infection; and (b) collecting the progeny virus, wherein the virus is grown to sufficient quantities and under sufficient conditions that the virus is free from contamination, such that the progeny virus is suitable for formulation into a pharmaceutical composition. In another embodiment, a method for producing a pharmaceutical composition comprises: (a) propagating an NDV described herein (e.g., a chimeric NDV described herein) in an embryonated egg; and (b) collecting the progeny virus, wherein the virus is grown to sufficient quantities and under sufficient conditions that the virus is free from contamination, such that the progeny virus is suitable for formulation into a pharmaceutical composition.

In another aspect, presented herein are methods for treating cancer utilizing a chimeric NDV described herein (e.g., a chimeric NDV described in Section 5.2, infra) or a composition comprising such a chimeric NDV. In a specific embodiment, a method for treating cancer comprises infecting a cancer cell in a subject with a chimeric NDV described herein (e.g., a chimeric NDV described in Section 5.2, infra) or a composition thereof. In another embodiment, a method for treating cancer comprises administering to a subject in need thereof a chimeric NDV described herein (e.g., a chimeric NDV described in Section 5.2, infra) or a composition thereof. In specific embodiments, an effective amount of a chimeric NDV described herein (e.g., a chimeric NDV described in Section 5.2, infra) or a composition comprising an effective amount of a chimeric NDV described herein is administered to a subject to treat cancer. In specific embodiments, the chimeric NDV comprises a packaged genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell), wherein the agonist and/or antagonist are expressed by the NDV. In certain embodiments, the genome of the NDV also comprises a mutated F protein. In certain embodiments, two or more chimeric NDVs are administered to a subject to treat cancer.

In another embodiment, a method for treating cancer comprises administering to a subject in need thereof cancer cells infected with a chimeric NDV described herein (e.g., a chimeric NDV described in Section 5.2, infra) or composition thereof. In specific embodiments, the cancer cells have been treated with gamma radiation prior to administration to the subject or incorporation into the composition. In another embodiment, a method for treating cancer comprises administering to a subject in need thereof a protein concentrate or plasma membrane fragments from cancer cells infected with a chimeric NDV (e.g., a chimeric NDV described in Section 5.2, infra) or a composition thereof. In specific embodiments, the chimeric NDV comprises a packaged genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell), wherein the agonist and/or antagonist are expressed by the NDV. In certain embodiments, the genome of the NDV also comprises a mutated F protein, which is expressed by the NDV.

In another aspect, presented herein are methods for treating cancer utilizing an NDV described herein (e.g., a chimeric NDV such as described in Section 5.2, infra) or a composition comprising such the NDV in combination with one or more other therapies. In one embodiment, presented herein are methods for treating cancer comprising administering to a subject an NDV described herein (e.g., a chimeric NDV, such as described in Section 5.2, infra) and one or more other therapies. In another embodiment, presented herein are methods for treating cancer comprising administering to a subject an effective amount of an NDV described herein or a composition comprising an effective amount of an NDV described herein, and one or more other therapies. The NDV and one or more other therapies can be administered concurrently or sequentially to the subject. In certain embodiments, the NDV and one or more other therapies are administered in the same composition. In other embodiments, the NDV and one or more other therapies are administered in different compositions. The NDV and one or more other therapies can be administered by the same or different routes of administration to the subject.

Any NDV type or strain may be used in a combination therapy disclosed herein, including, but not limited to, naturally-occurring strains, variants or mutants, mutagenized viruses, reassortants and/or genetically engineered viruses. In a specific embodiment, the NDV used in a combination with one or more other therapies is a naturally-occurring strain. In another embodiment, the NDV used in combination with one or more other therapies is a chimeric NDV. In a specific embodiment, the chimeric NDV comprises a packaged genome, the genome comprising a cytokine (e.g., IL-2, IL-7, IL-15, IL-17 or IL-21). In specific embodiments, the chimeric NDV comprises a packaged genome, the genome comprising a tumor antigen. In specific embodiments, the tumor antigen is expressed by cells infected with the chimeric NDV. In another specific embodiment, the chimeric NDV comprises a packaged genome, the genome comprising a pro-apoptotic molecule (e.g., Bax, Bak, Bad, BID, Bcl-xS, Bim, Noxa, Puma, AIF, FasL, and TRAIL) or an anti-apoptotic molecule (e.g., Bcl-2, Bcl-xL, Mcl-1, and XIAP). In specific embodiments, the pro-apoptotic molecule or anti-apoptotic molecule is expressed by cells infected with the chimeric NDV. In another specific embodiment, the chimeric NDV comprises a packaged genome, the genome comprising an agonist of a co-stimulatory signal of an immune cell (e.g., an agonist of a co-stimulatory receptor of an immune cell) and/or an antagonist of an inhibitory signal of an immune cell (e.g., an antagonist of an inhibitory receptor of an immune cell). In specific embodiments, the agonist and/or antagonist are expressed by cells infected with the chimeric NDV. In certain embodiments, the genome of the NDV also comprises a mutated F protein, a tumor antigen, a heterologous interferon antagonist, a pro-apoptotic molecule and/or an anti-apoptotic molecule. In certain embodiments, the one or more therapies used in combination with an NDV described herein is one or more other therapies described in Section 5.6.4, infra. In particular embodiments, the one or more therapies used in combination with an NDV described herein are an agonist of a co-stimulatory signal of an immune cell and/or an antagonist of an inhibitory signal of an immune cell. See, e.g., Section 5.2.1, infra, for examples of agonists of a co-stimulatory signal of an immune cell and antagonists of an inhibitory signal of an immune cell. In a specific embodiment, the antagonist of an inhibitory signal of an immune cell is the anti-CTLA-4 antibody described in Section 6, infra. In another specific embodiment, the agonist of a co-stimulatory signal of an immune cell is the ICOS ligand described in Section 6, infra

5.1 Newcastle Disease Virus

Any NDV type or strain may be used in a combination therapy disclosed herein, including, but not limited to, naturally-occurring strains, variants or mutants, mutagenized viruses, reassortants and/or genetically engineered viruses. In a specific embodiment, the NDV used in a combination therapy disclosed herein is a naturally-occurring strain. In certain embodiments, the NDV is a lytic strain. In other embodiments, the NDV used in a combination therapy disclosed herein is a non-lytic strain. In certain embodiments, the NDV used in a combination therapy disclosed herein is lentogenic strain. In some embodiments, the NDV is a mesogenic strain. In other embodiments, the NDV used in a combination therapy disclosed herein is a velogenic strain. Specific examples of NDV strains include, but are not limited to, the 73-T strain, NDV HUJ strain, Ulster strain, MTH-68 strain, Italien strain, Hickman strain, PV701 strain, Hitchner B1 strain (see, e.g., Genbank No. AF309418 or NC_002617), La Sota strain (see, e.g., Genbank No. AY845400), YG97 strain, MET95 strain, Roakin strain, and F48E9 strain. In a specific embodiment, the NDV used in a combination therapy disclosed herein that is the Hitchner B1 strain. In another specific embodiment, the NDV used in a combination therapy disclosed herein is a B1 strain as identified by Genbank No. AF309418 or NC_002617. In another specific embodiment, the NDV used in a combination therapy disclosed herein is the NDV identified by ATCC No. VR2239. In another specific embodiment, the NDV used in a combination therapy disclosed herein is the La Sota strain.

In specific embodiments, the NDV used in a combination therapy disclosed herein is not pathogenic birds as assessed by a technique known to one of skill. In certain specific embodiments, the NDV used in a combination therapy is no pathogenic as assessed by intracranial injection of 1-day-old chicks with the virus, and disease development and death as scored for 8 days. In some embodiments, the NDV used in a combination therapy disclosed herein has an intracranial pathogenicity index of less than 0.7, less than 0.6, less than 0.5, less than 0.4, less than 0.3, less than 0.2 or less than 0.1. In certain embodiments, the NDV used in a combination therapy disclosed herein has an intracranial pathogenicity index is zero.

In certain embodiments, the NDV used in a combination therapy disclosed herein is a mesogenic strain that has been genetically engineered so as not be a considered pathogenic in birds as techniques known to one skilled in the art. In certain embodiments, the NDV used in a combination therapy disclosed herein is a velogenic strain that has been genetically engineered so as not be a considered pathogenic in birds as techniques known to one skilled in the art.

In certain embodiments, the NDV used in a combination therapy disclosed herein expresses a mutated F protein. In a specific embodiment, the NDV used in a combination therapy expresses a mutated F protein is highly fusogenic and able to form syncytia. In another specific embodiment, the mutated F protein is incorporated into the virion.

In one embodiment, a genome of a NDV used in a combination therapy disclosed herein is engineered to express a mutated F protein with a mutated cleavage site. In a specific embodiment, the NDV used in a combination therapy disclosed herein is engineered to express a mutated F protein in which the cleavage site of the F protein is mutated to produce a polybasic amino acid sequence, which allows the protein to be cleaved by intracellular proteases, which makes the virus more effective in entering cells and forming syncytia. In another specific embodiment, the NDV used in a combination therapy disclosed herein is engineered to express a mutated F protein in which the cleavage site of the F protein is replaced with one containing one or two extra arginine residues, allowing the mutant cleavage site to be activated by ubiquitously expressed proteases of the furin family. Specific examples of NDVs that express such a mutated F protein include, but are not limited to, rNDV/F2aa and rNDV/F3aa. For a description of mutations introduced into a NDV F protein to produce a mutated F protein with a mutated cleavage site, see, e.g., Park et al. (2006) Engineered viral vaccine constructs with dual specificity: avian influenza and Newcastle disease. PNAS USA 103: 8203-2808, which is incorporated herein by reference in its entirety. In some embodiments, the NDV used in a combination therapy disclosed herein is engineered to express a mutated F protein with the amino acid mutation L289A. In specific embodiments the L289A mutated F protein possesses one, two or three arginine residues in the cleavage site. In certain embodiments, the mutated F protein is from a different type or strain of NDV than the backbone NDV. In some embodiments, the mutated F protein is in addition to the backbone NDV F protein. In specific embodiments, the mutated F protein replaces the backbone NDV F protein.

In certain embodiments, the NDV used in a combination therapy disclosed herein is attenuated such that the NDV remains, at least partially, infectious and can replicate in vivo, but only generate low titers resulting in subclinical levels of infection that are non-pathogenic (see, e.g., Khattar et al., 2009, J. Virol. 83:7779-7782). In a specific embodiment, the NDV is attenuated by deletion of the V protein. Such attenuated NDVs may be especially suited for embodiments wherein the virus is administered to a subject in order to act as an immunogen, e.g., a live vaccine. The viruses may be attenuated by any method known in the art.

In certain embodiments, the NDV used in a combination therapy disclosed herein does not comprise an NDV V protein encoding sequence. In other embodiments, the NDV used in a combination therapy disclosed herein expresses a mutated V protein. See, e.g., Elankumaran et al., 2010, J. Virol. 84(8): 3835-3844, which is incorporated herein by reference, for examples of mutated V proteins. In certain embodiments, a mesogenic or velogenic NDV strain used in a combination therapy disclosed herein expresses a mutated V protein, such as disclosed by Elankumaran et al., 2010, J. Virol. 84(8): 3835-3844.

In certain embodiments, the NDV used in a combination therapy disclosed herein is an NDV disclosed in U.S. Pat. No. 7,442,379, U.S. Pat. No. 6,451,323, or U.S. Pat. No. 6,146,642, which is incorporated herein by reference in its entirety. Genetically engineered Newcastle disease viruses and viral vectors which express heterologous genes or mutated Newcastle disease viral genes or a combination of viral genes derived from different strains of Newcastle disease virus are described. The construction and use of recombinant negative strand NDV viral RNA templates which may be used with viral RNA-directed RNA polymerase to express heterologous gene products in appropriate host cells and/or to rescue the heterologous gene in virus particles. In a specific embodiment of the invention, the heterologous gene product is a peptide or protein derived from the genome of a human immunodeficiency virus. The RNA templates may be prepared either in vitro or in vivo by transcription of appropriate DNA sequences using a DNA-directed RNA polymerase such as bacteriophage T7, T3, the SP6 polymerase or a eukaryotic polymerase such as polymerase I.

The recombinant RNA templates may be used to transfect continuous/transfected cell lines that express the RNA-directed RNA polymerase proteins allowing for complementation, as demonstrated by way of working examples in which RNA transcripts of cloned DNA containing the coding region—in negative sense orientation—of the chloramphenicol acetyltransferase (CAT) gene, flanked by the 5' terminal and the 3' terminal nucleotides of the NDV-CL (California strain/11914/1944-like strain) (Meindl et al., 1974 Virology 58: 457-463) RNA were transfected into cells expressing the NDV polymerase proteins. In a preferred embodiment, a non-virus dependent replication system is used to recover chimeric NDV, in which plasmid DNA encoding the NDV genome or antigenome is coexpressed with plasmid DNA encoding the minimum subset of Newcastle disease virus proteins needed for specific replication and expression of the virus, as demonstrated by way of working example as described in U.S. Pat. No. 7,442,379.

The ability to reconstitute NDV in vivo allows the design of novel chimeric NDV viruses which express foreign genes or which express mutant NDV genes. The ability to reconstitute NDV in vivo also allows the design of novel chimeric NDVs which express genes from different strains of NDV. One way to achieve this goal involves modifying existing NDV genes. For example, the HN gene may be modified to contain foreign sequences in its external domains. Where the heterologous sequence are epitopes or antigens of pathogens, these chimeric viruses may be used to induce a protective immune response against the disease agent from which these determinants are derived.

In accordance with the present invention, a chimeric RNA is constructed in which a coding sequence derived from the gp160 coding region of human immunodeficiency virus is inserted into the HN coding sequence of NDV, and chimeric virus produced from transfection of this chimeric RNA segment into a host cell infected with wild-type NDV. Further, such a chimeric virus should be capable of eliciting both a vertebrate humoral and cell-mediated immune response. Further described are the induction of interferon and related pathways by recombinant or chimeric NDV viruses.

In yet another embodiment, virtually any heterologous sequence may be constructed into the chimeric viruses of the present invention, including but not limited to antigens, such as 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

Antigens that are allergens are generally proteins or glycoproteins, including antigens derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an NDV gene coding sequence such that a chimeric gene product is expressed which contains the heterologous peptide sequence within the NDV viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, interleukin-1, -2, -4, -5, -6, -12.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to influenza glycoproteins, in particular, hemagglutinin H5, H7, Marek's Disease Viral epitopes; epitopes of Infectious Bursal Disease Virus (IBDV), Infectious Bronchitis Virus (IBV), Chicken Anemia Virus (CAV), Infectious Laryngotracheitis Virus (ILV), Avian Leukosis Virus (ALV), Reticuloendotheliosis Virus (RV), Avian Influenza Virus (AIV), rabies virus, feline leukemia virus, canine distemper virus, vesicular stomatitis virus, rinderpest virus, and swinepox virus (see Fields et al. (ed.), 1991, Fundamental Virology, Second Edition, Raven Press, New York, incorporated by reference herein in its entirety).

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, interleukin-1, -2, -4, -5, -6, -12.

In addition, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric NDV that may then be used to elicit a vertebrate immune response. Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); hepatitis A or C virus surface antigens, the glycoproteins of Epstein Barr virus; the glycoproteins of human papillomavirus; the glycoproteins of respiratory syncytial virus, parainfluenza virus, Sendai virus, simianvirus 5 or mumps virus; the glycoproteins of influenza virus; the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Other heterologous sequences may be derived from tumor antigens, and the resulting chimeric viruses be used to generate an immune response against the tumor cells leading to tumor regression in vivo. These vaccines may be used in combination with other therapeutic regimens, including but not limited to chemotherapy, radiation therapy, surgery, bone marrow transplantation, etc. for the treatment of tumors. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nomelanoma antigens for breast, ovarian, cervical and pancreatic carcinoma, HER-2/neu, human papillomavirus-E6, -E7, MUC-1.

In specific embodiments, the NDV used in a combination therapy disclosed herein is genetically engineered to encode and express a heterologous peptide or protein. In certain embodiments, the NDV used in a combination therapy disclosed herein is a chimeric NDV known to one of skill in the art, or a chimeric NDV disclosed herein (see, e.g., Section 5.2, infra). In some embodiments, the NDV used in a combination therapy disclosed herein is a chimeric NDV comprising a genome engineered to express a tumor antigen (see below for examples of tumor antigens). In certain embodiments, the NDV used in a combination therapy disclosed herein is a chimeric NDV comprising a genome engineered to express a heterologous interferon antagonist (see below for examples of heterologous interferon antagonists). In some embodiments, the NDV used in a combination therapy disclosed herein is a chimeric NDV disclosed in U.S. patent application publication No. 2012/0058141, which is incorporated herein by reference in its entirety. In certain embodiments, the NDV used in a combination therapy disclosed herein is a chimeric NDV disclosed in U.S. patent application publication No. 2012/0122185, which is incorporated herein by reference in its entirety. In some embodiments, the NDV used in a combination therapy disclosed herein is a chimeric NDV comprising a genome engineered to express a cytokine, such as, e.g., IL-2, IL-7, IL-9, IL-15, IL-17, IL-21, IL-22, IFN-gamma, GM-CSF, and TNF-alpha. In some embodiments, the NDV used in a combination therapy disclosed herein is a chimeric NDV comprising a genome engineered to express IL-2.

5.2 Chimeric Newcastle Disease Virus

In one aspect, described herein are chimeric NDVs, comprising a genome engineered to express an agonist of a co-stimulatory signal and/or an antagonist of an inhibitory signal of an immune cell, such as, e.g., a T-lymphocyte or Natural Killer (NK) cell. In a specific embodiment, a genome of a NDV is engineered to express an agonist of a co-stimulatory signal of an immune cell, such as, e.g., a T-lymphocyte or NK cell. In another specific embodiment, a genome of a NDV is engineered to express an antagonist of an inhibitory signal of an immune cell, such as, e.g., a T-lymphocyte or NK cell. In other words, the NDV serves as the "backbone" that is engineered to express an agonist of a co-stimulatory signal and/or an antagonist of an inhibitory signal of an immune cell, such as, e.g., a T-lymphocyte or Natural Killer (NK) cell. Specific examples of agonists of co-stimulatory signals as well as specific examples of antagonists of inhibitory signal are provided below.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, and a mutated F protein. In one embodiment, a genome of a NDV is engineered to express an agonist of a co-stimulatory signal of an immune cell, such as, e.g., a T-lymphocyte or NK cell, and a mutated F protein. In another embodiment, a genome of a NDV is engineered to express an antagonist of an inhibitory signal of an immune cell, such as, e.g., a T-lymphocyte or NK cell, and a mutated F protein. In a specific embodiment, the mutated F protein is highly fusogenic and able to form syncytia. In another specific embodiment, the mutated F protein is incorporated into the virion. In certain embodiments, the genome of a NDV engineered to express an agonist of a co-stimulatory signal and/or an antagonist of an inhibitory signal of an immune cell, such as, e.g., a T-lymphocyte or NK cell, comprises an NDV V protein encoding sequence.

In one embodiment, a genome of a NDV is engineered to express an agonist of a co-stimulatory signal and/or an antagonist of an inhibitory signal of an immune cell, such as, e.g., a T-lymphocyte or NK cell, and a mutated F protein with a mutated cleavage site. In a specific embodiment, the NDV is engineered to express a mutated F protein in which the cleavage site of the F protein is mutated to produce a polybasic amino acid sequence, which allows the protein to be cleaved by intracellular proteases, which makes the virus more effective in entering cells and forming syncytia. In another specific embodiment, the NDV is engineered to express a mutated F protein in which the cleavage site of the F protein is replaced with one containing one or two extra arginine residues, allowing the mutant cleavage site to be activated by ubiquitously expressed proteases of the furin family. Specific examples of NDVs that express such a mutated F protein include, but are not limited to, rNDV/F2aa and rNDV/F3aa. For a description of mutations introduced into a NDV F protein to produce a mutated F protein with a mutated cleavage site, see, e.g., Park et al. (2006) Engineered viral vaccine constructs with dual specificity: avian influenza and Newcastle disease. *PNAS USA* 103: 8203-2808, which is incorporated herein by reference in its entirety. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

In some embodiments, the genome of a NDV engineered to express an agonist of a co-stimulatory signal and/or an antagonist of an inhibitory signal of an immune cell, such as, e.g., a T-lymphocyte or NK cell, comprises a mutated NDV V protein encoding sequence, such as disclosed by Elankumaran et al., 2010, J. Virol. 84(8): 3835-3844. In other embodiments, the genome of a NDV engineered to express an agonist of a co-stimulatory signal and/or an antagonist of an inhibitory signal of an immune cell, such as, e.g., a T-lymphocyte or NK cell does not comprise an NDV V protein encoding sequence. In certain embodiments, parental backbone of the chimeric NDV is a mesogenic or velogenic NDV strain that is engineered to express a mutated V protein, such as disclosed by Elankumaran et al., 2010, J. Virol. 84(8): 3835-3844.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, and a cytokine. In a specific embodiment, a genome of a NDV is engineered to express an agonist of a co-stimulatory signal of an immune cell, such as, e.g., a T-lymphocyte or NK cell, and a cytokine. In a specific embodiment, a genome of a NDV is engineered to express an antagonist of an inhibitory signal of an immune cell, such as, e.g., a T-lymphocyte or NK cell, and a cytokine. Specific examples of cytokines include, but are not limited to, interleukin (IL)-2, IL-7, IL-9, IL-15, IL-17, IL-21, IL-22, interferon (IFN) gamma, GM-CSF, and tumor necrosis factor (TNF)-alpha.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, a mutated F protein, and a cytokine (e.g., IL-2, IL-7, IL-9, IL-15, IL-17, IL-21, IL-22, IFN-gamma, GM-CSF, and TNF-alpha). In a specific embodiment, the mutated F protein are highly fusogenic. In a specific embodiment, the mutated F protein has a mutant cleavage site (such as described herein). In some embodiments, the mutated F protein comprises the amino acid mutation L289A. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

In a specific embodiment, described herein are chimeric NDVs, comprising a genome engineered to express (i) an agonist of a co-stimulatory signal and/or an antagonist of an inhibitory signal of an immune cell, and (ii) a tumor antigen. In a specific embodiment, a genome of a NDV is engineered to express an agonist of a co-stimulatory signal of an immune cell, such as, e.g., a T-lymphocyte or NK cell, and a tumor antigen. In a specific embodiment, a genome of a NDV is engineered to express an antagonist of an inhibitory signal of an immune cell, such as, e.g., a T-lymphocyte or NK cell, and a tumor antigen.

Tumor antigens include tumor-associated antigens and tumor-specific antigens. Specific examples of tumor antigens include, but are not limited to, MAGE-1, MAGE-3, BAGE, GAGE-1, GAGE-2, N-acetylglucosaminyltransferase-V, p-15, gp100, MART-1/MelanA, TRP-1 (gp75), Tyrosinase, cyclin-dependent kinase 4, β-catenin, MUM-1, CDK4, HER-2/neu, human papillomavirus-E6, human papillomavirus E7, CD20, carcinoembryonic antigen (CEA), epidermal growth factor receptor, MUC-1, caspase-8, CD5, mucin-1, Lewisx, CA-125, p185HER2, IL-2R, Fap-α, tenascin, antigens associated with a metalloproteinase, and CAMPATH-1. Other examples include, but are not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, CEA, polymorphic epithelial mucin antigen, milk fat globule antigen, colorectal tumor-associated antigens (such as: CEA, TAG-72, CO17-1A, GICA 19-9, CTA-1 and LEA), Burkitt's lymphoma antigen-38.13, CD19, B-lymphoma antigen-CD20, CD33, melanoma specific antigens (such as ganglioside GD2, ganglioside GD3, ganglioside GM2, ganglioside GM3), tumor-specific transplantation type of cell-surface antigen (TSTA) (such as virally-induced tumor antigens including T-antigen DNA tumor viruses and Envelope antigens of RNA tumor viruses), oncofetal antigen-alpha-fetoprotein such as CEA of colon, bladder tumor oncofetal antigen, differentiation antigen (such as human lung carcinoma antigen L6 and L20), antigens of fibrosarcoma, leukemia T cell antigen-Gp37, neoglycoprotein, sphingolipids, breast cancer antigens (such as EGFR (Epidermal growth factor receptor), HER2 antigen (p185.sup.HER2) and HER2 neu epitope), polymorphic epithelial mucin (PEM), malignant human lymphocyte antigen-APO-1, differentiation antigen (such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, My1, VIM-D5, D.sub.156-22 found in colorectal cancer, TRA-1-85 (blood group H), C14 found in colonic adenocarcinoma, F3 found in lung adenocarcinoma, AH6 found in gastric cancer, Y hapten, Le.sup.y found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos), T cell receptor derived peptide from a Cutaneous T cell Lymphoma, C-reactive protein (CRP), cancer antigen-50 (CA-50), cancer antigen 15-3 (CA15-3) associated with breast cancer, cancer antigen-19 (CA-19) and cancer antigen-242 associated with gastrointestinal cancers, carcinoma associated antigen (CAA), chromogranin A, epithelial mucin antigen (MC5), human epithelium specific antigen (E1A), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, a mutated F protein, and a tumor antigen. In a specific embodiment, the mutated F protein are highly fusogenic. In a specific embodiment, the mutated F protein has a mutant cleavage site (such as described herein). In some embodiments, the mutated F protein comprises the amino acid mutation L289A. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

In another specific embodiment, described herein are chimeric NDVs, comprising a genome engineered to express (i) an agonist of a co-stimulatory signal and/or an antagonist of an inhibitory signal of an immune cell, and (ii) a heterologous interferon antagonist. In a specific embodiment, a genome of a NDV is engineered to express an agonist of a co-stimulatory signal of an immune cell, such as, e.g., a T-lymphocyte or NK cell, and a heterologous interferon antagonist. In a specific embodiment, a genome of a NDV is engineered to express an antagonist of an inhibitory signal of an immune cell, such as, e.g., a T-lymphocyte or NK cell, and a heterologous interferon antagonist. See, e.g., U.S. patent application publication No. 2012-0058141, which is incorporated herein by reference, for examples of chimeric NDV engineered to express heterologous interferon antagonists.

Interferon antagonists may be identified using any technique known to one of skill in the art, including, e.g., the techniques described in U.S. Pat. Nos. 6,635,416; 7,060,430; and 7,442,527; which are incorporated herein by reference in their entirety. In a specific embodiment, the heterologous interferon antagonist is a viral protein. Such viral proteins may be obtained or derived from any virus and the virus may infect any species (e.g., the virus may infect humans or non-human mammals). Exemplary heterologous interferon antagonists include, without limitation, Nipah virus W protein, Nipah V protein, Ebola virus VP35 protein, vaccinia virus E3L protein, influenza virus NS1 protein, respiratory syncytial virus (RSV) NS2 protein, herpes simplex virus (HSV) type 1 ICP34.5 protein, Hepatitis C virus NS3-4 protease, dominant-negative cellular proteins that block the induction or response to innate immunity (e.g., STAT1, MyD88, IKK and TBK), and cellular regulators of the innate immune response (e.g., SOCS proteins, PIAS proteins, CPLD proteins, IkB protein, Atg5 protein, Pin1 protein, IRAK-M protein, and UBP43). See, e.g., U.S. patent application publication No. 2012-0058141, which is incorporated herein by reference in its entirety, for additional information regarding heterologous interferon antagonist.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, a mutated F protein, and a heterologous interferon antagonist. In a specific embodiment, the mutated F protein are highly fusogenic. In a specific embodiment, the mutated F protein has a mutant cleavage site (such as described herein). In some embodiments, the mutated F protein comprises the amino acid mutation L289A. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, and a pro-apoptotic molecule. In a specific embodiment, a genome of a NDV is engineered to express an agonist of a co-stimulatory signal of an immune cell, such as, e.g., a T-lymphocyte or NK cell, and a pro-apoptotic molecule. In a specific embodiment, a genome of a NDV is engineered to express an antagonist of an inhibitory signal of an immune cell, such as, e.g., a T-lymphocyte or NK cell, and a pro-apoptotic molecule. Specific examples of pro-apoptotic molecules include, but are not limited to, Bax, Bak, Bad, BID, Bcl-xS, Bim, Noxa, Puma, AIF, FasL, and TRAIL.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, a mutated F protein, and a pro-apoptotic molecule. In a specific embodiment, the mutated F protein are highly fusogenic. In a specific embodiment, the mutated F protein has a mutant cleavage site (such as described herein). In some embodiments, the mutated F protein comprises the amino acid mutation L289A. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, and an anti-apoptotic molecule. In a specific embodiment, a genome of a NDV is engineered to express an agonist of a co-stimulatory signal of an immune cell, such as, e.g., a T-lymphocyte or NK cell, and an anti-apoptotic molecule. In a specific embodiment, a genome of a NDV is engineered to express an antagonist of an inhibitory signal of an immune cell, such as, e.g., a T-lymphocyte or NK cell, and an anti-apoptotic molecule. Specific examples of anti-apoptotic molecules include, but are not limited to, Bcl-2, Bcl-xL, Mcl-1, and XIAP.

In another aspect, described herein are chimeric NDVs, comprising a genome engineered to express an agonist of a co-stimulatory signal and/or an antagonist of an inhibitory signal of an immune cell, such as, e.g., a T-lymphocyte or NK cell, a mutated F protein, and an anti-apoptotic molecule. In a specific embodiment, the mutated F protein are highly fusogenic. In a specific embodiment, the mutated F protein has a mutant cleavage site (such as described herein). In some embodiments, the mutated F protein comprises the amino acid mutation L289A. In some embodiments, the chimeric NDV is engineered to express a mutated F protein with the amino acid mutation L289A. In certain embodiments, the mutated F protein is from a different type or strain of NDV than the backbone NDV. In specific embodiments the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion.

Any NDV type or strain may be used as a backbone that is engineered to express an agonist of a co-stimulatory signal and/or an antagonist of an inhibitory signal of an immune cell, such as, e.g., a T-lymphocyte or NK cell, and in certain embodiments, engineered to express a cytokine, tumor antigen, heterologous interferon antagonist and/or mutated F protein, including, but not limited to, naturally-occurring strains, variants or mutants, mutagenized viruses, reassortants and/or genetically engineered viruses. In a specific embodiment, the NDV used in a combination therapy disclosed herein is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is mesogenic strain. In other embodiments, the NDV that serves as the backbone for genetic engineering is a velogenic strain. Specific examples of NDV strains include, but are not limited to, the 73-T strain, NDV HUJ strain, Ulster strain, MTH-68 strain, Italien strain, Hickman strain, PV701 strain, Hitchner B1 strain, La Sota strain (see, e.g., Genbank No. AY845400), YG97 strain, MET95 strain, Roakin strain, and F48E9 strain. In a specific embodiment, the NDV that serves as the backbone for genetic engineering is the Hitchner B1 strain. In another specific embodiment, the NDV that serves as the backbone for genetic engineering is a B1 strain as identified by Genbank No. AF309418 or NC_002617. In another specific embodiment, the NDV that serves as the backbone for genetic engineering is the NDV identified by ATCC No. VR2239. In another specific embodiment, the NDV that serves as the backbone for genetic engineering is the La Sota strain.

In certain embodiments, attenuation, or further attenuation, of the chimeric NDV is desired such that the chimeric NDV remains, at least partially, infectious and can replicate in vivo, but only generate low titers resulting in subclinical levels of infection that are non-pathogenic (see, e.g., Khattar et al., 2009, J. Virol. 83:7779-7782). In a specific embodiment, the NDV is attenuated by deletion of the V protein. Such attenuated chimeric NDVs may be especially suited for embodiments wherein the virus is administered to a subject in order to act as an immunogen, e.g., a live vaccine. The viruses may be attenuated by any method known in the art.

In specific embodiments, in addition to expressing an agonist of a co-stimulatory signal and/or an antagonist of an inhibitory signal of an immune cell, such as, e.g., a T-lymphocyte or NK cell, and in certain embodiments, a mutated F protein and a cytokine, a chimeric NDV is engineered to express a suicide gene (e.g., thymidine kinase) or another molecule that inhibits NDV replication or function (a gene that makes NDV sensitive to an antibiotic or an anti-viral agent). In some embodiments, in addition to expressing an agonist of a co-stimulatory signal and/or an antagonist of an inhibitory signal of an immune cell, such as, e.g., a T-lymphocyte or NK cell, and in certain embodiments, a mutated F protein and a cytokine, a chimeric NDV is engineered to encode tissue-specific microRNA (miRNA) target sites (e.g., sites targeted by miR-21, miR-184, miR-133a/133b, miR-137, and/or miR-193a microRNAs).

In certain embodiments, the tropism of the chimeric NDV is altered. In a specific embodiment, the tropism of the virus is altered by modification of the F protein cleavage site to be recognized by tissue-specific or tumor-specific proteases such as matrix metalloproteases (MMP) and urokinase. In other embodiments, tropism of the virus is altered by introduction of tissue-specific miRNA target sites. In certain embodiments NDV HN protein is mutated to recognize tumor-specific receptor.

In embodiments herein, the agonist of a co-stimulatory signal and/or the antagonist of an inhibitory signal of an immune cell may be inserted into the genome of the backbone NDV between two transcription units. In a specific embodiment, the agonist of a co-stimulatory signal and/or the antagonist of an inhibitory signal of an immune cell is inserted into the genome of the backbone NDV between the M and P transcription units or between the HN and L transcription units. In accordance with other embodiments herein, the cytokine, and/or mutated F protein are inserted into the genome of the backbone NDV between two or more transcription units (e.g., between the M and P transcription units or between the HN and L transcription units).

5.2.1. Immune Cell Stimulatory Agents

The chimeric NDVs described herein may be engineered to express any agonist of a co-stimulatory signal and/or any antagonist of an inhibitory signal of an immune cell, such as, e.g., a T-lymphocyte, NK cell or antigen-presenting cell (e.g., a dendritic cell or macrophage), known to one of skill in the art. In specific embodiments, the agonist and/or antagonist is an agonist of a human co-stimulatory signal of an immune cell and/or antagoinst of a human inhibitory signal of an immune cell. In certain embodiments, the agonist of a co-stimulatory signal is an agonist of a co-stimulatory molecule (e.g., co-stimulatory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of co-stimulatory molecules include glucocorticoid-induced tumor necrosis factor receptor (GITR), Inducible T-cell costimulator (ICOS or CD278), OX40 (CD134), CD27, CD28, 4-1BB (CD137), CD40, lymphotoxin alpha (LT alpha), and LIGHT (lymphotoxin-like, exhibits inducible expression, and competes with herpes simplex virus glycoprotein D for HVEM, a receptor expressed by T lymphocytes). In specific embodiments, the agonist is an agonist of a human co-stimulatory receptor of an immune cell. In certain embodiments, the agonist of a co-stimulatory receptor is not an agonist of ICOS. In some embodiments, the antagonist is an antagonist of an inhibitory molecule (e.g., inhibitory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of inhibitory molecules include cytotoxic T-lymphocyte-associated antigen 4 (CTLA-4 or CD52), programmed cell death protein 1 (PD1 or CD279), B and T-lymphocyte attenuator (BTLA), killer cell immunoglobulin-like receptor (KIR), lymphocyte activation gene 3 (LAG3), T-cell membrane protein 3 (TIM3), CD160, and adenosine A2a receptor (A2aR). In specific embodiments, the antagonist is an antagonist of a human inhibitory receptor of an immune cell.

In a specific embodiment, the agonist of a co-stimulatory receptor is an antibody or antigen-binding fragment thereof that specifically binds to the co-stimulatory receptor. Specific examples of co-stimulatory receptors include GITR, ICOS, OX40, CD27, CD28, 4-1BB, or CD40. In certain specific embodiments, the antibody is a monoclonal antibody. In other specific embodiments, the antibody is an sc-Fv. In a specific embodiment the antibody is a bispecific antibody that binds to two receptors on an immune cell. In other embodiments, the bispecific antibody binds to a receptor on an immune cell and to another receptor on a cancer cell. In specific embodiments, the antibody is a human or humanized antibody. In other embodiments the ligand or an antibody is a chimeric protein with NDV F protein or NDV HN protein. See, e.g., U.S. patent application Publication No. 2012/0122185, which is incorporated herein by reference for a description regarding generation of chimeric F or chimeric HN proteins. In a specific embodiment, the chimeric protein is the chimeric F protein described in Section 6, infra. The techniques described below for generating the chimeric ICOSL-F protein can be used to generate other chimeric F proteins or chimeric HN proteins.

In another embodiment, the agonist of a co-stimulatory receptor is a ligand of the co-stimulatory receptor. In certain embodiments, the ligand is fragment of a native ligand. Specific examples of native ligands include B7RP1, CD137L, OX40L, CD70, herpes virus entry mediator (HVEM), CD80, and CD86. The nucleotide sequences encoding native ligands as well as the amino acid sequences of native ligands are known in the art. For example, the nucleotide and amino acid sequences of B7RP1 (GenBank human: NM_015259.4, NP_056074.1 murine: NM_015790.3, NP_056605.1), CD137L(GenBank human: NM_003811.3, NP_003802.1, murine: NM_009404.3, NP_033430.1), OX40L(GenBank human: NM_003326.3, NP_003317.1, murine: NM_009452.2, NP_033478.1), CD70(GenBank human: NM_001252.3, NP_001243.1, murine: NM_011617.2, AAD00274.1), CD80(GenBank human: NM_005191.3, NP_005182.1, murine: NM_009855.2, NP_033985.3) and CD86(GenBank human: NM_005191.3, CAG46642.1, murine: NM_019388.3, NP_062261.3) can be found in GenBank. In other embodiments, the ligand is a derivative of a native ligand. In some embodiments, the ligand is a fusion protein comprising at least a portion of the native ligand or a derivative of the native ligand that specifically binds to the co-stimulatory receptor, and a heterologous amino acid sequence. In specific embodiments, the fusion protein comprises at least a portion of the native ligand or a derivative of the native ligand that specifically binds to the co-stimulatory receptor, and the Fc portion of an immunoglobulin or a fragment thereof. An example of a ligand fusion protein is a 4-1BB ligand fused to Fc portion of immunoglobulin (described by Meseck M et al., J Immunother. 2011 34:175-82).

In another embodiment, the antagonist of an inhibitory receptor is an antibody (or an antigen-binding fragment) or a soluble receptor that specifically binds to the native ligand for the inhibitory receptor and blocks the native ligand from binding to the inhibitory receptor and transducing an inhibitory signal(s). Specific examples of native ligands for inhibitory receptors include PDL-1, PDL-2, B7-H3, B7-H4, HVEM, Gal9 and adenosine. Specific examples of inhibitory receptors that bind to a native ligand include CTLA-4, PD-1, BTLA, KIR, LAG3, TIM3, and A2aR.

In specific embodiments, the antagonist of an inhibitory receptor is a soluble receptor that specifically binds to the native ligand for the inhibitory receptor and blocks the native ligand from binding to the inhibitory receptor and transducing an inhibitory signal(s). In certain embodiments, the soluble receptor is a fragment of a native inhibitory receptor or a fragment of a derivative of a native inhibitory receptor that specifically binds to native ligand (e.g., the extracellular domain of a native inhibitory receptor or a derivative of an inhibitory receptor). In some embodiments, the soluble receptor is a fusion protein comprising at least a portion of the native inhibitory receptor or a derivative of the native inhibitory receptor (e.g., the extracellular domain of the native inhibitory receptor or a derivative of the native inhibitory receptor), and a heterologous amino acid sequence. In specific embodiments, the fusion protein comprises at least a portion of the native inhibitory receptor or a derivative of the native inhibitory receptor, and the Fc portion of an immunoglobulin or a fragment thereof. An example of a soluble receptor fusion protein is a LAG3-Ig fusion protein (described by Huard B et al., Eur J Immunol. 1995 25:2718-21).

In specific embodiments, the antagonist of an inhibitory receptor is an antibody (or an antigen-binding fragment) that specifically binds to the native ligand for the inhibitory receptor and blocks the native ligand from binding to the inhibitory receptor and transducing an inhibitory signal(s). In certain specific embodiments, the antibody is a monoclonal antibody. In other specific embodiments, the antibody is an scFv. In particular embodiments, the antibody is a human or humanized antibody. A specific example of an antibody to inhibitory ligand is anti-PD-L1 antibody (Iwai Y, et al. PNAS 2002; 99:12293-12297).

In another embodiment, the antagonist of an inhibitory receptor is an antibody (or an antigen-binding fragment) or ligand that binds to the inhibitory receptor, but does not transduce an inhibitory signal(s). Specific examples of inhibitory receptors include CTLA-4, PD1, BTLA, KIR, LAG3, TIM3, and A2aR. In certain specific embodiments, the antibody is a monoclonal antibody. In other specific embodiments, the antibody is an scFv. In particular embodiments, the antibody is a human or humanized antibody. A specific example of an antibody to inhibitory receptor is anti-CTLA-4 antibody (Leach D R, et al. Science 1996; 271: 1734-1736). Another example of an antibody to inhibitory receptor is anti-PD-1 antibody (Topalian S L, NEJM 2012; 28:3167-75).

In certain embodiments, a chimeric NDV described herein is engineered to express an antagonist of CTLA-4, such as, e.g., Ipilimumab or Tremelimumab. In certain embodiments, a chimeric NDV described herein is engineered to express an antagonist of PD1, such as, e.g., MDX-1106 (BMS-936558), MK3475, CT-011, AMP-224, or MDX-1105. In certain embodiments, a chimeric NDV described herein is engineered to express an antagonist of LAG3, such as, e.g., IMP321. In certain embodiments, a chimeric NDV described herein is engineered to express an antibody (e.g., a monoclonal antibody or an antigen-binding fragment thereof, or scFv) that binds to B7-H3, such as, e.g., MGA271. In specific embodiments, a chimeric NDV described herein is engineered to express an agonist of a co-stimulatory signal of an immune cell and/or an antagonist of an inhibitory signal of an immune cell described in Section 6, infra. In specific embodiments, NDV described herein is engineered to express anti-CD28 scvFv, ICOSL, CD40L, OX40L, CD137L, GITRL, and/or CD70.

In certain embodiments, an agonist of a co-stimulatory signal of an immune cell induces (e.g., selectively) induces one or more of the signal transduction pathways induced by the binding of a co-stimulatory receptor to its ligand. In specific embodiments, an agonist of a co-stimulatory receptor induces one or more of the signal transduction pathways induced by the binding of the co-stimulatory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to one or more of its ligands in the absence of the agonist. In specific embodiments, an agonist of a co-stimulatory receptor: (i) induces one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not induce, or induces one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In certain embodiments, an agonist of a co-stimulatory signal of an immune cell activates or enhances (e.g., selectively activates or enhances) one or more of the signal transduction pathways induced by the binding of a co-stimulatory receptor to its ligand. In specific embodiments, an agonist of a co-stimulatory receptor activates or enhances one or more of the signal transduction pathways induced by the binding of the co-stimulatory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of co-stimulatory receptor to one or more of its ligands in the absence of the agonist. In specific embodiments, an agonist of a co-stimulatory receptor: (i) an agonist of a co-stimulatory signal activates or enhances one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not activate or enhance, or activates or enhances one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In some embodiments, an antagonist of an inhibitory signal of an immune cell (e.g., selectively) inhibits or reduces one or more of the signal transduction pathways induced by the binding of an inhibitory receptor to its ligand. In specific embodiments, an antagonist of an inhibitory receptor inhibits or reduces one or more of the signal transduction pathways induced by the binding of the inhibitory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to one or more of its ligands in the absence of the antagonist. In specific embodiments, an antagonist of an inhibitory receptor: (i) inhibits or reduces one or more of the signal transduction pathways induced by the binding of the inhibitory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to the one particular ligand in the absence of the antagonist; and (ii) does not inhibit or reduce, or inhibits or reduces one or more of the signal transduction pathways induced by the binding of the inhibitory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of inhibitory receptor to such one or more other ligands in the absence of the antagonist.

In specific embodiments, an agonist of a co-stimulatory signal of an immune cell and/or an antagonist of an inhibitory signal of an immune cell induces, activates and/or enhances one or more immune activities, functions or responses. The one or more immune activities, functions or responses can be in the form of, e.g., an antibody response (humoral response) or a cellular immune response, e.g., cytokine secretion (e.g., interferon-gamma), helper activity or cellular cytotoxicity. In one embodiment, expression of an activation marker on immune cells (e.g., CD44, Granzyme, or Ki-67), expression of a co-stimulatory receptor on immune cells (e.g., ICOS, CD28, OX40, or CD27), expression of a ligand for a co-stimulatory receptor (e.g., B7HRP1, CD80, CD86, OX40L, or CD70), cytokine secretion, infiltration of immune cells (e.g., T-lymphocytes, B lymphocytes and/or NK cells) to a tumor, antibody production, effector function, T cell activation, T cell differentiation, T cell proliferation, B cell differentiation, B cell proliferation, and/or NK cell proliferation is induced, activated and/or enhanced following contact with an agonist of a co-stimulatory signal of an immune cell and/or an antagonist of an inhibitory signal of an immune cell. In another embodiment, myeloid-derived suppressor cell (MDSC) tumor infiltration and proliferation, Treg tumor infiltration, activation and proliferation, peripheral blood MDSC and Treg counts are inhibited following contact with an agonist of a co-stimulatory signal of an immune cell and/or an antagonist of an inhibitory signal of an immune cell.

5.3 Construction of NDVs

The NDVs described herein can be generated using the reverse genetics technique. The reverse genetics technique involves the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 6,146,642 issued Nov. 14, 2000; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a NDV described herein. Briefly, a complete cDNA of a NDV (e.g., the Hitchner B1 strain) is constructed, inserted into a plasmid vector and engineered to contain a unique restriction site between two transcription units (e.g., the NDV P and M genes; or the NDV HN and L genes). A nucleotide sequence encoding a heterologous amino acid sequence (e.g., a nucleotide sequence encoding an agonist of a co-stimulatory signal and/or an antagonist of an inhibitory signal of an immune cell) may be inserted into the viral genome at the unique restriction site. Alternatively, a nucleotide sequence encoding a heterologous amino acid sequence (e.g., a nucleotide sequence encoding an agonist of a co-stimulatory signal and/or an antagonist of an inhibitory signal of an immune cell) may be engineered into a NDV transcription unit so long as the insertion does not affect the ability of the virus to infect and replicate. The single segment is positioned between a T7 promoter and the hepatitis delta virus ribozyme to produce an exact negative transcript from the T7 polymerase. The plasmid vector and expression vectors comprising the necessary viral proteins are transfected into cells leading to production of recombinant viral particles (see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety).

Techniques for the production of a chimeric NDV that express an antibody are known in the art. See, e.g., Puhler et al., Gene Ther. 15(5): 371-283 (2008) for the generation of a recombinant NDV expressing a full IgG from two transgenes.

Bicistronic techniques to produce multiple proteins from a single mRNA are known to one of skill in the art. Bicistronic techniques allow the engineering of coding sequences of multiple proteins into a single mRNA through the use of IRES sequences. IRES sequences direct the internal recruitment of ribozomes to the RNA molecule and allow downstream translation in a cap independent manner. Briefly, a coding region of one protein is inserted into the ORF of a second protein. The insertion is flanked by an IRES and any untranslated signal sequences necessary for proper expression and/or function. The insertion must not disrupt the open reading frame, polyadenylation or transcriptional promoters of the second protein (see e.g., Garcia-Sastre et al., 1994, J. Virol. 68:6254-6261 and Garcia-Sastre et al., 1994 Dev. Biol. Stand. 82:237-246, each of which are incorporated by reference herein in their entirety).

5.4 Propagation of NDVs

The NDVs described herein (e.g., the chimeric NDVs) can be propagated in any substrate that allows the virus to grow to titers that permit the uses of the viruses described herein. In one embodiment, the substrate allows the NDVs described herein (e.g., the chimeric NDVs) to grow to titers comparable to those determined for the corresponding wild-type viruses.

The NDVs described herein (e.g., the chimeric NDVs) may be grown in cells (e.g., avian cells, chicken cells, etc.) that are susceptible to infection by the viruses, embryonated eggs (e.g., chicken eggs or quail eggs) or animals (e.g., birds). Such methods are well-known to those skilled in the art. In a specific embodiment, the NDVs described herein (e.g., the chimeric NDVs) may be propagated in cancer cells, e.g., carcinoma cells (e.g., breast cancer cells and prostate cancer cells), sarcoma cells, leukemia cells, lymphoma cells, and germ cell tumor cells (e.g., testicular cancer cells and ovarian cancer cells). In another specific embodiment, the NDVs described herein (e.g., the chimeric NDVs) may be propagated in cell lines, e.g., cancer cell lines such as HeLa cells, MCF7 cells, THP-1 cells, U87 cells, DU145 cells, Lncap cells, and T47D cells. In another embodiment, the NDVs described herein (e.g., the chimeric NDVs) are propagated in chicken cells or embryonated eggs. Representative chicken cells include, but are not limited to, chicken embryo fibroblasts and chicken embryo kidney cells. In a specific embodiment, the NDVs described herein (e.g., the chimeric NDVs) are propagated in Vero cells. In another specific embodiment, the NDVs described herein (e.g., the chimeric NDVs) are propagated in cancer cells in accordance with the methods described in Section 6, infra. In another specific embodiment, the NDVs described herein (e.g., the chimeric NDVs) are propagated in chicken eggs or quail eggs. In certain embodiments, a NDV virus described herein (e.g., a chimeric NDV) is first propagated in embryonated eggs and then propagated in cells (e.g., a cell line).

The NDVs described herein (e.g., the chimeric NDVs) may be propagated in embryonated eggs, e.g., from 6 to 14 days old, 6 to 12 days old, 6 to 10 days old, 6 to 9 days old, 6 to 8 days old, or 10 to 12 days old. Young or immature embryonated eggs can be used to propagate the NDVs described herein (e.g., the chimeric NDVs). Immature embryonated eggs encompass eggs which are less than ten day old eggs, e.g., eggs 6 to 9 days old or 6 to 8 days old that are IFN-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The NDVs described herein (e.g., the chimeric NDVs) can be propagated in different locations of the embryonated egg, e.g., the allantoic cavity. For a detailed discussion on the growth and propagation viruses, see, e.g., U.S. Pat. No. 6,852,522 and U.S. Pat. No. 7,494,808, both of which are hereby incorporated by reference in their entireties.

For virus isolation, the NDVs described herein (e.g., the chimeric NDVs) can be removed from cell culture and separated from cellular components, typically by well known clarification procedures, e.g., such as gradient centrifugation and column chromatography, and may be further purified as desired using procedures well known to those skilled in the art, e.g., plaque assays.

5.5 Compositions & Routes of Administration

Encompassed herein is the use of a NDV described herein (e.g., the chimeric NDVs) in compositions. Also encompassed herein is the use of plasma membrane fragments from NDV infected cells or whole cancer cells infected with NDV in compositions. In a specific embodiment, the compositions are pharmaceutical compositions, such as immunogenic formulations (e.g., vaccine formulations). The compositions may be used in methods of treating cancer.

In one embodiment, a pharmaceutical composition comprises a NDV described herein (e.g., the chimeric NDVs), in an admixture with a pharmaceutically acceptable carrier. In some embodiments, the pharmaceutical composition further comprises one or more additional prophylactic or therapeutic agents, such as described in Section 5.6.4, infra. In a specific embodiment, a pharmaceutical composition comprises an effective amount of a NDV described herein (e.g., the chimeric NDVs), and optionally one or more additional prophylactic of therapeutic agents, in a pharmaceutically acceptable carrier. In some embodiments, the NDV (e.g., a chimeric NDV) is the only active ingredient included in the pharmaceutical composition.

In another embodiment, a pharmaceutical composition (e.g., an oncolysate vaccine) comprises a protein concentrate or a preparation of plasma membrane fragments from NDV infected cancer cells, in an admixture with a pharmaceutically acceptable carrier. In some embodiments, the pharmaceutical composition further comprises one or more additional prophylactic or therapeutic agents, such as described in Section 5.6.4, infra. In another embodiment, a pharmaceutical composition (e.g., a whole cell vaccine) comprises cancer cells infected with NDV, in an admixture with a pharmaceutically acceptable carrier. In some embodiments, the pharmaceutical composition further comprises one or more additional prophylactic or therapeutic agents, such as described in Section 5.6.4, infra.

The pharmaceutical compositions provided herein can be in any form that allows for the composition to be administered to a subject. In a specific embodiment, the pharmaceutical compositions are suitable for veterinary and/or human administration. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, the pharmaceutical compositions are formulated to be suitable for the intended route of administration to a subject. For example, the pharmaceutical composition may be formulated to be suitable for parenteral, intrapleural, inhalation, intraperitoneal, oral, intradermal, colorectal, intraperitoneal and intratumoral administration. In a specific embodiment, the pharmaceutical composition may be formulated for intravenous, oral, intraperitoneal, intranasal, intratracheal, subcutaneous, intramuscular, topical, pulmonary, or intratumoral administration.

5.6 Anti-Cancer Uses and Other Uses

In one aspect, a chimeric NDV described herein (e.g., a chimeric NDV described in Section 5.2, supra) may be used in the treatment of cancer. In one embodiment, provided herein are methods for treating cancer, comprising administering to a subject in need thereof a chimeric NDV described herein (e.g., a chimeric NDV described in Section 5.2, supra) or a composition thereof. In a specific embodiment, provided herein is a method for treating cancer, comprising administering to a subject in need thereof an effective amount of a chimeric NDV described herein (e.g., a chimeric NDV described in Section 5.2, supra) or a composition thereof.

In specific embodiments, a chimeric NDV engineered to express an agonist of a co-stimulatory signal of an immune cell, or a composition thereof is administered to a subject to treat cancer. In another specific embodiments, a chimeric NDV engineered to express an antagonist of an inhibitory signal of an immune cell, or a composition thereof is administered to a subject to treat cancer. In certain embodiments, a chimeric NDV engineered to express an agonist of a co-stimulatory signal of an immune cell and a mutated F protein or a composition thereof is administered to a subject to treat cancer. In certain embodiments, a chimeric NDV engineered to express an antagonist of an inhibitory signal of an immune cell and a mutated F protein or a composition thereof is administered to a subject to treat cancer.

A chimeric NDV (e.g., a chimeric NDV described in Section 5.2, supra) described herein or a composition thereof, an oncolysate vaccine, or a whole cell cancer vaccine used in a method for treating cancer may be used as any line of therapy (e.g., a first, second, third, fourth or fifth line therapy).

In certain embodiments, a chimeric NDV described herein (e.g., a chimeric NDV described in Section 5.2, supra) is the only active ingredient administered to treat cancer. In specific embodiments, a chimeric NDV described herein (e.g., a chimeric NDV described in Section 5.2, supra) is the only active ingredient in a composition administered to treat cancer.

The chimeric NDV (e.g., a chimeric NDV described in Section 5.2, supra) or a composition thereof may be administered locally or systemically to a subject. For example, the chimeric NDV (e.g., a chimeric NDV described in Section 5.2, supra) or composition may be administered parenterally (e.g., intravenously or subcutanously), intratumorally, intrapleurally, intranasally, intraperitoneally, orally, by inhalation, topically or intradermally to a subject.

In certain embodiments, the methods described herein include the treatment of cancer for which no treatment is available. In some embodiments, a chimeric NDV described herein (e.g., a chimeric NDV described in Section 5.2, supra) or a composition thereof is administered to a subject to treat cancer as an alternative to other conventional therapies.

In one embodiment, provided herein is a method for treating cancer, comprising administering to a subject in need thereof a chimeric NDV described herein (e.g., a chimeric NDV described in Section 5.2, supra) or a composition thereof and one or more additional therapies, such as described in Section 5.6.4, infra. In a particular embodiment, one or more therapies are administered to a subject in combination with a chimeric NDV described herein (e.g., a chimeric NDV described in Section 5.2, supra) or a composition thereof to treat cancer. In a specific embodiment, the additional therapies are currently being used, have been used or are known to be useful in treating cancer. In another embodiment, a chimeric NDV described herein (e.g., a chimeric NDV described in Section 5.2, supra) or a composition thereof is administered to a subject in combination with a supportive therapy, a pain relief therapy, or other therapy that does not have a therapeutic effect on cancer. In a specific embodiment, the one or more additional therapies administered in combination with a chimeric NDV described herein (e.g., a chimeric NDV described in Section 5.2, supra) is one or more of the therapies described in Section 5.6.4.1, infra. In certain embodiments, a chimeric NDV described herein (e.g., a chimeric NDV described in Section 5.2, supra) and one or more additional therapies are administered in the same composition. In other embodiments, a chimeric NDV and one or more additional therapies are administered in different compositions.

In certain embodiments, two, three or multiple NDVs (including one, two or more chimeric NDVs described herein, such as one, two or more of the chimeric NDVs described in Section 5.2, supra) are administered to a subject to treat cancer. The second or more chimeric NDVs used in accordance with methods described herein that comprise administration of two, three or multiple NDVs to a subject to treat cancer may be naturally occurring chimeric NDVs or engineered chimeric NDVs that have been engineered to express heterologous amino acid sequence (e.g., a cytokine). The first and second chimeric NDVs may be part of the same pharmaceutical composition or different pharmaceutical compositions. In certain embodiments, the first chimeric NDV and the second chimeric NDV are administered by the same route of administration (e.g., both are administered intratumorally or intravenously). In other embodiments, the first chimeric NDV and the second chimeric NDV are administered by different routes of administration (e.g., one is administered intratumorally and the other is administered intravenously).

In specific embodiments, a first chimeric NDV engineered to express an agonist of a co-stimulatory signal of an immune cell is administered to a patient to treat cancer in combination with a second chimeric NDV engineered to express an antagonist of an inhibitory signal of an immune cell. In other specific embodiments, a first chimeric NDV engineered to express an agonist of a co-stimulatory signal of an immune cell and/or an antagonist of an inhibitory signal of an immune is administered in combination with a second chimeric NDV engineered to express one, two or more of the following: a cytokine (e.g., IL-2), a heterologous interferon antagonist, a tumor antigen, a pro-apopototic molecule, and/or anti-apoptotic molecule. In a specific embodiment, the first chimeric NDV, the second chimeric NDV, or both express a mutated F protein that increases the fusogenic activity of the chimeric NDV. In another specific embodiment, the first chimeric NDV, the second chimeric NDV or both express a mutated F protein with a mutation in the cleavage site (such as described herein).

In specific embodiments, a first composition (e.g., a pharmaceutical composition) comprising a first chimeric NDV engineered to express an agonist of a co-stimulatory signal of an immune cell is administered to a patient to treat cancer in combination with a second composition (e.g., a pharmaceutical composition) comprising a second chimeric NDV engineered to express an antagonist of an inhibitory signal of an immune cell. In other specific embodiments, a first composition (e.g., a pharmaceutical composition) comprising a first chimeric NDV engineered to express an agonist of a co-stimulatory signal of an immune cell and/or an antagonist of an inhibitory signal of an immune is administered in combination with a second composition (e.g., a pharmaceutical composition) comprising a second chimeric NDV engineered to express one, two or more of the following: a cytokine (e.g., IL-2), a heterologous interferon antagonist, a tumor antigen, a pro-apopototic molecule, and/or anti-apoptotic molecule. In a specific embodiment, the first chimeric NDV, the second chimeric NDV, or both express a mutated F protein that increases the fusogenic activity of the chimeric NDV. In another specific embodiment, the first chimeric NDV, the second chimeric NDV or both express a mutated F protein with a mutation in the cleavage site (such as described herein).

In another aspect, an NDV described herein (e.g., an NDV described in Section 5.1, supra) may be used in combination with one or more additional therapies, such as described herein in Section 5.6.4, infra (e.g., Section 5.6.4.1, infra), in the treatment of cancer. In one embodiment, provided herein are methods for treating cancer, comprising administering to a subject in need thereof an NDV described herein (e.g., an NDV described in Section 5.1, supra) or a composition thereof and one or more additional therapies, such as described herein in Section 5.6.4, infra. (e.g., Section 5.6.4.1). In a specific embodiment, provided herein is a method for treating cancer, comprising administering to a subject in need thereof an effective amount of an NDV described herein (e.g., an NDV described in Section 5.1, supra) or a composition thereof and an effective amount of one or more additional therapies, such as described in Section 5.6.4, infra. (e.g., Section 5.6.4.1). In certain embodiments, an NDV described herein (e.g., an NDV described in Section 5.1, supra) and one or more additional therapies, such as described in Section 5.6.4, infra (e.g., Section 5.6.4.1), are administered in the same composition. In other embodiments, an NDV (e.g., an NDV described in Section 5.1, supra) and one or more additional therapies are administered in different compositions.

An NDV (e.g., an NDV described in Section 5.1, supra) described herein or a composition thereof, an oncolysate vaccine, or a whole cell cancer vaccine in combination with one or more additional therapies, such as described herein in Section 5.6.4, infra, may be used as any line of therapy (e.g., a first, second, third, fourth or fifth line therapy) for treating cancer in accordance with a method described herein.

In another aspect, whole cancer cells infected with a chimeric NDV described herein (e.g., a chimeric NDV described in Section 5.2, supra) can be used to treat cancer. In a specific embodiment, a chimeric NDV described herein (e.g., a chimeric NDV described in Section 5.2, supra) may be contacted with a cancer cell or a population of cancer cells and the infected cancer cell or population of cancer cells may be administered to a subject to treat cancer. In one embodiment, the cancer cells are subjected to gamma radiation prior to infection with a chimeric NDV described herein (e.g., a chimeric NDV described in Section 5.2, supra). In another embodiment, the cancer cells are subjected to gamma radiation after infection with a chimeric NDV described herein (e.g., a chimeric NDV described in Section 5.2, supra). In a particular embodiment, the cancer cells are treated prior to administration to a subject so that the cancer cells cannot multiply in the subject. In a specific embodiment, the cancer cells cannot multiply in the subject and the virus cannot infect the subject. In one embodiment, the cancer cells are subjected to gamma radiation prior to administration to subject. In another embodiment, the cancer cells are sonicated prior to administration to a subject. In another embodiment, the cancer cells are treated with mitomycin C prior to administration to a subject. In another embodiment, the cancer cells are treated by freezing and thawing prior to administration to a subject. In another embodiment, the cancer cells are treated with heat treatment prior to administration to a subject. The cancer cells may be administered locally or systemically to a subject. For example, the cancer cells may be administered parenterally (e.g., intravenously or subcutaneously), intratumorally, intransally, orally, by inhalation, intrapleurally, topically or intradermally to a subject. In a specific embodiment, the cancer cells are administered intratumorally or to the skin (e.g., intradermally) of a subject. The cancer cells used may be autologous or allogeneic. In a specific embodiment, the backbone of the chimeric NDV is a non-lytic strain. The cancer cells may be administered to a subject alone or in combination with an additional therapy. The cancer cells are preferably in a pharmaceutical composition. In certain embodiments, the cancer cells are administered in combination with one or more additional therapies, such as described in Section 5.6.4, infra. In certain embodiments, the cancer cells and one or more additional therapies are administered in the same composition. In other embodiments, the cancer cells and one or more additional therapies are administered in different compositions.

In another aspect, whole cancer cells infected with an NDV described herein (e.g., an NDV described in Section 5.1, supra) may be used in combination with one or more additional therapies described herein in Section 5.6.4, infra, in the treatment of cancer. In one embodiment, provided herein are methods for treating cancer, comprising administering to a subject in need thereof whole cancer cells infected with an NDV described herein (e.g., an NDV described in Section 5.1, supra) in combination with one or more additional therapies described herein in Section 5.6.4, infra. In a specific embodiment, provided herein is a method for treating cancer, comprising administering to a subject in need thereof an effective amount of whole cancer cells infected with an NDV described herein (e.g., an NDV described in Section 5.1, supra) in combination with an effective amount of one or more additional therapies described in Section 5.6.4, infra. In certain embodiments, whole cancer cells infected with an NDV described herein (e.g., an NDV described in Section 5.1, supra) and one or more additional therapies described in Section 5.6.4, infra, are administered in the same composition. In other embodiments, whole cancer cells infected with an NDV described herein (e.g., an NDV described in Section 5.1, supra) and one or more additional therapies are administered in different compositions.

In another aspect, a protein concentrate or plasma membrane preparation from lysed cancer cells infected with a chimeric NDV (e.g., a chimeric NDV described in Section 5.2, supra) can be used to treat cancer. In one embodiment, a plasma membrane preparation comprising fragments from cancer cells infected with a chimeric NDV described herein can be used to treat cancer. In another embodiment, a protein concentrate from cancer cells infected with a chimeric NDV described herein can be used to treat cancer. Techniques known to one of skill in the art may be used to produce the protein concentrate or plasma membrane preparation. In a specific embodiment, a chimeric NDV described herein (e.g., a chimeric NDV described in Section 5.2, supra) may be contacted with a cancer cell or a population of cancer cells and the infected cancer cell or population of cancer cells may be lysed using techniques known to one of skill in the art to obtain protein concentrate or plasma membrane fragments of the NDV-infected cancer cells, and the protein concentrate or plasma membrane fragments of the NDV-infected cancer cells may be administered to a subject to treat cancer. The protein concentrate or plasma membrane fragments may be administered locally or systemically to a subject. For example, the protein concentrate or plasma membrane fragments may be administered parenterally, intratumorally, intranasally, intrapleurally, orally, by inhalation, topically or intradermally to a subject. In a specific embodiment, such a protein concentrate or plasma membrane preparation is administered intratumorally or to the skin (e.g., intradermally) of a subject. The cancer cells used to produce the protein concentrate or plasma membrane preparation may be autologous or allogeneic. In a specific embodiment, the backbone of the chimeric NDV is a lytic strain. The protein concentrate or plasma membrane preparation may be administered to a subject alone or in combination with an additional therapy. The protein concentrate or plasma membrane preparation is preferably in a pharmaceutical composition. In certain embodiments, the protein concentrate or plasma membrane preparation is administered in combination with one or more additional therapies, such as described in Section 5.6.4, infra (e.g., Section 5.6.4.1) In certain embodiments, the protein concentrate or plasma membrane preparation and one or more additional therapies are administered in the same composition. In other embodiments, the protein concentrate or plasma membrane preparation and one or more additional therapies are administered in different compositions.

In another aspect, a protein concentrate or plasma membrane preparation from lysed cancer cells infected with an NDV (e.g., an NDV described in Section 5.1, supra) may be used in combination with one or more additional therapies, such as described herein in Section 5.6.4, infra (e.g., Section 5.6.4.1), in the treatment of cancer. In one embodiment, provided herein are methods for treating cancer, comprising administering to a subject in need thereof a protein concentrate or plasma membrane preparation from lysed cancer cells infected with an NDV (e.g., an NDV described in Section 5.1, supra) in combination with one or more additional therapies, such as described herein in Section 5.6.4, infra. (e.g., Section 5.6.4.1). In a specific embodiment, provided herein is a method for treating cancer, comprising administering to a subject in need thereof an effective amount of a protein concentrate or plasma membrane preparation from lysed cancer cells infected with an NDV (e.g., an NDV described in Section 5.1, supra) in combination with an effective amount of one or more additional therapies, such as described in Section 5.6.4, infra. (e.g., Section 5.6.4.1). In certain embodiments, the protein concentrate or plasma membrane preparation and one or more additional therapies, such as described in Section 5.6.4, infra, are administered in the same composition. In other embodiments, the protein concentrate or plasma membrane preparation and one or more additional therapies are administered in different compositions.

In another aspect, the chimeric NDVs described herein (e.g., a chimeric NDV described in Section 5.2, supra) can be used to produce antibodies which can be used in diagnostic immunoassays, passive immunotherapy, and the generation of antiidiotypic antibodies. For example, a chimeric NDV described herein (e.g., a chimeric NDV described in Section 5.2, supra) can be administered to a subject (e.g., a mouse, rat, pig, horse, donkey, bird or human) to generate antibodies which can then be isolated and used, e.g., in diagnostic assays, passive immunotherapy and generation of antiidiotypic antibodies. In certain embodiments, an NDV described herein (e.g., an NDV described in Section 5.1 or 5.2, supra) is administered to a subject (e.g., a mouse, rat, pig, horse, donkey, bird, or human) in combination with one or more additional therapies, such as described in Section 5.6.4, infra, to generated antibodies which can then be isolated and used, e.g., in diagnostic assays, passive immunotherapy and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies.

In certain embodiments, the antibodies isolated from subjects administered a chimeric NDV described herein (e.g., a chimeric NDV described in Section 5.2, supra), or isolated from subjects administered an NDV described herein (e.g., an NDV described in Section 5.1 or 5.2, supra) in combination with one or more additional therapies, such as described in Section 5.6.4, infra, are used to assess the expression of NDV proteins, a heterologous peptide or protein expressed by a chimeric NDV, or both. Any immunoassay system known in the art may be used for this purpose including but not limited to competitive and non-competitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immuno-

5.6.1. Patient Population

In some embodiments, an NDV (e.g., a chimeric NDV) described herein or a composition thereof, an oncolysate vaccine described herein, or a whole cell vaccine described herein, or a combination therapy described herein is administered to a subject suffering from cancer. In other embodiments, an NDV (e.g., a chimeric NDV) described herein or a composition thereof, an oncolysate vaccine described herein, or a whole cell vaccine described herein, or a combination therapy described herein is administered to a subject predisposed or susceptible to cancer. In some embodiments, an NDV (e.g., a chimeric NDV) or a composition thereof, an oncolysate vaccine described herein, or a whole cell vaccine described herein, or a combination therapy described herein is administered to a subject diagnosed with cancer. Specific examples of the types of cancer are described herein. In an embodiment, the subject has metastatic cancer. In another embodiment, the subject has stage 1, stage 2 or stage 3 cancer. In another embodiment, the subject is in remission. In yet another embodiment, the subject has a recurrence of cancer.

In certain embodiments, an NDV (e.g., a chimeric NDV) or a composition thereof, an oncolysate vaccine described herein, or a whole cell vaccine described herein, or a combination therapy described herein is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an NDV (e.g., a chimeric NDV) or a composition thereof, an oncolysate vaccine described herein, or a whole cell vaccine described herein, or a combination therapy described herein is administered to a human infant. In other embodiments, an NDV (e.g., a chimeric NDV) or a composition thereof, an oncolysate vaccine described herein, or a whole cell vaccine described herein, or a combination therapy described herein is administered to a human toddler. In other embodiments, an NDV (e.g., a chimeric NDV) or a composition thereof, an oncolysate vaccine described herein, or a whole cell vaccine described herein, or a combination therapy described herein is administered to a human child. In other embodiments, an NDV (e.g., a chimeric NDV) or a composition thereof, an oncolysate vaccine described herein, or a whole cell vaccine described herein, or a combination therapy described herein is administered to a human adult. In yet other embodiments, an NDV (e.g., a chimeric NDV) or a composition thereof, an oncolysate vaccine described herein, or a whole cell vaccine described herein, or a combination therapy described herein is administered to an elderly human.

In certain embodiments, an NDV (e.g., a chimeric NDV) or a composition thereof, an oncolysate vaccine described herein, or a whole cell vaccine described herein, or a combination therapy described herein is administered to a subject in an immunocompromised state or immunosuppressed state or at risk for becoming immunocompromised or immunosuppressed. In certain embodiments, an NDV (e.g., a chimeric NDV) or a composition thereof, an oncolysate vaccine described herein, or a whole cell vaccine described herein, or a combination therapy described herein is administered to a subject receiving or recovering from immunosuppressive therapy. In certain embodiments, an NDV (e.g., a chimeric NDV) or a composition thereof, an oncolysate vaccine described herein, or a whole cell vaccine described herein, or a combination therapy described herein is administered to a subject that has or is at risk of getting cancer. In certain embodiments, the subject is, will or has undergone surgery, chemotherapy and/or radiation therapy. In certain embodiments, the patient has undergone surgery to remove the tumor or neoplasm. In specific embodiments, the patient is administered an NDV (e.g., a chimeric NDV) or a composition thereof, an oncolysate vaccine described herein, or a whole cell vaccine described herein, or a combination therapy described herein following surgery to remove a tumor or neoplasm. In other embodiment, the patient is administered an NDV (e.g., a chimeric NDV) or a composition thereof, an oncolysate vaccine described herein, or a whole cell vaccine described herein, or a combination therapy described herein prior to undergoing surgery to remove a tumor or neoplasm. In certain embodiments, an NDV (e.g., a chimeric NDV) or a composition thereof, an oncolysate vaccine described herein, or a whole cell vaccine described herein, or a combination therapy described herein is administered to a subject that has, will have or had a tissue transplant, organ transplant or transfusion.

In some embodiments, an NDV (e.g., a chimeric NDV) or a composition thereof, an oncolysate vaccine described herein, or a whole cell vaccine described herein, or a combination therapy described herein is administered to a patient who has proven refractory to therapies other than the chimeric NDV or composition thereof, oncolysate, whole cell vaccine, or a combination therapy but are no longer on these therapies. In a specific embodiment, an NDV (e.g., a chimeric NDV) or a composition thereof, an oncolysate vaccine described herein, or a whole cell vaccine described herein, or a combination therapy described herein is administered to a patient who has proven refractory to chemotherapy. In one embodiment, that a cancer is refractory to a therapy means that at least some significant portion of the cancer cells are not killed or their cell division arrested. The determination of whether the cancer cells are refractory can be made either in vivo or in vitro by any method known in the art for assaying the effect of a therapy on cancer cells, using the art-accepted meanings of "refractory" in such a context. In a certain embodiment, refractory patient is a patient refractory to a standard therapy. In certain embodiments, a patient with cancer, is refractory to a therapy when the tumor or neoplasm has not significantly been eradicated and/or the symptoms have not been significantly alleviated. The determination of whether a patient is refractory can be made either in vivo or in vitro by any method known in the art for assaying the effectiveness of a treatment of cancer, using art-accepted meanings of "refractory" in such a context.

In certain embodiments, the patient to be treated in accordance with the methods described herein is a patient already being treated with antibiotics, anti-virals, anti-fungals, or other biological therapy/immunotherapy or anti-cancer therapy. Among these patients are refractory patients, and patients who are too young for conventional therapies. In some embodiments, the subject being administered an NDV (e.g., a chimeric NDV), an oncolysate vaccine described herein, or a whole cell vaccine described herein, or a combination therapy described herein has not received therapy prior to the administration of the chimeric NDV or composition, the oncolysate vaccine, or the whole cell vaccine, or the combination therapy.

In some embodiments, an NDV (e.g., a chimeric NDV) or a composition thereof, an oncolysate vaccine described herein, or a whole cell vaccine described herein, or a combination therapy described herein is administered to a patient to prevent the onset of cancer in a patient at risk of developing cancer. In some embodiments, compounds are administered to a patient who are susceptible to adverse reactions to conventional therapies.

In some embodiments, the subject being administered an NDV (e.g., a chimeric NDV) or a composition thereof, an oncolysate vaccine described herein, or a whole cell vaccine described herein, or a combination therapy described herein has not received prior therapy. In other embodiments, an NDV (e.g., a chimeric NDV) or a composition thereof, an oncolysate vaccine described herein, or a whole cell vaccine described herein, or a combination therapy described herein is administered to a subject who has received a therapy prior to administration of the NDV (e.g., a chimeric NDV) or composition, the oncolysate vaccine, the whole cell vaccine, or the combination therapy. In some embodiments, the subject administered an NDV (e.g., a chimeric NDV) or a composition thereof, an oncolysate vaccine described herein, or a whole cell vaccine described herein, or a combination therapy described herein experienced adverse side effects to a prior therapy or a prior therapy was discontinued due to unacceptable levels of toxicity to the subject.

5.6.2. Dosage & Frequency

The amount of an NDV or a composition thereof, an oncolysate vaccine, or a whole cell vaccine which will be effective in the treatment of cancer will depend on the nature of the cancer, the route of administration, the general health of the subject, etc. and should be decided according to the judgment of a medical practitioner. Standard clinical techniques, such as in vitro assays, may optionally be employed to help identify optimal dosage ranges. However, suitable dosage ranges of an NDV for administration are generally about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and most preferably about $10^4$ to about $10^{12}$, $10^6$ to $10^{12}$, $10^8$ to $10^{12}$, $10^9$ to $10^{12}$ or $10^9$ to $10^{11}$, and can be administered to a subject once, twice, three, four or more times with intervals as often as needed. Dosage ranges of oncolysate vaccines for administration may include 0.001 mg, 0.005 mg, 0.01 mg, 0.05 mg. 0.1 mg. 0.5 mg, 1.0 mg, 2.0 mg. 3.0 mg, 4.0 mg, 5.0 mg, 10.0 mg, 0.001 mg to 10.0 mg, 0.01 mg to 1.0 mg, 0.1 mg to 1 mg, and 0.1 mg to 5.0 mg, and can be administered to a subject once, twice, three or more times with intervals as often as needed. Dosage ranges of whole cell vaccines for administration may include $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ cells, and can be administered to a subject once, twice, three or more times with intervals as often as needed. In certain embodiments, dosages similar to those currently being used in clinical trials for NDV, oncolysate vaccines or whole cell vaccines are administered to a subject. Effective doses may be extrapolated from dose response curves derived from in vitro or animal model test systems.

In certain embodiments, an NDV (e.g., a chimeric NDV) or a composition thereof is administered to a subject as a single dose followed by a second dose 1 to 6 weeks, 1 to 5 weeks, 1 to 4 weeks, 1 to 3 weeks, 1 to 2 weeks later. In accordance with these embodiments, booster inoculations may be administered to the subject at 6 to 12 month intervals following the second inoculation. In certain embodiments, an oncolysate vaccine or a whole cell vaccine is administered to a subject as a single dose followed by a second dose 1 to 6 weeks, 1 to 5 weeks, 1 to 4 weeks, 1 to 3 weeks, 1 to 2 weeks later.

In certain embodiments, administration of the same NDV (e.g., chimeric NDV) or a composition thereof, oncolysate vaccine, or whole cell vaccine may be repeated and the administrations may be separated by at least 1 day, 2 days, 3 days, 5 days, 6 days, 7 days, 10 days, 14 days, 15 days, 21 days, 28 days, 30 days, 45 days, 2 months, 75 days, 3 months, or at least 6 months. In other embodiments, administration of the same NDV (e.g., a NDV) or a composition thereof, oncolysate vaccine, or whole cell vaccine may be repeated and the administrations may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months. In some embodiments, a first NDV (e.g., a first chimeric NDV) or a composition thereof is administered to a subject followed by the administration of a second NDV (e.g., a second chimeric NDV) or a composition thereof. In certain embodiments, the first and second NDVs (e.g., the first and second chimeric NDVs) or compositions thereof may be separated by at least 1 day, 2 days, 3 days, 5 days, 6 days, 7 days, 10 days, 14 days, 15 days, 21 days, 28 days, 30 days, 45 days, 2 months, 75 days, 3 months, or at least 6 months. In other embodiments, the first and second NDVs (e.g., the first and second chimeric NDVs) or compositions thereof may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months.

In certain embodiments, an NDV or composition thereof, or oncolysate vaccine or whole cell vaccine is administered to a subject in combination with one or more additional therapies, such as a therapy described in Section 5.6.4, infra. The dosage of the other one or more additional therapies will depend upon various factors including, e.g., the therapy, the nature of the cancer, the route of administration, the general health of the subject, etc. and should be decided according to the judgment of a medical practitioner. In specific embodiments, the dose of the other therapy is the dose and/or frequency of administration of the therapy recommended for the therapy for use as a single agent is used in accordance with the methods disclosed herein. In other embodiments, the dose of the other therapy is a lower dose and/or less frequent administration of the therapy than recommended for the therapy for use as a single agent is used in accordance with the methods disclosed herein. Recommended doses for approved therapies can be found in the Physician's Desk Reference.

In certain embodiments, an NDV or composition thereof, or oncolysate vaccine or whole cell vaccine is administered to a subject concurrently with the administration of one or more additional therapies. In other embodiments, an NDV or composition thereof, or oncolysate vaccine or whole cell vaccine is administered to a subject every 3 to 7 days, 1 to 6 weeks, 1 to 5 weeks, 1 to 4 weeks, 2 to 4 weeks, 1 to 3 weeks, or 1 to 2 weeks and one or more additional therapies (such as described in Section 5.6.4, infra) is administered every 3 to 7 days, 1 to 6 weeks, 1 to 5 weeks, 1 to 4 weeks, 1 to 3 weeks, or 1 to 2 weeks. In certain embodiments, an NDV or composition thereof, or oncolysate vaccine or whole cell vaccine is administered to a subject every 1 to 2 weeks and one or more additional therapies (such as described in Section 5.6.4, infra) is administered every 2 to 4 weeks. In some embodiments, an NDV or composition thereof, or oncolysate vaccine or whole cell vaccine is administered to a subject every week and one or more additional therapies (such as described in Section 5.6.4, infra) is administered every 2 weeks.

5.6.3. Types of Cancer

Specific examples of cancers that can be treated in accordance with the methods described herein include, but are not limited to: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, placancer cell leukemia, solitary placancercytoma and extramedullary placancercytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, glioblastoma multiforme, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-cancer cell lung cancer, squamous cell carcinoma (epidermoid carcinoma), adenocarcinoma, large-cell carcinoma and cancer-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a specific embodiment, the chimeric NDVs described herein or compositions thereof, an oncolysate vaccine described herein, a whole cell vaccine herein, or a combination therapy described herein are useful in the treatment of a variety of cancers and abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoacanthoma, seminoma, thyroid follicular cancer and teratocarcinoma.

In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma or melanoma is treated in accordance with the methods described herein.

In a specific embodiment, the cancer being treated in accordance with the methods described herein is leukemia, lymphoma or myeloma (e.g., multiple myeloma). Specific examples of leukemias and other blood-borne cancers that can be treated in accordance with the methods described herein include, but are not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", and hairy cell leukemia.

Specific examples of lymphomas that can be treated in accordance with the methods described herein include, but are not limited to, Hodgkin's disease, non-Hodgkin's Lymphoma, Multiple myeloma, Waldenstrom's macroglobulinemia, Heavy chain disease, and Polycythemia vera.

In another embodiment, the cancer being treated in accordance with the methods described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, cancer cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. In another embodiment, the cancer being treated in accordance with the methods described herein is a metastatic. In another embodiment, the cancer being treated in accordance with the methods described herein is malignant.

In a specific embodiment, the cancer being treated in accordance with the methods described herein is a cancer that has a poor prognosis and/or has a poor response to conventional therapies, such as chemotherapy and radiation. In another specific embodiment, the cancer being treated in accordance with the methods described herein is malignant melanoma, malignant glioma, renal cell carcinoma, pancreatic adenocarcinoma, malignant pleural mesothelioma, lung adenocarcinoma, lung small cell carcinoma, lung squamous cell carcinoma, anaplastic thyroid cancer, and head and neck squamous cell carcinoma.

5.6.4. Additional Therapies

Additional therapies that can be used in a combination with an NDV described herein or a composition thereof, an oncolysate vaccine, or a whole cell vaccine for the treatment of cancer include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. In a specific embodiment, the additional therapy is a chemotherapeutic agent.

In some embodiments, an NDV described herein or a composition thereof, an oncolysate vaccine, or a whole cell vaccine is used in combination with radiation therapy comprising the use of x-rays, gamma rays and other sources of radiation to destroy cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer cells and/or a tumor mass.

Currently available cancer therapies and their dosages, routes of administration and recommended usage are known in the art and have been described in such literature as the Physician's Desk Reference (67th ed., 2013).

Specific examples of anti-cancer agents that may be used in combination with an NDV described herein or a composition thereof include: hormonal agents (e.g., aromatase inhibitor, selective estrogen receptor modulator (SERM), and estrogen receptor antagonist), chemotherapeutic agents (e.g., microtubule disassembly blocker, antimetabolite, topoisomerase inhibitor, and DNA crosslinker or damaging agent), anti-angiogenic agents (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with an NDV described herein or a composition thereof include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as) Nolvadex®, afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with an NDV described herein or a composition thereof, an oncolysate vaccine, or a whole cell vaccine include microtubule disasssembly blocker, antimetabolite, topoisomerase inhibitor, and DNA crosslinker or damaging agent. Chemotherapeutic agents that are microtubule disassembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®.

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capecitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®, lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

5.6.4.1 Immune Modulators

In specific embodiments, an NDV described herein (e.g., a chimeric NDV) or a composition thereof, an oncolysate vaccine, or a whole cell vaccine are administered to a subject in combination with one or more of the following: any agonist of a co-stimulatory signal of an immune cell (such as, e.g., a T-lymphocyte, NK cell or antigen-presenting cell (e.g., a dendritic cell or macrophage) and/or any antagonist of an inhibitory signal of an immune cell (such as, e.g., a T-lymphocyte, NK cell or antigen-presenting cell (e.g., a dendritic cell or macrophage), known to one of skill in the art. In particular embodiments, an NDV described herein (e.g., a chimeric NDV) or a composition thereof, an oncolysate vaccine, or a whole cell vaccine are administered to a subject in combination with one or more of the agonists of a co-stimulatory signal of an immune cell described in Section 5.2.1, supra. In some embodiments, an NDV described herein (e.g., a chimeric NDV) or a composition thereof, an oncolysate vaccine, or a whole cell vaccine are administered to a subject in combination with one or more of the antagonists of an inhibitory signal of an immune cell described in Section 5.2.1, supra. In certain embodiments, an NDV described herein (e.g., a chimeric NDV) or a composition thereof, an oncolysate vaccine, or a whole cell vaccine are administered to a subject in combination with one or more of the agonists of a co-stimulatory signal of an immune cell and/or one or more of the antagonists of an inhibitory signal of an immune cell described in Section 6, infra (e.g., an anti-CTLA-4 antibody or an ICOS-L)

5.7 Biological Assays

In Vitro Viral Assays

Viral assays include those that measure altered viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of the NDVs described herein can be assessed by any method known in the art or described herein (e.g., in cell culture (e.g., cultures of chicken embryonic kidney cells or cultures of chicken embryonic fibroblasts (CEF)). Viral titer may be determined by inoculating serial dilutions of a NDV described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50). An exemplary method of assessing viral titer is described in Section 6, below.

Incorporation of nucleotide sequences encoding a heterologous peptide or protein (e.g., a cytokine, a mutated F protein, a mutated V protein, or miRNA target site into the genome of a chimeric NDV described herein can be assessed by any method known in the art or described herein (e.g., in cell culture, an animal model or viral culture in embryonated eggs). For example, viral particles from cell culture of the allantoic fluid of embryonated eggs can be purified by centrifugation through a sucrose cushion and subsequently analyzed for fusion protein expression by Western blotting using methods well known in the art.

Immunofluorescence-based approaches may also be used to detect virus and assess viral growth. Such approaches are well known to those of skill in the art, e.g., fluorescence microscopy and flow cytometry (see Section 6, infra).

Antibody Assays

Antibodies generated by the NDVs described herein may be characterized in a variety of ways well-known to one of skill in the art (e.g., ELISA, Surface Plasmon resonance display (BIAcore), Western blot, immunofluorescence, immunostaining and/or microneutralization assays). In particular, antibodies generated by the chimeric NDVs described herein may be assayed for the ability to specifically bind to an antigen of the virus or a heterologous peptide or protein. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403, 484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Antibodies generated by the chimeric NDVs described herein that have been identified to specifically bind to an antigen of the virus or a heterologous peptide or protein can be assayed for their specificity to said antigen of the virus or heterologous peptide or protein. The antibodies may be assayed for specific binding to an antigen of the virus or a heterologous peptide or protein and for their cross-reactivity with other antigens by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an antigen and the off-rate of an antibody-antigen interaction can be determined by competitive binding assays. Alternatively, a surface plasmon resonance assay (e.g., BIAcore kinetic analysis) or KinExA assay (Blake, et al., *Analytical Biochem.,* 1999, 272:123-134) may be used to determine the binding on and off rates of antibodies to an antigen of the chimeric NDVs described herein.

IFN Assays

IFN induction and release by an NDV described herein may be determined using techniques known to one of skill in the art or described herein. For example, the amount of IFN induced in cells following infection with an NDV described herein may be determined using an immunoassay (e.g., an ELISA or Western blot assay) to measure IFN expression or to measure the expression of a protein whose expression is induced by IFN. Alternatively, the amount of IFN induced may be measured at the RNA level by assays, such as Northern blots and quantitative RT-PCR, known to one of skill in the art. In specific embodiments, the amount of IFN released may be measured using an ELISPOT assay. (See, e.g., the methods described in Section 6, below.)

Activation Marker Assays

Techniques for assessing the expression of activation marker, co-stimulatory molecule, ligand, or inhibitory molecule by immune cells are known to one of skill in the art. For example, the expression of an activation marker, co-stimulatory molecule, ligand, or inhibitory molecule by an immune cell (e.g., T lymphocyte or NK cell) can be assessed by flow cytometry. In a specific embodiment, techniques described in Section 6, infra, are used to assess the expression of an activation marker, co-stimulatory molecule, ligand, or inhibitory molecule by an immune cell.

Immune Cell Infiltration Assays

Techniques for assessing immune cell infiltration are known to one of skill in the art. In a specific embodiment, techniques described in Section 6, infra, are used to assess immune cell infiltration.

Toxicity Studies

In some embodiments, the NDVs described herein or compositions thereof, oncolysate vaccines described herein, whole cell vaccines described herein, or combination therapies described herein are tested for cytotoxicity in mammalian, preferably human, cell lines (see, e.g., the cytotoxicity assay described in Section 6, infra). In certain embodiments, cytotoxicity is assessed in one or more of the following non-limiting examples of cell lines: U937, a human monocyte cell line; primary peripheral blood mononuclear cells (PBMC); Huh7, a human hepatoblastoma cell line; HL60 cells, HT1080, HEK 293T and 293H, MLPC cells, human embryonic kidney cell lines; human melanoma cell lines, such as SkMel2, SkMel-119 and SkMel-197; THP-1, monocytic cells; a HeLa cell line; and neuroblastoma cells lines, such as MC-IXC, SK-N-MC, SK-N-MC, SK-N-DZ, SH-SY5Y, and BE(2)-C. In certain embodiments, cytotoxicity is assessed in various cancer cells. In some embodiments, the ToxLite assay is used to assess cytotoxicity.

Many assays well-known in the art can be used to assess viability of cells or cell lines following infection with an NDV described herein or composition thereof, or treatment with an oncolysate vaccine described herein, a whole cell vaccine described herein, or a combination therapy described herein and, thus, determine the cytotoxicity of the NDV or composition thereof, oncolysate vaccine, whole cell vaccine, or combination therapy. For example, cell proliferation can be assayed by measuring Bromodeoxyuridine (BrdU) incorporation, ($^3$H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypanblue staining or other cell death or viability markers known in the art. In a specific embodiment, the level of cellular ATP is measured to determined cell viability. In preferred embodiments, an NDV described herein or composition thereof, oncolysate vaccine, whole cell vaccine, or combination therapy kills cancer cells but does not kill healthy (i.e., non-cancerous) cells. In one embodiment, an NDV described herein or composition thereof, oncolysate vaccine, whole cell vaccine, or combination therapy preferentially kills cancer cells but does not kill healthy (i.e., non-cancerous) cells.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes.

The NDVs described herein or compositions thereof, oncolysate vaccines, whole cell vaccines or combination therapies can be tested for in vivo toxicity in animal models (see, e.g., the animal models described in Section 6, below). For example, animal models, described herein and/or others known in the art, used to test the effects of compounds on cancer can also be used to determine the in vivo toxicity of the NDVs described herein or compositions thereof, oncolysate vaccines, whole cell vaccines, or combination therapies. For example, animals are administered a range of pfu of an NDV described herein (e.g., a chimeric NDV described in Section 5.2, infra). Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an NDV described herein or a composition thereof, an oncolysate vaccine described herein, a whole cell vaccine described herein, or a combination therapy described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibits large therapeutic indices are preferred. While therapies that exhibits toxic side effects may be used, care should be taken to design a delivery system that targets such therapies to the site of affected tissue in order to minimize potential damage to noncancerous cells and, thereby, reduce side effects.

The data obtained from the cell culture assays and animal studies can be used in formulating a range of dosage of the therapies for use in subjects. The dosage of such agents lies preferably within a range of circulating concentrations that include the ED50 with little or no toxicity. The dosage may vary within this range depending upon the dosage form employed and the route of administration utilized. For any therapy described herein, the therapeutically effective dose can be estimated initially from cell culture assays. A dose may be formulated in animal models to achieve a circulating plasma concentration range that includes the IC50 (i.e., the concentration of the chimeric NDV that achieves a half-maximal inhibition of symptoms) as determined in cell culture. Such information can be used to more accurately determine useful doses in subjects. Levels in plasma may be measured, for example, by high performance liquid chromatography.

Anti-Cancer Studies

The NDVs described herein or compositions thereof, oncolysate vaccines described herein, whole cell vaccines described herein, or combination therapies described herein can be tested for biological activity using animal models for cancer. Such animal model systems include, but are not limited to, rats, mice, chicken, cows, monkeys, pigs, dogs, rabbits, etc. In a specific embodiment, the anti-cancer activity of an NDV described herein or combination therapy is tested in a mouse model system. Such model systems are widely used and well-known to the skilled artisan such as the SCID mouse model or transgenic mice.

The anti-cancer activity of an NDV described herein or a composition thereof, oncolysate vaccine described herein, whole cell vaccine described herein, or a combination therapy described herein can be determined by administering the NDV or composition thereof, oncolysate vaccine, whole cell vaccine, or combination therapy to an animal model and verifying that the NDV or composition thereof, oncolysate vaccine, whole cell vaccine, or combination therapy is effective in reducing the severity of cancer, reducing the symptoms of cancer, reducing cancer metastasis, and/or reducing the size of a tumor in said animal model (see, e.g., Section 6, below). Examples of animal models for cancer in general include, include, but are not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In-vivo 8(5):755-69) and a transgenic mouse model with disrupted p53 function (see, e.g. Morris et al., 1998, J La State Med Soc 150(4): 179-85). An example of an animal model for breast cancer includes, but is not limited to, a transgenic mouse that over expresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res. 61(6):2395-8). Examples of animal models for pancreatic cancer include, but are not limited to, a metastatic model of PancO2 murine pancreatic adenocarcinoma (see, e.g., Wang et al., 2001, Int. J. Pancreatol. 29(1):37-46) and nu-nu mice generated in subcutaneous pancreatic tumors (see, e.g., Ghaneh et al., 2001, Gene Ther. 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc. Natl. Acad. Sci. USA 95(23):13853-8). An example of an animal model for esophageal cancer includes, but is not limited to, a mouse transgenic for the human papillomavirus type 16 E7 oncogene (see, e.g., Herber et al., 1996, J. Virol. 70(3):1873-81). Examples of animal models for colorectal carcinomas include, but are not limited to, Apc mouse models (see, e.g., Fodde & Smits, 2001, Trends Mol Med 7(8):369 73 and Kuraguchi et al., 2000). In a specific embodiment, the animal models for cancer described in Section 6, infra, are used to assess efficacy of an NDV or composition thereof, an oncolysate, a whole cell vaccine, or a combination therapy.

6. EXAMPLE

This example demonstrates the therapeutic efficacy of NDV therapy in combination with immune checkpoint modulators that are immunostimulatory in the treatment of cancer.

6.1 Materials & Methods

Mice

BALB/c mice (6-8 weeks old), and WT C57BL/6 mice were purchased from Jackson Laboratory. All mice were maintained in microisolator cages and treated in accordance with the NIH and American Association of Laboratory Animal Care regulations. All mouse procedures and experiments for this study were approved by the Memorial Sloan-Kettering Cancer Center Institutional Animal Care and Use Committee.

Cell Lines

The murine cancer cell lines for melanoma (B16-F10), and colon carcinoma (CT26 and MC38) were maintained in RPMI medium supplemented with 10% fetal calf serum and penicillin with streptomycin. The murine prostate cancer cell line TRAMP-C2 was maintained in DMEM medium supplemented with 5% fetal calf serum (FCS; Mediatech, Inc.), 5% Nu Serum IV (BD Biosciences) HEPES, 2-ME, pen/strep. L-glut, 5 µg/mL insulin (Sigma), and 10 nmol/L DHT (Sigma).

Antibodies

Therapeutic anti-CTLA-4 (clone 9H10), anti-PD-1 (clone RMP1-14), and anti-PD-L1 monoclonal antibodies were produced by BioXcell. Antibodies used for flow cytometry were purchased from eBioscience, Biolegend, Invitrogen, and BD Pharmingen.

Viruses and Cloning

Recombinant lentogenic NDV LaSota strain was used for all experiments. To generate NDV virus expressing murine ICOSL, a DNA fragment encoding the murine ICOSL flanked by the appropriate NDV-specific RNA transcriptional signals was inserted into the SacII site created between the P and M genes of pT7NDV/LS. Viruses were rescued from cDNA using methods described previously and sequenced by reverse transcription PCR for insert fidelity. Virus titers were determined by serial dilution and immunofluorescence in Vero cells. Recombinant ICOSL-F fusion construct was generated by PCR amplification of the ICOSL DNA encoding the extracellular domain (amino acids 1-277) with flanking EcoRI and MluI restriction sites, and the NDV F DNA encoding the F transmembrane and intracellular domains (amino acids 501-554) with flanking MluI and XhoI restriction sites. The resultant DNA fragments were assembled in pCAGGS vector utilizing 3-part ligation.

In Vitro Infection Experiments

For evaluation of upregulation of surface MHC-I, MHC-II, and ICAM-1 by NDV, and for evaluation of surface expression of the ICOSL transgene from the NDV-ICOSL virus, B16-F10 cells were infected in 6-well dishes at MOI 2 in triplicate. Twenty-four hours later, the cells were harvested by mechanical scraping and processed for surface labeling and quantification by flow cytometry. For virus growth curve experiments, B16-F10 cells were incubated at room temperature with the virus in 6-well culture dishes at the indicated MOIs in a total volume of 100 µl. One hour after the incubation, the infection media was aspirated and the cells were incubated at 37° C. in 1 ml of DMEM with 10% chick allantoic fluid. After 24, 48, and 72 hours, the supernatants were collected and virus titers were determined as above. For in vitro cytotoxicity experiments, the infections were carried out in a similar fashion. At 24, 48, 72, and 96 hours post infection the cells were washed and incubated with 1% Triton X-100 at 37° C. for 30 minutes. LDH activity in the lysates was determined using the Promega CytoTox 96 assay kit, according to the manufacturer's instructions.

Tumor Challenge Survival Experiments.

Bilateral flank tumor models were established to monitor for therapeutic efficacy in both injected and systemic tumors. Treatment schedules and cell doses were established for each tumor model to achieve 10-20% tumor clearance by NDV or anti-CTLA-4/anti-PD-1 as single agents. For experiments evaluating combination therapy of wild-type NDV (NDV-WT) with immune checkpoint blockade, B16F10 tumors were implanted by injection of $2\times10^5$ B16F10 cells in the right flank i.d. on day 0 and $5>10^4$ cells in the left flank on day 4. On days 7, 10, 13, and 16 the mice were treated with 4 intratumoral injections of $2\times10^7$ pfu of NDV in PBS in a total volume of 100 µl. Concurrently, on days 7, 10, 13, and 16 the mice received 4 i.p. injections of anti-CTLA-4 antibody (100 µg) or anti-PD-1 antibody (250 µg). Control groups received a corresponding dose of isotype antibody i.p. and intratumoral injection of PBS. Tumor size and incidence were monitored over time by measurement with a caliper.

For the TRAMP-C2 model, $5\times10^5$ cells were implanted in right flank on day 0 and $5\times10^5$ cells were implanted in the left flank on day 8. Treatment was performed on days 11, 14, 17, and 20 in the similar fashion to above.

For experiments evaluating recombinant NDV expressing ICOSL (NDV-ICOSL), B16F10 tumors were implanted by injection of $2\times10^5$ B16F10 cells in the right flank i.d. on day 0 and $1\times10^5$ cells in the left flank on day 4. Treatment was carried out as above.

For the CT26 model, tumors were implanted by injection of $1\times10^6$ CT26 cells in the right flank i.d. on day 0 and $1\times10^6$ cells in the left flank on day 2. Treatment was carried out as above on days 6, 9, and 12.

Isolation of Tumor-Infiltrating Lymphocytes

B16F10 tumors were implanted by injection of $2\times10^5$ B16F10 cells in the right flank i.d. on day 0 and $2\times10^5$ cells in the left flank on day 4. On days 7, 10, and 13 the mice were treated with 3 intratumoral injections of $2\times10^7$ pfu of NDV, and 100 µg of i.p. anti-CTLA-4 antibody or 250 µg of i.p. anti-PD-1 antibody, where specified. On day 15, mice were sacrificed by $CO_2$ inhalation. Tumors and tumor-draining lymph nodes were removed using forceps and surgical scissors and weighed. Tumors from each group were minced with scissors prior to incubation with 1.67 Wünsch U/mL Liberase and 0.2 mg/mL DNase for 30 minutes at 37° C. Tumors were homogenized by repeated pipetting and filtered through a 70-µm nylon filter. Cell suspensions were washed once with complete RPMI and purified on a Ficoll gradient to eliminate dead cells. Cells from tumor draining lymph nodes were isolated by grinding the lymph nodes through a 70-µm nylon filter.

Flow Cytometry

Cells isolated from tumors or tumor-draining lymph nodes were processed for surface labeling with several antibody panels staining CD45, CD3, CD4, CD8, CD44, PD-1, ICOS, CD11c, CD19, NK1.1, CD11b, F4/80, Ly6C and Ly6G. Fixable viability dye eFluor780 (eBioscience) was used to distinguish the live cells. Cells were further permeabilized using FoxP3 fixation and permeabilization kit (eBioscience) and stained for Ki-67, FoxP3, Granzyme B, CTLA-4, and IFN gamma. Data was acquired using the LSRII Flow cytometer (BD Biosciences) and analyzed using FlowJo software (Treestar).

DC Purification and Loading

Spleens from naïve mice were isolated and digested with 1.67 Wünsch U/mL Liberase and 0.2 mg/mL DNase for 30 minutes at 37° C. The resulting cell suspensions were filtered through 70 µm nylon filter and washed once with complete RPMI. CD11c+ dendritic cells were purified by positive selection using Miltenyi magnetic beads. Isolated dendritic cells were cultured overnight with recombinant GM-CSF and B16-F10 tumor lysates and were purified on Ficoll gradient.

Analysis of Cytokine Production

Cell suspensions from tumors or tumor-draining lymph nodes were pooled and enriched for T cells using a Miltenyi T-cell purification kit. Isolated T cells were counted and co-cultured for 8 hours with dendritic cells loaded with B16-F10 tumor cell lysates in the presence of 20 U/ml IL-2

(R and D) plus Brefeldin A (BD Bioscience). After restimulation, lymphocytes were processed for flow cytometry as above.

Statistics.

Data were analyzed by 2-tailed Student's t test, and P<0.05 was considered statistically significant.

6.2 Results

Figures 5A, 5B:
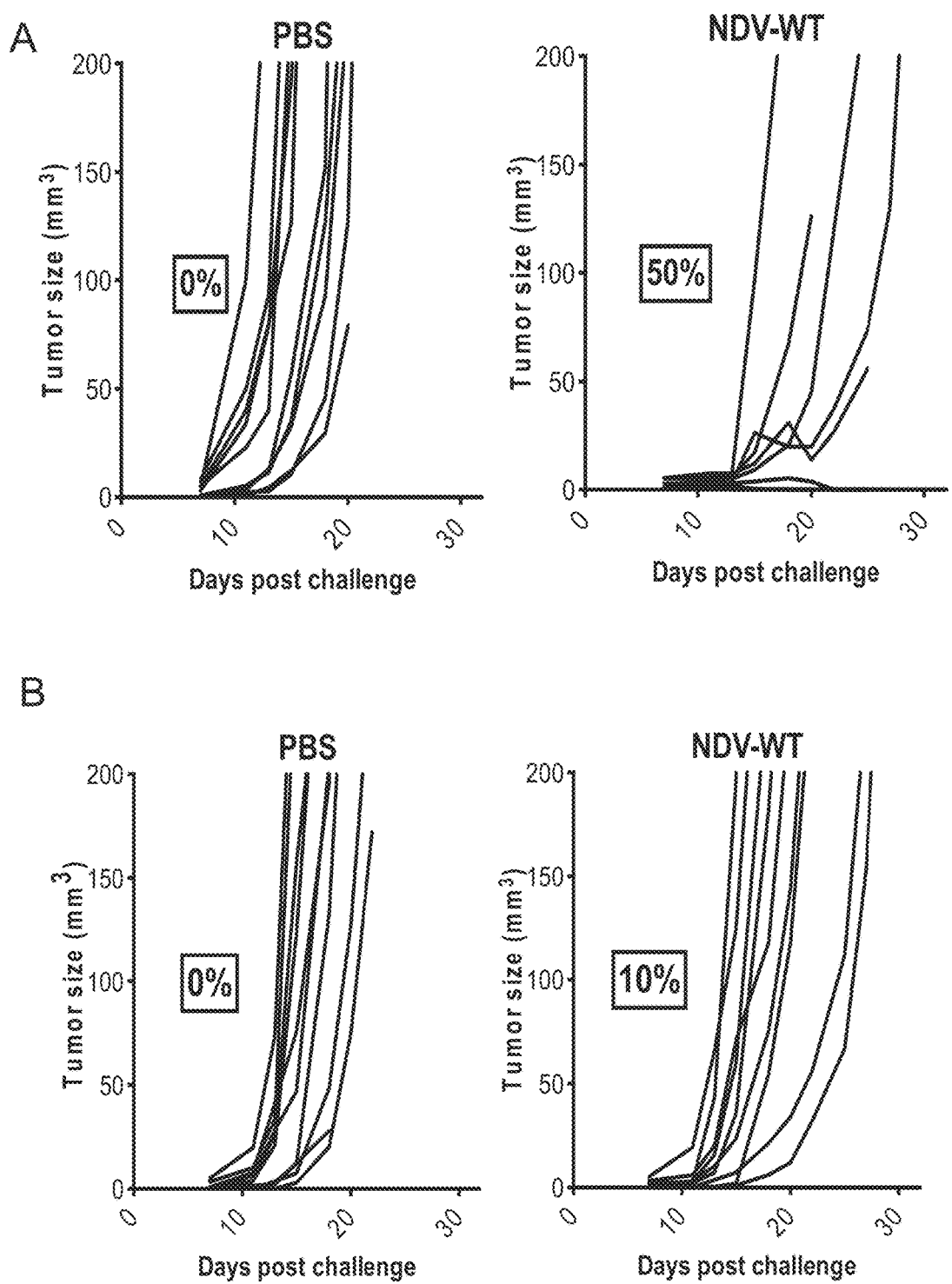
Figure 5C:
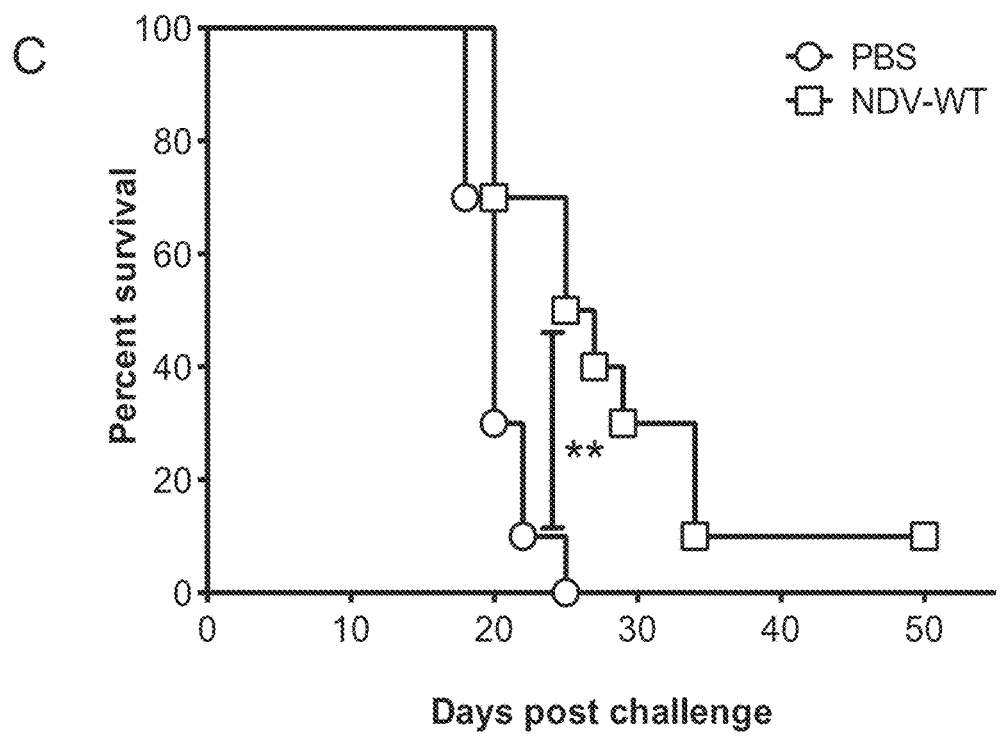
Figure 5D:
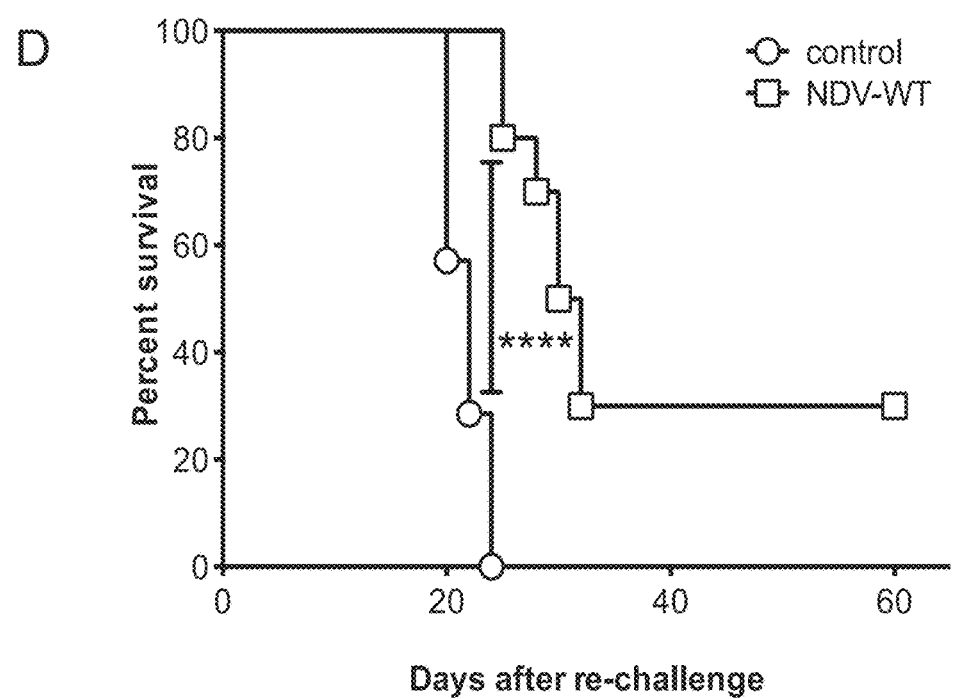

In order to characterize the anti-tumor immune response induced by Newcastle disease virus (NDV) infection, the expression of MHC I and MHC II molecules as well as ICAM-1 on the surface of in vitro infected cells was assessed. As shown in FIG. 1, NDV infection in B16 melanoma cells induces upregulation of MHC class I and II molecules as well as adhesion molecule ICAM-1, all of which are thought to be important for recruitment of tumor-specific lymphocytes and activation of anti-tumor immune response. Next, the anti-tumor immune response induced by NDV infection in vivo was assessed in a murine melanoma model and an established 2-flank model that allowed us to monitor responses both in the virus-injected tumors as well as distant tumors which do not receive the virus. As shown in FIG. 2, the virus-infected tumors show dramatic infiltration with immune cells such as NK cells, macrophages, and CD8 and CD4 cells, but not regulatory T cells. Since part of this immune response could be a response to virus, rather than tumor, the immune response with respect to contralateral tumors was assessed (FIG. 3). Interestingly, these tumors demonstrated a similar degree of increased CD8 and CD4 effector, but not T reg infiltrate. Analysis of these cells revealed that they upregulate activation, proliferation, and lytic markers (FIG. 4). NDV monotherapy was effective in controlling the treated tumors (FIG. 5A), but only marginally slowed down the growth of the contralateral tumors (FIG. 5B). Mice that cleared the tumors, however, demonstrated some degree of protection against further tumor challenge (FIG. 5D), suggesting that NDV therapy can induce a lasting immunity.

Next, it was assessed whether additional mechanisms could be targeted to enhance the anti-tumor effect generated by NDV. Characterization of tumor-infiltrating lymphocytes from both NDV-injected and non-injected tumors revealed upregulation of the inhibitory receptor CTLA-4 on lymphocytes (FIG. 6). It was then assessed whether inhibition of the CTLA-4 receptor could result in a better therapeutic efficacy of NDV. Strikingly, combination therapy resulted in rejection in bilateral tumors in the majority of the animals, an effect that was not seen with either treatment alone (FIG. 7). This effect was present even when the prostate adenocarcinoma TRAMP model was used, which is not susceptible to viral infection (FIG. 8), suggesting that the minimal viral replication and the resultant inflammatory response were sufficient for generation of protective anti-tumor immunity.

To determine whether targeting other immune checkpoints in combination with NDV therapy could be beneficial, the effect on the PD-1-PD-L1 pathway following NDV infection was assessed. As shown in FIG. 9, NDV infected tumor cells both in vitro and in vivo had upregulated the expression of the inhibitory PD-L1 ligand on the surface of the cells. This effect was not just a result of a direct virus infection, but was also seen when non-infected cells were treated with UV-inactivated supernatants from the virus infected cells (FIG. 9B) and in contralateral, noninfected, tumors (FIG. 9C). This prompted testing combination therapy with NDV and anti-PD-1 antibody. Similar to CTLA-4 blockade, NDV therapy in combination with anti-PD-1 in the aggressive B16 melanoma model resulted in cures in the majority of animals, an effect that was associated with increased tumor infiltration with activated effector lymphocytes (FIG. 10).

Throughout the studies conducted, the therapeutic efficacy of a combination therapy decreased when larger tumor challenge was used. Next, activation markers that could predict a better response and could be targeted for further improvement in therapeutic efficacy were assessed. Analysis of lymphocytes isolated from the tumors and tumor-draining lymph nodes identified upregulation of the co-stimulatory molecule ICOS as one of the activation markers in the treated animals (FIG. 11). ICOS upregulation has been previously been shown to be associated with more durable therapeutic responses and increased survival in patients treated with anti-CTLA-4 therapy for malignant melanoma. It was assessed whether intratumoral expression of the ICOS ligand (ICOSL) could further boost the therapeutic response of combination therapy. Using reverse-genetics system for NDV, NDV expressing murine ICOSL (NDV-ICOSL) were generated. In vitro characterization of the virus revealed that it had similar replicative and lytic properties to the parental NDV strain (FIG. 12). When tested in vivo, however, with a larger B16 tumor challenge, NDV-ICOSL demonstrated significant advantage over the parental NDV virus when used in combination with CTLA-4 blockade, with long-term survival in the majority of treated animals (FIG. 13). This effect was not limited to B16 melanoma and was demonstrated for CT26 colon carcinoma in the Balb/C mouse strain, suggesting that this therapeutic strategy could be translatable to different tumor types (FIG. 14). Analysis of B16 tumors from the treated animals demonstrated significant infiltration with different immune cell subtypes with upregulation of the activation markers (FIGS. 15 and 16). These lymphocytes were tumor-specific and demonstrated secretion of IFN gamma in response to stimulation with dendritic cells loaded with tumor lysates (FIG. 17). Finally, animals that were cured of their B16 or CT26 tumors were re-challenged with tumor cells and demonstrated complete protection against tumor re-challenge (FIG. 18).

To further improve the expression of the ICOSL in the tumor and to incorporate the ligand into the virion, a chimeric protein consisting of the extracellular domain of the ICOSL (amino acids 1-277) and the transmembrane and intracellular domains of the NDV F protein (amino acids 501-554) was generated (FIG. 19A). Transfection of the resultant construct into B16-F10 cells resulted in increased expression of the chimeric ICOSL-F ligand on the surface of the transfected cells, when compared to the transfected native ICOSL, suggesting that the regulatory mechanisms governing the transport of NDV F protein to the surface can be utilized to increase the surface expression of immune stimulatory ligands.

Overall, these studies demonstrate that 1) combination of NDV with immune checkpoint regulatory antibodies can be used as a strategy to circumvent the limitation of both oncolytic virus therapy and antibody therapy; and 2) expression of immunostimulatory ligands by NDV can further improve the therapeutic efficacy of the virus, especially when used in combination with immunoregulatory antibodies. These findings have clinical application.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A method for treating cancer, comprising administering to a human subject in need thereof a chimeric New Castle Disease Virus (NDV) and an antagonist of an inhibitory receptor of an immune cell, wherein the chimeric NDV comprises a packaged genome comprising a nucleotide sequence encoding a cytokine, wherein the cytokine is expressed by the NDV, wherein the cytokine is IL-12, wherein the inhibitory receptor is PD1, and wherein the antagonist is an antibody that specifically binds to the inhibitory receptor.

2. The method of claim 1, wherein the antibody is a monoclonal antibody.

3. The method of claim 1, wherein the cancer is melanoma, colorectal cancer, breast cancer, ovarian cancer, renal cell carcinoma, head and neck squamous cell carcinoma, pancreatic cancer, bladder cancer, cervical cancer, Hodgkin's disease, endometrial carcinoma, esophageal cancer, glioblastoma multiforme, hepatocellular carcinoma, lung cancer, mesothelioma, non-Hodgkin's lymphoma, prostate cancer, sarcoma, thyroid cancer or uterine cancer.

4. The method of claim 1, wherein the chimeric NDV is of the LaSota strain.

5. The method of claim 1, wherein the chimeric NDV is administered to the subject intratumorally.

6. The method of claim 1, wherein the packaged genome encodes a mutated F protein with the amino acid mutation L289A, wherein the mutated F protein is expressed by the chimeric NDV.

7. The method of claim 1, wherein the nucleotide sequence encoding the cytokine is between the P and M genes of the NDV.

8. The method of claim 1, wherein the cancer is metastatic.

9. The method of claim 1, wherein the antagonist is administered to the subject intravenously.

10. A method for treating cancer, comprising administering to a human subject in need thereof a composition comprising a chimeric NDV and a composition comprising an antagonist of an inhibitory receptor of an immune cell, wherein the chimeric NDV comprises a packaged genome comprising a nucleotide sequence encoding a cytokine, wherein the cytokine is expressed by the NDV, wherein the cytokine is IL-12, wherein the inhibitory receptor is PD1, and wherein the antagonist is a monoclonal antibody that specifically binds to the inhibitory receptor and blocks binding to its native ligands.

11. A method for treating cancer, comprising administering to a human subject in need thereof a composition comprising a chimeric NDV and a composition comprising an antagonist of an inhibitory receptor of an immune cell, wherein the chimeric NDV is of the LaSota strain and the chimeric NDV comprises a packaged genome comprising a nucleotide sequence encoding a cytokine and a nucleotide sequence encoding a mutated F protein with the amino acid mutation L289A, wherein the nucleotide sequence encoding the cytokine is between the P and M genes of the NDV, wherein the cytokine and mutated F protein are expressed by the NDV, wherein the cytokine is IL-12, wherein the inhibitory receptor is PD1, and wherein the antagonist is a monoclonal antibody that specifically binds to the inhibitory receptor and blocks binding to its native ligands.

12. The method of claim 10, wherein the chimeric NDV is of the LaSota strain.

13. The method of claim 10, wherein the composition comprising the chimeric NDV is administered to the subject intratumorally.

14. The method of claim 11, wherein the composition comprising the chimeric NDV is administered to the subject intratumorally.

15. The method of claim 13, wherein the cancer is metastatic.

16. The method of claim 14, wherein the cancer is metastatic.

17. The method of claim 13, wherein the composition comprising the antagonist is administered to the subject intravenously.

18. The method of claim 14, wherein the composition comprising the antagonist is administered to the subject intravenously.

19. The method of claim 13, wherein the cancer is melanoma, colorectal cancer, breast cancer, ovarian cancer, renal cell carcinoma, head and neck squamous cell carcinoma, pancreatic cancer, bladder cancer, cervical cancer, Hodgkin's disease, endometrial carcinoma, esophageal cancer, glioblastoma multiforme, hepatocellular carcinoma, lung cancer, mesothelioma, non-Hodgkin's lymphoma, prostate cancer, salivary gland cancer, sarcoma, thyroid cancer, or uterine cancer.

20. The method of claim 14, wherein the cancer is melanoma, colorectal cancer, breast cancer, ovarian cancer, renal cell carcinoma, head and neck squamous cell carcinoma, pancreatic cancer, bladder cancer, cervical cancer, Hodgkin's disease, endometrial carcinoma, esophageal cancer, glioblastoma multiforme, hepatocellular carcinoma, lung cancer, mesothelioma, non-Hodgkin's lymphoma, prostate cancer, salivary gland cancer, sarcoma, thyroid cancer, or uterine cancer.

* * * * *